(12) United States Patent
Black et al.

(10) Patent No.: US 12,241,088 B2
(45) Date of Patent: *Mar. 4, 2025

(54) UTERINE-DERIVED REGENERATIVE CELL COMPOSITIONS AND USES THEREOF

(71) Applicant: Gallant Pet, Inc., San Diego, CA (US)

(72) Inventors: Linda Black, San Diego, CA (US); Shelly Zacharias, San Diego, CA (US); Theodore T. Sand, San Diego, CA (US); Samuel Barillas, San Diego, CA (US); Rachel Bautista, San Diego, CA (US)

(73) Assignee: Gallant Pet, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/589,909

(22) Filed: Feb. 28, 2024

(65) Prior Publication Data

US 2024/0200034 A1    Jun. 20, 2024

Related U.S. Application Data

(63) Continuation of application No. 17/997,861, filed as application No. PCT/US2021/031148 on May 6, 2021.

(60) Provisional application No. 63/022,302, filed on May 8, 2020.

(51) Int. Cl.
  *C12N 5/0775* (2010.01)
  *A61K 35/48* (2015.01)

(52) U.S. Cl.
  CPC .......... *C12N 5/0662* (2013.01); *A61K 35/48* (2013.01); *C12N 2506/243* (2013.01)

(58) Field of Classification Search
  CPC . C12N 5/0662; C12N 2506/243; A61K 35/48
  See application file for complete search history.

(56) References Cited

U.S. PATENT DOCUMENTS

2016/0000835 A1  1/2016  Vizoso Pineiro et al.
2023/0227784 A1  7/2023  Black et al.

FOREIGN PATENT DOCUMENTS

WO    2021226373 A2    11/2021

OTHER PUBLICATIONS

Schlafer (Reprod Dom Anim 47 (Suppl. 6), 318-322 (2012)).*
Nisolle (Fertility and Sterility, 64:1, 69-75, 1995).*
Moller (Reprod Dom Anim 47 (Suppl. 6), 318-322 (2012)).*
Dittrich (Horm Metab Res 2006; 38: 141-145).*
International Search Report and Written Opinion for International PCT Application No. PCT/US2021/031148 dated Nov. 5, 2021, 12 pages.
Stewart, Allison A. et al., "Effect of fibroblast growth factor-2 on equine mesenchymal stem cell monolayer expansion and chondrogenesis" AJVR, Sep. 2007, pp. 941-945, vol. 68, No. 9.
International Preliminary Report on Patentability for International PCT Application No. PCT/US2021/031148 dated Nov. 8, 2022, 8 pages.
As Vidane et al: "Transplantation of amniotic membrane-derived multipotent cells ameliorates and delays the progression of chronic kidney disease in cats", Reproduction in Domestic Animals, vol. 52, Oct. 23, 2016 pp. 316-326.
Gargett Caroline E. et al: "Isolation and Culture of Epithelial Progenitors and Mesenchymal Stem Cells from Human Endometrium", Biology of Reproduction, vol. 80, No. 6, Feb. 18, 2009 (Feb. 18, 2009), pp. 1136-1145.
Sahoo A. K. et al: "Isolation, culture, characterization, and osteogenic differentiation of canine endometrial mesenchymal stem cell", Veterinary World, vol. 10, No. 12, Dec. 1, 2017 (Dec. 1, 2017), pp. 1533-1541.
U.S. Appl. No. 17/997,861, filed Nov. 3, 2022, Linda Black et al.

* cited by examiner

*Primary Examiner* — Valerie E Bertoglio
(74) *Attorney, Agent, or Firm* — Goodwin Procter LLP

(57) ABSTRACT

The present disclosure relates to heterogeneous cell compositions derived from canine or feline uterine tissue and methods of producing and use thereof. In some aspects, the heterogeneous cell compositions comprise a mixture of mesenchymal progenitor cells and epithelial progenitor cells. In some aspects, the heterogeneous cell compositions are used as an autologous or allogeneic treatment for the treatment of diseases such as chronic kidney disease, atopic dermatitis, immune mediated arthritis, hepatitis, liver disease, inflammatory bowel disease, osteoarthritis, intravertebral disc disease, keratoconjunctivitis sicca (dry eye), pancreatitis, fibrosis, sclerosis, amyloidosis, immune mediated polyarthritis or wounds in canines and felines.

20 Claims, 26 Drawing Sheets

Live/dead
(Donor G0313)

| | Protocol A | Protocol B |
|---|---|---|
| PCF |  % live cells 34.1 |  % live cells 46.7 |
| Day 3<br>(not enough sample of Day 4 for either A or B) | no sample |  % live cells 44.6 |

FSC-A

IOHEXOL CLEARANCE RESULTS

| Group No. & Treatment | Date: | 01-OCT-2015 | 19-OCT-2015 | 03-NOV-2015 | 02-DEC-2015 | 13-JAN-2016 | 04-FEB-2016 | 04-MAR-2016 | 04-APR-2016 |
|---|---|---|---|---|---|---|---|---|---|
| | Study Day | -5 | 13 | 28 | 57 | 99 | 121 | 150 | 182 |
| | Animal No. | | | | (mL/min/kg) | | | | |
| 1 Allogeneic Feline Uterine-derived regenerative cells | 70892 | 0.717 | 1.000 | 0.954 | 1.179 | 1.123 | 1.206 | 0.777 | 0.829 |
| | 05862 | 0.599 | 0.792 | 0.733 | 0.911 | 0.825 | - | - | - |
| | 06363 | 1.133 | 1.118 | 1.494 | 1.201 | 1.032 | 1.231 | 1.214 | 1.487 |
| | 84286 | 1.073 | 1.364 | 1.463 | 1.519 | 0.757 | 1.386 | 1.104 | 1.649 |
| | 94591 | 1.008 | 1.570 | 1.457 | 1.395 | 1.610 | 1.259 | 1.128 | 0.775 |
| | 66845 | 0.961 | 1.015 | 0.685 | 0.768 | 1.194 | 0.706 | 0.597 | 0.584 |
| | 77069 | 0.978 | 0.963 | 0.891 | 1.046 | 0.943 | 0.894 | 0.738 | 0.411 |
| | 83523 | 1.023 | 1.367 | 2.101 | 1.347 | 1.307 | 1.129 | 1.216 | 1.289 |
| | 24120 | 1.407 | 1.771 | 2.268 | 1.788 | 1.389 | 1.926 | 2.389 | 1.912 |
| | 20815 | 0.927 | 1.009 | 1.188 | 1.433 | 0.855 | 1.130 | 0.982 | 1.09 |
| | 36874 | 1.300 | 1.632 | 1.988 | 1.920 | 1.785 | 1.434 | 1.946 | 1.546 |
| | 04028 | 1.535 | 2.236 | 2.306 | 2.885 | 1.946 | 2.318 | 1.924 | 1.824 |
| | 58261 | 1.504 | 1.929 | 2.083 | 2.078 | NR | 2.035 | 1.565 | 2.287 |
| | 25369 | 1.412 | 1.758 | 2.135 | 1.870 | 2.087 | 1.446 | 1.248 | 1.147 |
| | 96068 | 1.883 | 2.545 | 2.458 | 2.813 | 2.820 | 1.965 | 1.734 | 2.394 |
| | 27613 | 0.823 | 1.098 | 1.088 | 1.304 | 1.085 | 0.867 | 0.792 | 0.754 |
| | 61586 | 0.885 | 0.991 | 1.063 | 1.403 | 1.328 | 0.819 | 0.812 | 0.949 |
| | 72624 | 0.989 | 1.347 | 1.425 | 1.736 | 1.034 | 1.372 | 1.360 | 1.341 |

NR = no result (slope couldn't be calculated)
- = No sample collected as animal died on Study Day 120

RMANCOVA model for iohexol clearance

| Response | Transf. | p-values for model effects day | baseline | p-value for normality |
|---|---|---|---|---|
| Iohexol clearance | 1 | 0.0059 | <.0001 | 0.3648 |

RMANCOVA estimates and p-values for iohexol clearance

| Response | Day | Model estimates and std. error observed | change from baseline | p-value |
|---|---|---|---|---|
| Iohexol clearance | -5 | 1.108 (0.071) | n.v. | n.v. |
| | 13 | 1.432 (0.067) | 0.314 (0.067) | <.0001 I |
| | 28 | 1.558 (0.067) | 0.440 (0.067) | <.0001 I |
| | 57 | 1.609 (0.067) | 0.491 (0.067) | <.0001 I |
| | 99 | 1.411 (0.069) | 0.293 (0.069) | <.0001 I |
| | 121 | 1.328 (0.069) | 0.210 (0.069) | 0.0029 I |
| | 150 | 1.235 (0.069) | 0.117 (0.069) | 0.0925 |
| | 182 | 1.278 (0.069) | 0.160 (0.069) | 0.0225 I |

Next to each significant comparison, the direction of significance is indicated (D=decrease, I=increase)

Figure 10

BODYWEIGHT DATA

| Group No. & Treatment | Animal No. | Sex | Bodyweight (kg) Study Day | | | | | |
|---|---|---|---|---|---|---|---|---|
| | | | -7 | 57 | 92 | 112 | 140 | 168 |
| 1 Allogeneic, Feline Uterine-derived regenerative cells | 70892 | Female | 2.6 | 2.7 | 2.7 | 2.8 | 2.7 | 2.8 |
| | 05882 | Female | 5.2 | 5.1 | 5.2 | 5.5 | N/A | N/A |
| | 06363 | Female | 2.9 | 3.2 | 3.4 | 3.3 | 3.2 | 3.1 |
| | 64280 | Female | 3.9 | 3.6 | 3.9 | 4.0 | 4.0 | 4.1 |
| | 94591 | Female | 2.9 | 3.4 | 3.2 | 3.3 | 3.1 | 3.2 |
| | 66845 | Female | 5.6 | 4.7 | 4.9 | 4.9 | 5.0 | 4.8 |
| | 77069 | Female | 2.7 | 2.7 | 2.7 | 2.8 | 2.8 | 2.8 |
| | 83523 | Female | 3.9 | 4.0 | 4.1 | 4.1 | 3.9 | 3.9 |
| | 24120 | Female | 2.8 | 2.8 | 2.9 | 2.8 | 2.6 | 2.7 |
| | 20815 | Female | 2.8 | 2.5 | 2.6 | 2.6 | 2.4 | 2.4 |
| | 36874 | Female | 3.0 | 3.2 | 3.2 | 3.3 | 3.3 | 3.2 |
| | 04028 | Female | 3.1 | 2.9 | 2.9 | 2.9 | 3.1 | 3.1 |
| | 58261 | Female | 4.0 | 3.8 | 3.9 | 4.0 | 3.8 | 3.8 |
| | 25369 | Female | 4.3 | 4.3 | 4.4 | 4.4 | 4.5 | 4.3 |
| | 96068 | Female | 3.1 | 3.2 | 3.2 | 3.3 | 3.2 | 3.3 |
| | 27613 | Male | 4.8 | 5.0 | 5.2 | 5.4 | 5.1 | 5.3 |
| | 61586 | Male | 4.1 | 4.1 | 4.2 | 4.5 | 4.3 | 4.4 |
| | 72624 | Male | 4.9 | 4.6 | 4.6 | 5.0 | 4.7 | 4.6 |
| | Mean | | 3.7 | 3.7 | 3.7 | 3.8 | 3.6 | 3.6 |
| | St. Dev. | | 0.96 | 0.83 | 0.88 | 0.95 | 0.86 | 0.84 |

Mean (arithmetic) and Standard Deviation (St. Dev.) calculated using Microsoft® Excel
N/A =Not applicable

Figure 11

RMANCOVA model for body weight

| Response | Transf. | p-values for model effects day | baseline | p-value for normality |
|---|---|---|---|---|
| Body weight | 1 | 0.0003 | <.0001 | 0.1913 |

RMANCOVA estimates and p-values for body weight

| Response | Day | Model estimates and std. error observed | change from baseline | p-value |
|---|---|---|---|---|
| | -7 | 3.70 (0.23) | n.v. | n.v. |
| | 57 | 3.63 (0.07) | -0.04 (0.07) | 0.5534 |
| | 92 | 3.70 (0.07) | 0.04 (0.07) | 0.5768 |
| Body weight | 112 | 3.80 (0.07) | 0.13 (0.07) | 0.0596 |
| | 140 | 3.70 (0.07) | 0.03 (0.07) | 0.6588 |
| | 168 | 3.70 (0.07) | 0.03 (0.07) | 0.6194 |

Next to each significant comparison, the direction of significance is indicated (D=decrease, I=increase)

RMANCOVA models for urinalysis parameters

| Response | Transf. | p-values for model effects day | p-values for model effects baseline | p-value for normality |
|---|---|---|---|---|
| Urine specific gravity | 1 | <.0001 | <.0001 | 0.4041 |
| Urine protein | 1 | 0.1543 | 0.4684 | <.0001 |
| Urine creatinine | 1 | <.0001 | <.0001 | 0.3260 |
| Urine protein/creatinine ratio | 1 | 0.3758 | <.0001 | <.0001 |

RMANCOVA estimates and p-values for urinalysis parameters

| Response | Day | Model estimates and std. error observed | Model estimates and std. error change from baseline | p-value |
|---|---|---|---|---|
| Urine specific gravity | -7 | 1.026 (0.002) | n.v. | n.v. |
| | 7 | 1.026 (0.001) | -0.000 (0.001) | 0.8167 |
| | 13 | 1.021 (0.001) | -0.006 (0.001) | <.0001 D |
| | 28 | 1.026 (0.001) | -0.001 (0.001) | 0.5172 |
| | 56 | 1.027 (0.001) | 0.001 (0.001) | 0.6112 |
| | 97 | 1.025 (0.001) | -0.002 (0.001) | 0.1971 |
| | 120 | 1.026 (0.001) | -0.001 (0.001) | 0.4594 |
| | 149 | 1.027 (0.001) | -0.000 (0.001) | 0.9787 |
| | 181 | 1.028 (0.001) | 0.001 (0.001) | 0.4685 |
| Urine protein | -7 | 0.348 (0.042) | n.v. | n.v. |
| | 7 | 0.284 (0.081) | -0.064 (0.081) | 0.4345 |
| | 13 | 0.226 (0.081) | -0.122 (0.081) | 0.1372 |
| | 28 | 0.387 (0.081) | 0.038 (0.081) | 0.6364 |
| | 56 | 0.429 (0.081) | 0.081 (0.081) | 0.3198 |
| | 97 | 0.410 (0.081) | 0.062 (0.081) | 0.4443 |
| | 120 | 0.390 (0.081) | 0.042 (0.081) | 0.6075 |
| | 149 | 0.467 (0.082) | 0.119 (0.082) | 0.1531 |
| | 181 | 0.543 (0.083) | 0.195 (0.083) | 0.0221 I |
| Urine creatinine | -7 | 18295 (2001) | n.v. | n.v. |
| | 7 | 15651 (1082) | -2817 (1082) | 0.0109 D |
| | 13 | 9468 (1082) | -9000 (1082) | <.0001 D |
| | 28 | 14806 (1082) | -3662 (1082) | 0.0011 D |
| | 56 | 16089 (1082) | -2379 (1082) | 0.0306 D |
| | 97 | 15823 (1082) | -2645 (1082) | 0.0165 D |
| | 120 | 14959 (1082) | -3509 (1082) | 0.0017 D |
| | 149 | 16392 (1107) | -2076 (1107) | 0.0640 |
| | 181 | 15896 (1113) | -2572 (1113) | 0.0232 D |
| Urine protein/creatinine ratio | -7 | 0.214 (0.056) | n.v. | n.v. |
| | 7 | 0.201 (0.053) | -0.012 (0.053) | 0.8204 |
| | 13 | 0.227 (0.053) | 0.014 (0.053) | 0.7880 |
| | 28 | 0.286 (0.053) | 0.073 (0.053) | 0.1717 |
| | 56 | 0.315 (0.053) | 0.102 (0.053) | 0.0592 |
| | 97 | 0.290 (0.053) | 0.077 (0.053) | 0.1501 |
| | 120 | 0.319 (0.053) | 0.106 (0.053) | 0.0491 I |
| | 149 | 0.329 (0.054) | 0.116 (0.054) | 0.0344 I |
| | 181 | 0.381 (0.054) | 0.169 (0.054) | 0.0028 I |

Next to each significant comparison, the direction of significance is indicated (D=decrease, I=increase)

Figure 12 cont.

| Donor Identification (Passage Number) | Control Medium Incubation | Induction Medium Incubation |
|---|---|---|
| Feline S-003 (P5) (images are 20X) |  |  |
| Canine | |  |

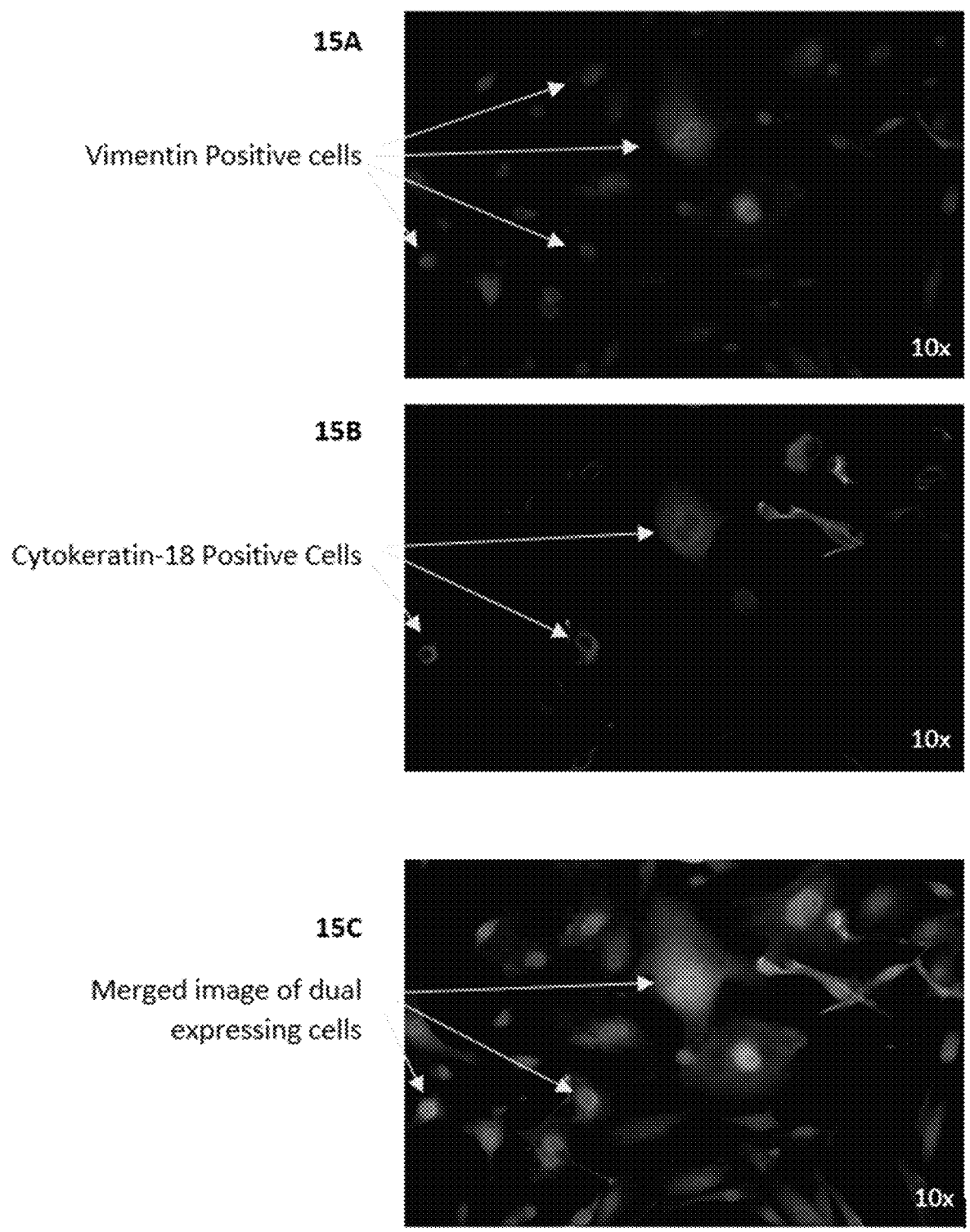
Figure 15A-C

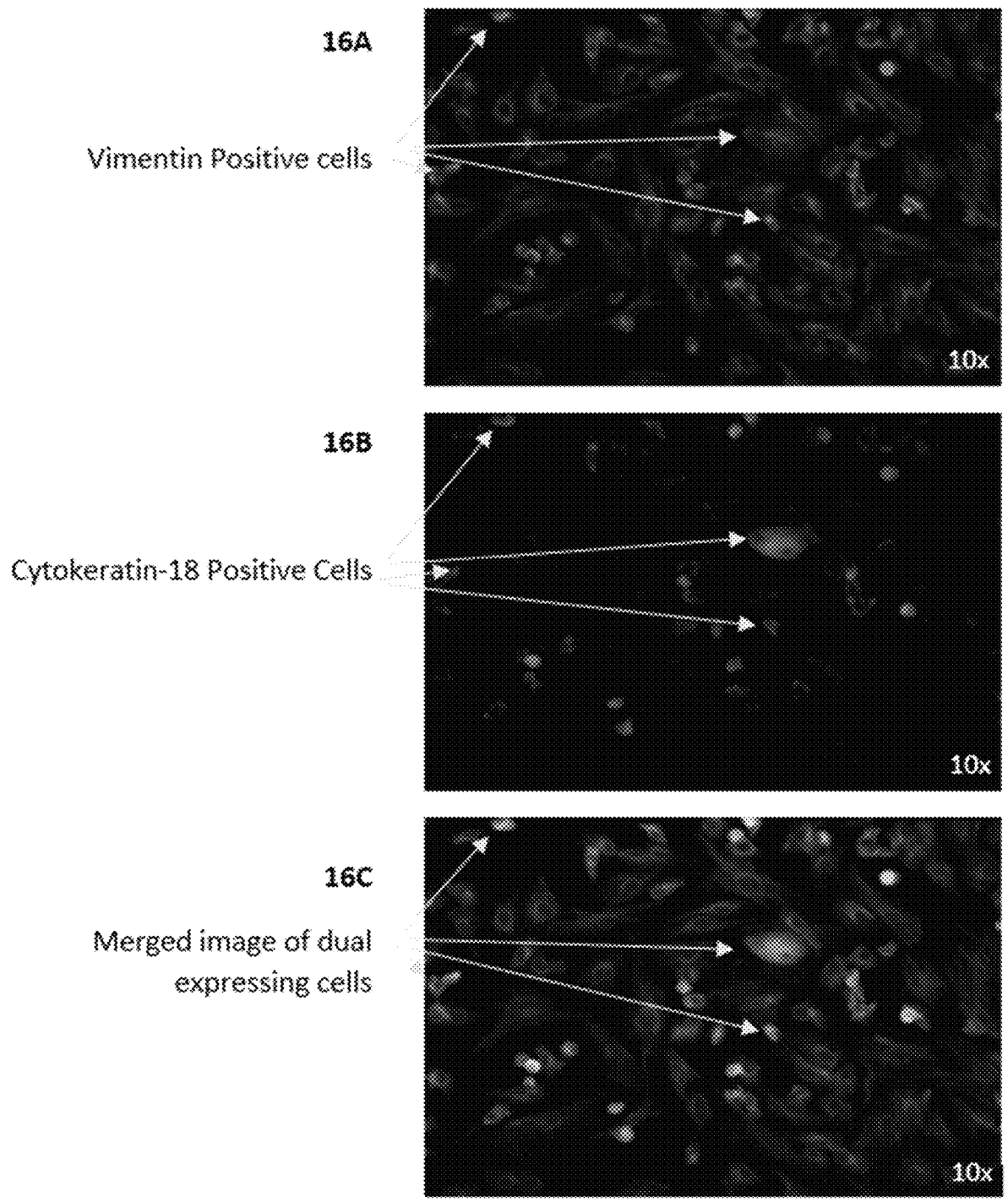
Figure 16A-C

UTERINE-DERIVED REGENERATIVE CELL COMPOSITIONS AND USES THEREOF

CROSS-REFERENCE TO RELATED APPLICATIONS

This application is a U.S. continuation of non-provisional application Ser. No. 17/997,861, filed on Nov. 3, 2022, which is a National Phase Application of PCT International Application Number PCT/US2021/031148, filed on May 6, 2021, designating the United States of America and published in the English language, which is an International Application of and claims the benefit of priority to U.S. Provisional Application No. 63/022,302, filed on May 8, 2020, which are hereby expressly incorporated by reference in their entireties.

FIELD

The present disclosure relates to cell compositions derived from canine or feline uterine tissue and methods of producing the same and uses thereof. In some aspects, a heterogeneous cell composition comprises a mixture of mesenchymal progenitor cells and epithelial progenitor cells. In additional aspects, the cell compositions such as the aforementioned heterogeneous cell composition are used in an autologous or allogeneic therapy for the treatment, inhibition, or amelioration of diseases including chronic kidney disease, atopic dermatitis, immune mediated arthritis, hepatitis, liver disease, inflammatory bowel disease, osteoarthritis, intravertebral disc disease, keratoconjunctivitis sicca (dry eye), pancreatitis, fibrosis, sclerosis, amyloidosis, immune mediated polyarthritis, or wounds in canines and felines.

BACKGROUND

Degenerative diseases associated with inflammation and aging can cause significant pain or discomfort in geriatric animals. For pet owners, that translates into an emotional and potentially monetary burden, should they choose to pursue therapeutic or palliative interventions. However, for many degenerative diseases, only symptomatic or overly invasive treatments are available. For example, chronic kidney disease (CKD) is a leading cause of mortality in domestic cats, but save for a costly kidney transplant, there are no currently available treatments that reverse the functional capacity of the failing kidney in these animals. As another example, atopic dermatitis is one of the most common skin disorders affecting canines, resulting in persistent pruritus. Therefore, there is a lasting need for effective, inexpensive, and non-invasive therapies for CKD, atopic dermatitis, and other inflammatory and/or degenerative diseases for pets and other animals, such as canines and felines.

SUMMARY

Disclosed herein in some embodiments are cell compositions. In some embodiments, these cell compositions comprise a population of mesenchymal progenitor cells. In some embodiments, these cell compositions are heterogeneous and further comprise a population of epithelial progenitor cells. In some embodiments, the mesenchymal progenitor cells and epithelial progenitor cells are co-cultured. In some embodiments, the mesenchymal progenitor cells and epithelial progenitor cells are obtained or derived from uterine tissue. In some embodiments, the uterine tissue is canine or feline uterine tissue. In some embodiments, the mesenchymal progenitor cells and epithelial progenitor cells are respectively present in the composition in a ratio of 1% to 99%, 2% to 98%, 3% to 97%, 4% to 96%, 5% to 95%, 10% to 90%, 20% to 80%, 30% to 70%, 40% to 60%, 50% to 50%, 60% to 40%, 70% to 30%, 80% to 20%, 90% to 10%, 95% to 5%, 96% to 4%, 97% to 3%, 98% to 2%, or 99% to 1% or about 1% to about 99%, about 2% to about 98%, about 3% to about 97%, about 4% to about 96%, about 5% to about 95%, about 10% to about 90%, about 20% to about 80%, about 30% to about 70%, about 40% to about 60%, about 50% to about 50%, about 60% to about 40%, about 70% to about 30%, about 80% to about 20%, about 90% to about 10%, about 95% to about 5%, about 96% to about 4%, about 97% to about 3%, about 98% to about 2%, or about 99% to about 1%, or any ratio within a range defined by any two of the aforementioned percentages. In some embodiments, the mesenchymal progenitor cells and epithelial progenitor cells in the composition are present in a ratio of 20% to 80%, 40% to 60%, 50% to 50%, 60% to 40%, 80% to 20%, 90% to 10%, 99% to 1%, about 20% to about 80%, about 40% to about 60%, about 50% to about 50%, about 60% to about 40%, about 80% to about 20%, about 90% to about 10%, or about 99% to about 1%, or any ratio within a range defined by any two of the aforementioned percentages.

In some embodiments, the mesenchymal progenitor cells and epithelial progenitor cells are co-cultured in at least one tissue culture container that is not pre-treated with at least one biological or synthetic coating that enhances cell attachment and/or growth, including but not limited to cell-based feeder layers, polymers, proteins, polypeptides, peptides, antibodies, nucleic acids, DNA, RNA, sugars, polysaccharides, carbohydrates, lipids, poly-lysine, poly-ornithine, collagen, gelatin, fibronectin, vitronectin, laminin, elastin, tenascin, heparan sulfate, entactin, nidogen, osteopontin, extracellular matrix, basement membrane, Matrigel, hydrogel, PEI, WGA, or hyaluronic acid, or any combination thereof. In some embodiments, the mesenchymal progenitor cells and epithelial progenitor cells are co-cultured in at least one tissue culture container that is pre-treated with at least one biological or synthetic coating that enhances cell attachment and/or growth, such as cell-based feeder layers, polymers, proteins, polypeptides, peptides, antibodies, nucleic acids, DNA, RNA, sugars, polysaccharides, carbohydrates, lipids, poly-lysine, poly-ornithine, collagen, gelatin, fibronectin, vitronectin, laminin, elastin, tenascin, heparan sulfate, entactin, nidogen, osteopontin, extracellular matrix, basement membrane, Matrigel, hydrogel, PEI, WGA, or hyaluronic acid, or any combination thereof.

In some embodiments, the mesenchymal progenitor cells and epithelial progenitor cells are co-cultured in at least one tissue culture container for at least 1, 2, 3, 4, 5, 6, 7, 8, 9, or 10 passages, days, or culture intervals or a number of passages, days, or culture intervals within a range defined by any two of the aforementioned number of passages, days, or culture intervals. In some embodiments, the mesenchymal progenitor cells and epithelial progenitor cells are co-cultured in at least one tissue culture container for 3, 4, 5, or 6 passages, days, or culture intervals. In some embodiments, the mesenchymal progenitor cells and epithelial progenitor cells are co-cultured in at least one tissue culture container for at least 4 passages, days, or culture intervals.

In some embodiments, the cell composition, preferably a heterogeneous cell composition, comprises 5 million, 6 million, 7 million, 8 million, 9 million, 10 million, 11 million, 12 million, 13 million, 14 million, 15 million, 16 million, 17 million, 18 million, 19 million, 20 million, 30 million, 31 million, 32 million, 33 million, 34 million, 35 million, 36 million, 37 million, 38 million, 39 million, 40 million, 50 million, 60 million, 70 million, 80 million, 90 million, 100 million, 20-30 million, 30-40 million, 40-50 million, 50-60 million, 60-70 million, 70-80 million, 80-90 million, or 90-100 million, or about 5 million, about 6 million, about 7 million, about 8 million, about 9 million, about 10 million, about 11 million, about 12 million, about 13 million, about 14 million, about 15 million, about 16 million, about 17 million, about 18 million, about 19 million, about 20 million, about 30 million, about 31 million cells, about 32 million cells, about 33 million cells, about 34 million cells, about 35 million cells, about 36 million cells, about 37 million cells, about 38 million cells, about 39 million cells, about 40 million, about 50 million, about 60 million, about 70 million, about 80 million, about 90 million, about 100 million, about 20-30 million, about 30-40 million, about 40-50 million, about 50-60 million, about 60-70 million, about 70-80 million, about 80-90 million, or about 90-100 million mesenchymal progenitor cells, or any number of cells within a range defined by any two of the aforementioned numbers.

In some embodiments, the cell composition, preferably a heterogeneous cell composition, comprises 5 million, 6 million, 7 million, 8 million, 9 million, 10 million, 11 million, 12 million, 13 million, 14 million, 15 million, 16 million, 17 million, 18 million, 19 million, 20 million, 30 million, 31 million, 32 million, 33 million, 34 million, 35 million, 36 million, 37 million, 38 million, 39 million 40 million, 50 million, 60 million, 70 million, 80 million, 90 million, 100 million, 20-30 million, 30-40 million, 40-50 million, 50-60 million, 60-70 million, 70-80 million, 80-90 million, or 90-100 million, or about 5 million, about 6 million, about 7 million, about 8 million, about 9 million, about 10 million, about 11 million, about 12 million, about 13 million, about 14 million, about 15 million, about 16 million, about 17 million, about 18 million, about 19 million, about 20 million, about 30 million, about 31 million, about 32 million, about 33 million, about 34 million, about 35 million, about 36 million, about 37 million, about 38 million, about 39 million, about 40 million, about 50 million, about 60 million, about 70 million, about 80 million, about 90 million, about 100 million, about 20 to 30 million, about 30-40 million, about 40-50 million, about 50-60 million, about 60-70 million, about 70-80 million, about 80-90 million, or about 90-100 million epithelial progenitor cells, or any number of cells within a range defined by any two of the aforementioned numbers.

In some embodiments, the cell composition, preferably a heterogeneous cell composition, comprises a population of cells exhibiting both mesenchymal progenitor cell and epithelial progenitor cell markers or properties. In some embodiments, the cell composition, preferably a heterogeneous cell composition, comprises a population of cells, wherein each cell exhibits both mesenchymal progenitor cell and epithelial progenitor cell markers or properties.

In some embodiments, the mesenchymal progenitor cells and epithelial progenitor cells are obtained or derived from the same uterine tissue. In some embodiments, the mesenchymal progenitor cells and epithelial progenitor cells are obtained or derived from the same canine or feline uterine tissue. In some embodiments, the mesenchymal progenitor cells and epithelial progenitor cells are obtained or derived from different uterine tissue, such as from different feline or canine animals.

In some embodiments, the cell composition, preferably a heterogeneous cell composition, comprises a population of vimentin-positive (V+)/cytokeratin-negative (C−) cells. In some embodiments, these cell compositions, preferably heterogeneous cell compositions further comprise a population of V+/cytokeratin-positive (C+) cells. In some embodiments, the V+/C− cells and V+/C+ cells are co-cultured. In some embodiments, the V+/C− cells and V+/C+ cells are obtained or derived from uterine tissue. In some embodiments, the uterine tissue is canine or feline uterine tissue. In some embodiments, the V+/C− cells and V+/C+ cells are present in the composition in a ratio of 1% to 99%, 2% to 98%, 3% to 97%, 4% to 96%, 5% to 95%, 10% to 90%, 20% to 80%, 30% to 70%, 40% to 60%, 50% to 50%, 60% to 40%, 70% to 30%, 80% to 20%, 90% to 10%, 95% to 5%, 96% to 4%, 97% to 3%, 98% to 2%, or 99% to 1% or about 1% to about 99%, about 2% to about 98%, about 3% to about 97%, about 4% to about 96%, about 5% to about 95%, about 10% to about 90%, about 20% to about 80%, about 30% to about 70%, about 40% to about 60%, about 50% to about 50%, about 60% to about 40%, about 70% to about 30%, about 80% to about 20%, about 90% to about 10%, about 95 to about 5%, about 96% to about 4%, about 97% to about 3%, about 98% to about 2%, or about 99% to about 1%, or any ratio within a range defined by any two of the aforementioned percentages. In some embodiments, the V+/C− cells and V+/C+ cells are present in the composition in a ratio of 20% to 80%, 40% to 60%, 50% to 50%, 60% to 40%, 80% to 20%, 90% to 10%, 99% to 1%, about 20% to about 80%, about 40% to about 60%, about 50% to about 50%, about 60% to about 40%, about 80% to about 20%, about 90% to about 10%, or about 99% to about 1%, or any ratio within a range defined by any two of the aforementioned percentages.

In some embodiments, the V+/C− cells and V+/C+ cells are co-cultured in at least one tissue culture container that is not pre-treated with at least one biological or synthetic coating that enhances cell attachment and/or growth, including but not limited to cell-based feeder layers, polymers, proteins, polypeptides, peptides, antibodies, nucleic acids, DNA, RNA, sugars, polysaccharides, carbohydrates, lipids, poly-lysine, poly-ornithine, collagen, gelatin, fibronectin, vitronectin, laminin, elastin, tenascin, heparan sulfate, entactin, nidogen, osteopontin, extracellular matrix, basement membrane, Matrigel, hydrogel, PEI, WGA, or hyaluronic acid, or any combination thereof. In some embodiments, the V+/C− cells and V+/C+ cells are co-cultured in at least one tissue culture container that is pre-treated with at least one biological or synthetic coating that enhances cell attachment and/or growth such as cell-based feeder layers, polymers, proteins, polypeptides, peptides, antibodies, nucleic acids, DNA, RNA, sugars, polysaccharides, carbohydrates, lipids, poly-lysine, poly-ornithine, collagen, gelatin, fibronectin, vitronectin, laminin, elastin, tenascin, heparan sulfate, entactin, nidogen, osteopontin, extracellular matrix, basement membrane, Matrigel, hydrogel, PEI, WGA, or hyaluronic acid, or any combination thereof.

In some embodiments, the V+/C− cells and V+/C+ cells are co-cultured in at least one tissue culture container for 1, 2, 3, 4, 5, 6, 7, 8, 9, or 10 passages, days, or culture intervals or a number of passages, days, or culture intervals within a range defined by any two of the aforementioned number of passages, days, or culture intervals. In some embodiments, the V+/C− cells and V+/C+ cells are co-cultured in at least one tissue culture container for 3, 4, 5, or 6 passages, days, or culture intervals. In some embodiments, the V+/C− cells and V+/C+ cells are co-cultured in at least one tissue culture container for at least 4 passages, days, or culture intervals.

In some embodiments, the cell composition, preferably a heterogeneous cell composition, comprises 5 million, 6 million, 7 million, 8 million, 9 million, 10 million, 11 million, 12 million, 13 million, 14 million, 15 million, 16 million, 17 million, 18 million, 19 million, 20 million, 30 million, 31 million, 32 million, 33 million, 34 million, 35 million, 36 million, 37 million, 38 million, 39 million, 40 million, 50 million, 60 million, 70 million, 80 million, 90 million, 100 million, 20-30 million, 30-40 million, 40-50 million, 50-60 million, 60-70 million, 70-80 million, 80-90 million, or 90-100 million, or about 5 million, about 6 million, about 7 million, about 8 million, about 9 million, about 10 million, about 11 million, about 12 million, about 13 million, about 14 million, about 15 million, about 16 million, about 17 million, about 18 million, about 19 million, about 20 million, about 30 million, about 31 million, about 32 million, about 33 million, about 34 million, about 35 million, about 36 million, about 37 million, about 38 million, about 39 million, about 40 million, about 50 million, about 60 million, about 70 million, about 80 million, about 90 million, about 100 million, about 20 to 30 million, about 30-40 million, about 40-50 million, about 50-60 million, about 60-70 million, about 70-80 million, about 80-90 million, or about 90-100 million V+/C− cells, or any number of cells within a range defined by any two of the aforementioned numbers.

In some embodiments, cell composition, preferably a heterogeneous cell composition, comprises 5 million, 6 million, 7 million, 8 million, 9 million, 10 million, 11 million, 12 million, 13 million, 14 million, 15 million, 16 million, 17 million, 18 million, 19 million, 20 million, 30 million, 40 million, 50 million, 60 million, 70 million, 80 million, 90 million, 100 million, 20-30 million, 30-40 million, 40-50 million, 50-60 million, 60-70 million, 70-80 million, 80-90 million, or 90-100 million, or about 5 million, about 6 million, about 7 million, about 8 million, about 9 million, about 10 million, about 11 million, about 12 million, about 13 million, about 14 million, about 15 million, about 16 million, about 17 million, about 18 million, about 19 million, about 20 million, about 30 million, about 40 million, about 50 million, about 60 million, about 70 million, about 80 million, about 90 million, about 100 million, about 20 to 30 million, about 30-40 million, about 40-50 million, about 50-60 million, about 60-70 million, about 70-80 million, about 80-90 million, or about 90-100 million V+/C+ cells, or any number of cells within a range defined by any two of the aforementioned numbers.

In some embodiments, the cell composition, preferably a heterogeneous cell composition, comprises a population of cells exhibiting both V+/C− cell and V+/C+ cell markers or properties.

In some embodiments, the V+/C− cells and V+/C+ cells are obtained or derived from the same uterine tissue. In some embodiments, the V+/C− cells and V+/C+ cells are obtained or derived from the same canine or feline uterine tissue. In some embodiments, the V+/C− cells and V+/C+ cells are obtained or derived from different uterine tissue, such as from different feline or canine animals.

In some embodiments, the cell compositions, preferably heterogeneous cell compositions, further comprise an amount of fibroblast growth factor (FGF). In some embodiments, the fibroblast growth factor is fibroblast growth factor 2 (FGF-2). In some embodiments, the FGF is recombinantly produced. In some embodiments, the FGF is a human FGF. In some embodiments, the FGF is human FGF-2. In some embodiments, the FGF is recombinant human FGF-2. In some embodiments, the FGF, preferably human FGF-2, is present in a concentration of 0.01, 0.05, 0.1, 1, 2, 3, 4, 5, 6, 7, 8, 9, 10, 15, 20, 30, 40, 50, 60, 70, 80, 90, or 100 ng/mL or at a concentration within a range defined by any two of the aforementioned concentrations. In some embodiments, the FGF is present in a concentration of 0.1, 0.5, 1, 2, 3, 4, 5, 6, 7, 8, 9, or 10 ng/mL or at a concentration within a range defined by any two of the aforementioned concentrations. In some embodiments, the FGF is present at a concentration of 8 ng/mL.

In some embodiments, the uterine tissue is obtained from a spay procedure.

In some embodiments, the cell composition, preferably a heterogeneous cell composition, further comprises at least one additive, antibiotic, supplement, vitamin, growth factor, cryoprotectant, buffer, salt, protein, polypeptide, peptide, sugar, polysaccharide, or carbohydrate including but not limited to trehalose, DMSO, or albumin, or any combination thereof.

In some embodiments, the cell composition, preferably a heterogeneous cell composition, further comprises a cryopreservation medium. In some embodiments, the cryopreservation medium comprises CryoStor CS5; BioLife Solutions CS10; 98% Hespan and 2% DMSO; about 98% Hespan and about 2% DMSO; 2-10% DMSO and 2-20% FCS in a growth medium; or about 2-10% DMSO and about 2-20% FCS in a growth medium.

Disclosed herein in some embodiments are methods of preparing a cell composition, preferably a heterogeneous cell composition. Exemplary methods comprise contacting a single or heterogenous cell suspension comprising mesenchymal progenitor cells and epithelial progenitor cells with FGF-2; and culturing the single or heterogenous cell suspension with FGF-2 for 3, 4, 5, or 6 passages, days, or culture intervals. In some embodiments, the single or heterogenous cell suspension is cultured for at least 4 passages, days, or culture intervals. In some embodiments, the cells used to generate the single or heterogenous cell suspension are obtained or derived from uterine tissue. In some embodiments, the cells used to generate the single or heterogenous cell suspension are obtained or derived from canine or feline uterine tissue. In some embodiments, the cells used to generate the single or heterogenous cell suspension are obtained or derived from the same canine or feline uterine tissue.

In some embodiments, at the end of 3, 4, 5 or 6 passages, days, or culture intervals, the mesenchymal progenitor cells and epithelial progenitor cells are present in the composition in a ratio of 1% to 99%, 2% to 98%, 3% to 97%, 4% to 96%, 5% to 95%, 10% to 90%, 20% to 80%, 30% to 70%, 40% to 60%, 50% to 50%, 60% to 40%, 70% to 30%, 80% to 20%, 90% to 10%, 95 to 5%, 96% to 4%, 97% to 3%, 98% to 2%, 99% to 1%, or about 1% to about 99%, about 2% to about 98%, about 3% to about 97%, about 4% to about 96%, about 5% to about 95%, about 10% to about 90%, about 20% to about 80%, about 30% to about 70%, about 40% to about 60%, about 50% to about 50%, about 60% to about 40%, about 70% to about 30%, about 80% to about 20%, about 90% to about 10%, about 95 to about 5%, about 96% to about 4%, about 97% to about 3%, about 98% to about 2%, or about 99% to about 1%, or at a ratio within a range defined by any two of the aforementioned percentages. In some embodiments, at the end of 3, 4, 5, or 6 passages, days, or culture intervals, the mesenchymal progenitor cells and epithelial progenitor cells are present in a ratio of 20% to 80%, 40% to 60%, 50% to 50%, 60% to 40%, 80% to 20%, 90% to 10%, 99% to 1%, or about 20% to about 80%, about 40% to about 60%, about 50% to about 50%, about 60% to about 40%, about 80% to about 20%, about 90% to about 10%, or about 99% to about 1%, or at a ratio within a range defined by any two of the aforementioned ratios.

More embodiments concern methods of preparing a cell composition, preferably a heterogeneous cell composition. In some embodiments, the methods comprise contacting a single cell suspension comprising V+/C− cells and V+/C+ cells with FGF-2; and culturing the single cell suspension with FGF-2 for 3, 4, 5, or 6 passages, days, or culture intervals. In some embodiments, the single cell suspension is cultured for at least 4 passages, days, or culture intervals. In some embodiments, the cells of the single cell suspension are obtained or derived from uterine tissue. In some embodiments, the cells of the single cell suspension are obtained or derived from canine or feline uterine tissue. In some embodiments, the cells of the single cell suspension are obtained or derived from the same canine or feline uterine tissue. In some embodiments, the cells of the single cell suspension are obtained or derived from different canine or feline uterine tissue.

In some embodiments, at the end of 3, 4, 5 or 6 passages, days, or culture intervals, the V+/C− cells and V+/C+ cells are present in a ratio of 1% to 99%, 2% to 98%, 3% to 97%, 4% to 96%, 5% to 95%, 10% to 90%, 20% to 80%, 30% to 70%, 40% to 60%, 50% to 50%, 60% to 40%, 70% to 30%, 80% to 20%, 90% to 10%, 95% to 5%, 96% to 4%, 97% to 3%, 98% to 2%, or 99% to 1% or about 1% to about 99%, about 2% to about 98%, about 3% to about 97%, about 4% to about 96%, or about 5% to about 95%, about 10% to about 90%, about 20% to about 80%, about 30% to about 70%, about 40% to about 60%, about 50% to about 50%, about 60% to about 40%, about 70% to about 30%, about 80% to about 20%, about 90% to about 10%, about 95 to about 5%, about 96% to about 4%, about 97% to about 3%, about 98% to about 2%, or about 99% to about 1%, or at a ratio within a range defined by any two of the aforementioned ratios. In some embodiments, at the end of 3, 4, 5, or 6 passages, days, or culture intervals, the V+/C− cells and V+/C+ cells are in a ratio of 20% to 80%, 40% to 60%, 50% to 50%, 60% to 40%, 80% to 20%, 90% to 10%, or 99% to 1%, or about 20% to about 80%, about 40% to about 60%, about 50% to about 50%, about 60% to about 40%, about 80% to about 20%, about 90% to about 10%, or about 99% to about 1%, or any ratio within a range defined by any two of the aforementioned ratios.

In some embodiments, the uterine tissue is enzymatically dissociated to form the single cell suspension. In some embodiments, the canine or feline uterine tissue is enzymatically dissociated to form the single cell suspension.

In some embodiments, the FGF-2 is recombinantly produced. In some embodiments, the FGF-2 is human FGF-2. In some embodiments, the FGF-2 is recombinant human FGF-2. In some embodiments, the FGF-2 is present at a concentration of 0.01, 0.05, 0.1, 1, 2, 3, 4, 5, 6, 7, 8, 9, 10, 15, 20, 30, 40, 50, 60, 70, 80, 90, or 100 ng/mL or any concentration within a range defined by any two of the aforementioned concentrations. In some embodiments, the FGF-2 is present at a concentration of 0.1, 0.5, 1, 2, 3, 4, 5, 6, 7, 8, 9, or 10 ng/mL or any concentration within a range defined by any two of the aforementioned concentrations. In some embodiments, the FGF-2 is present at a concentration of 8 ng/mL.

Described herein in some embodiments are methods of treating, inhibiting, or ameliorating a disease or condition in a canine or feline subject. In some embodiments, the methods comprise providing at least one cell composition described herein, preferably a heterogeneous cell composition comprising a population of mesenchymal progenitor cells and a population of epithelial progenitor cells, and administering the at least one cell composition, preferably a heterogeneous cell composition, to the canine or feline subject. In some embodiments, the mesenchymal progenitor cells and epithelial progenitor cells are obtained or derived from canine or feline uterine tissue. In some embodiments, the canine or feline uterine tissue is autologous or allogeneic to the canine or feline subject. In some embodiments, the canine or feline uterine tissue is autologous to the canine or feline subject. In some embodiments, the canine or feline uterine tissue is allogeneic to the canine or feline subject. In some embodiments, the disease is chronic kidney disease, atopic dermatitis, immune mediated arthritis, hepatitis, liver disease, inflammatory bowel disease, osteoarthritis, intravertebral disc disease, keratoconjunctivitis sicca (dry eye), pancreatitis, fibrosis, sclerosis, amyloidosis, immune related polyarthritis, or a wound. In some of these methods, the mesenchymal progenitor cells and epithelial progenitor cells are provided in a composition having a ratio of 20% to 80%, 40% to 60%, 50% to 50%, 60% to 40%, 80% to 20%, 90% to 10%, 99% to 1%, about 20% to about 80%, about 40% to about 60%, about 50% to about 50%, about 60% to about 40%, about 80% to about 20%, about 90% to about 10%, or about 99% to about 1%, or at a ratio within a range defined by any two of the aforementioned ratios.

Additional embodiments concern methods of treating, inhibiting, or ameliorating a disease or condition in a canine or feline subject. Some of these methods comprise providing at least one cell composition, preferably a heterogeneous cell composition comprising a population of V+/C− cells and a population of V+/C+ cells and administering the at least one heterogeneous cell composition to the canine or feline subject. In some embodiments, the V+/C− cells and V+/C+ cells are obtained or derived from canine or feline uterine tissue. In some embodiments, the canine or feline uterine tissue is autologous or allogeneic to the canine or feline subject. In some embodiments, the disease is chronic kidney disease, atopic dermatitis, immune mediated arthritis, hepatitis, liver disease, inflammatory bowel disease, osteoarthritis, intravertebral disc disease, keratoconjunctivitis sicca (dry eye), pancreatitis, fibrosis, sclerosis, amyloidosis, immune mediated polyarthritis or a wound. In some of these methods, the V+/C− cells and V+/C+ cells are provided in a composition having a ratio of 20% to 80%, 40% to 60%, 50% to 50%, 60% to 40%, 80% to 20%, 90% to 10%, 99% to 1%, about 20% to about 80%, about 40% to about 60%, about 50% to about 50%, about 60% to about 40%, about 80% to about 20%, about 90% to about 10%, or about 99% to about 1%, or at a ratio within a range defined by any two of the aforementioned ratios.

In some embodiments, the at least one cell composition, preferably a heterogeneous cell composition is administered to feline or canine subjects that are preferably identified or selected to receive a progenitor cell therapy for chronic kidney disease, atopic dermatitis, immune mediated arthritis, hepatitis, liver disease, inflammatory bowel disease, osteoarthritis, intravertebral disc disease, keratoconjunctivitis sicca (dry eye), pancreatitis, fibrosis, sclerosis, amyloidosis, immune mediated polyarthritis or a wound. Such a selection or identification can be made by clinicians or veterinarians using clinical evaluation and/or diagnostics. Said feline or canine subjects that are preferably identified or selected, are then provided or administered one or more of the cell compositions provided herein enterally, parenterally, intravenously, intraarterially, subcutaneously, intramuscularly, intradermally, intrathecally, intraperitoneally, intraportally, intra-articularly, intraocularly or intrarenally, or any combination thereof. In some embodiments, the at least one heterogeneous cell composition is thawed from a cryopreserved state before administration. In some embodiments, the at least one heterogeneous cell composition is thawed from a cryopreserved state and transferred to a delivery device or container before administration. In some embodiments, the delivery device or container is a syringe, IV bag, cannula, pump, or tubing. In some embodiments, the delivery device or container comprises a suitable buffer, diluent or fluid. In some embodiments, the suitable buffer, diluent or fluid comprises saline, phosphate buffered saline, lactated Ringer's solution, Ringer's acetate solution, or dextrose solution. In some embodiments, thawing the at least one heterogeneous cell composition from the cryopreserved state comprises diluting the at least one heterogeneous cell composition by 1.5×, 2×, 3×, 4×, 5×, 6×, 7×, 8×, 9×, 10×, or at least 1.5×, 2×, 3×, 4×, 5×, 6×, 7×, 8×, 9×, or 10×. Additional embodiments concern the use of any one or more of the cell compositions described herein as a medicament, preferably for the treatment, inhibition, or amelioration of chronic kidney disease, atopic dermatitis, immune mediated arthritis, hepatitis, liver disease, inflammatory bowel disease, osteoarthritis, intravertebral disc disease, keratoconjunctivitis sicca (dry eye), pancreatitis, fibrosis, sclerosis, amyloidosis, immune mediated polyarthritis or a wound.

Embodiments provided herein preferably include the following numbered alternatives:

1. A heterogeneous cell composition comprising:
a population of mesenchymal progenitor cells; and
a population of epithelial progenitor cells;
wherein the mesenchymal progenitor cells and epithelial progenitor cells are co-cultured;
wherein the mesenchymal progenitor cells and epithelial progenitor cells are obtained or derived from canine or feline uterine tissue; and
wherein the mesenchymal progenitor cells and epithelial progenitor cells are in a ratio of 20% to 80%, 40% to 60%, 50% to 50%, 60% to 40%, 80% to 20%, about 20% to about 80%, about 40% to about 60%, about 50% to about 50%, about 60% to about 40%, or about 80% to 20%, or a ratio within a range defined by any two of the aforementioned percentages.
2. The composition of alternative 1, further comprising fibroblast growth factor 2 (FGF-2).
3. The composition of alternative 2, wherein the FGF-2 is recombinant human FGF-2.
4. The composition of alternative 2 or 3, wherein the FGF-2 is present at a concentration of 8 ng/mL.
5. The composition of any of the preceding alternatives, wherein the mesenchymal progenitor cells and epithelial progenitor cells are co-cultured in at least one tissue culture container that is not pre-treated with biological or synthetic coatings that enhance cell attachment and/or growth, including but not limited to cell-based feeder layers, polymers, proteins, polypeptides, peptides, antibodies, nucleic acids, DNA, RNA, sugars, polysaccharides, carbohydrates, lipids, poly-lysine, poly-ornithine, collagen, gelatin, fibronectin, vitronectin, laminin, elastin, tenascin, heparan sulfate, entactin, nidogen, osteopontin, extracellular matrix, basement membrane, Matrigel, hydrogel, PEI, WGA, hyaluronic acid, or any combination thereof.
6. The composition of any of the preceding alternatives, wherein the mesenchymal progenitor cells and epithelial progenitor cells are co-cultured in at least one tissue culture container for 3, 4, 5, or 6 passages, days, or culture intervals.
7. The composition of any of the preceding alternatives, wherein the uterine tissue is obtained from a spay procedure.
8. The composition of any of the preceding alternatives, comprising 5 million, 6 million, 7 million, 8 million, 9 million, 10 million, 11 million, 12 million, 13 million, 14 million, 15 million, 16 million, 17 million, 18 million, 19 million, 20 million, 30 million, 40 million, 50 million, 60 million, 70 million, 80 million, 90 million, or 100 million or about 5 million, about 6 million, about 7 million, about 8 million, about 9 million, about 10 million, about 11 million, about 12 million, about 13 million, about 14 million, about 15 million, about 16 million, about 17 million, about 18 million, about 19 million, about 20 million, about 30 million, about 40 million, about 50 million, about 60 million, about 70 million, about 80 million, about 90 million, or about 100 million mesenchymal progenitor cells, or a number mesenchymal progenitor cells within a range defined by any two of the aforementioned numbers.
9. The composition of any of the preceding alternatives, comprising 5 million, 6 million, 7 million, 8 million, 9 million, 10 million, 11 million, 12 million, 13 million, 14 million, 15 million, 16 million, 17 million, 18 million, 19 million, 20 million, 30 million, 40 million, 50 million, 60 million, 70 million, 80 million, 90 million, or 100 million or about 5 million, about 6 million, about 7 million, about 8 million, about 9 million, about 10 million, about 11 million, about 12 million, about 13 million, about 14 million, about 15 million, about 16 million, about 17 million, about 18 million, about 19 million, about 20 million, about 30 million, about 40 million, about 50 million, about 60 million, about 70 million, about 80 million, about 90 million, or about 100 million epithelial progenitor cells, or a number of epithelial progenitor cells within a range defined by any two of the aforementioned numbers.
10. The composition of any of the preceding alternatives, further comprising an additive, supplement, antibiotic, vitamin, growth factor, cryoprotectant, buffer, salt, protein, polypeptide, peptide, sugar, polysaccharide, or carbohydrate including but not limited to trehalose, DMSO, or albumin, or any combination thereof.
11. The composition of any of the preceding alternatives, further comprising a population of cells, wherein each cell exhibits both mesenchymal progenitor cell and epithelial progenitor cell markers.
12. The composition of any of the preceding alternatives, wherein the mesenchymal progenitor cells and epithelial progenitor cells are obtained or derived from the same canine or feline uterine tissue.
13. The composition of any of the preceding alternatives, further comprising a cryopreservation medium.
14. The composition of alternative 13, wherein the cryopreservation medium comprises:
(a) CryoStor CS5 and/or BioLife Solutions CS10;
(b) 98% Hespan and 2% DMSO;
(c) about 98% Hespan and about 2% DMSO;
(d) 2-10% DMSO and 2-20% FCS in a growth medium; or
(e) about 2-10% DMSO and about 2-20% FCS in a growth medium.

15. A method of preparing a heterogeneous cell composition, comprising:
contacting a single cell suspension comprising mesenchymal progenitor cells and epithelial progenitor cells with FGF-2; and
culturing the single cell suspension with FGF-2 for 3, 4, 5, or 6 passages, days, or culture intervals, wherein the single cell suspension is obtained or derived from canine or feline uterine tissue; and
wherein at the end of 3, 4, 5 or 6 passages, days, or culture intervals, the mesenchymal progenitor cells and epithelial progenitor cells are in a ratio of 20% to 80%, 40% to 60%, 50% to 50%, 60% to 40%, 80% to 20%, about 20% to about 80%, about 40% to about 60%, about 50% to about 50%, about 60% to about 40%, or about 80% to 20%, or a ratio within a range defined by any two of the aforementioned percentages.

16. The method of alternative 15, wherein the single cell suspension is obtained or derived from the same canine or feline uterine tissue.

17. The method of alternative 15 or 16, wherein the canine or feline uterine tissue is enzymatically dissociated to form the single cell suspension.

18. The method of any one of alternatives 15-17, wherein the FGF-2 is recombinant human FGF-2.

19. The method of any one of alternatives 15-18, wherein the FGF-2 is at a concentration of 8 ng/mL.

20. The method of any one of alternatives 15-19, wherein the single cell suspension is cultured for at least 4 passages, days, or culture intervals.

21. A method of treating, inhibiting, or ameliorating chronic kidney disease, atopic dermatitis, immune mediated arthritis, hepatitis, liver disease, inflammatory bowel disease, osteoarthritis, intravertebral disc disease, keratoconjunctivitis sicca (dry eye), pancreatitis, fibrosis, sclerosis, amyloidosis, immune mediated polyarthritis or wounds in a canine or feline subject in need thereof, comprising:
providing at least one heterogeneous cell composition comprising a population of mesenchymal progenitor cells and a population of epithelial progenitor cells, wherein the mesenchymal progenitor cells and epithelial progenitor cells are obtained or derived from canine or feline uterine tissue and wherein the canine or feline uterine tissue is autologous or allogeneic to the canine or feline subject; and
administering the at least one heterogeneous cell composition to the canine or feline subject.

22. The method of alternative 21, wherein the mesenchymal progenitor cells and epithelial progenitor cells are in a ratio of 20% to 80%, 40% to 60%, 50% to 50%, 60% to 40%, 80% to 20%, about 20% to about 80%, about 40% to about 60%, about 50% to about 50%, about 60% to about 40%, or about 80% to about 20%, 90% to 10%, 99% to 1%, about 20% to about 80%, about 40% to about 60%, about 50% to about 50%, about 60% to about 40%, about 80% to about 20%, about 90% to about 10%, about 99% to about 1%, or a ratio within a range defined by any two of the aforementioned percentages.

23. The method of any one of alternatives 15-22, wherein the at least one heterogeneous cell composition is administered intravenously, intraarterially, subcutaneously, intramuscularly, intradermally, intrathecally, intraperitoneally, intraportally, intra-articularly, intraocularly or intrarenally, or any combination thereof.

24. A heterogeneous cell composition comprising:
a population of vimentin-positive (V+)/cytokeratin-negative (C−) cells; and
a population of V+/cytokeratin-positive (C+) cells;
wherein the V+/C− cells and V+/C+ cells are co-cultured;
wherein the V+/C− cells and V+/C+ cells are obtained or derived from canine or feline uterine tissue; and
wherein the V+/C− cells and V+/C+ cells are in a ratio of 20% to 80%, 40% to 60%, 50% to 50%, 60% to 40%, 80% to 20%, about 20% to about 80%, about 40% to about 60%, about 50% to about 50%, about 60% to about 40%, or about 80% to about 20%, or a ratio within a range defined by any two of the aforementioned percentages.

25. The composition of alternative 24, further comprising fibroblast growth factor 2 (FGF-2).

26. The composition of alternative 25, wherein the FGF-2 is recombinant human FGF-2.

27. The composition of alternative 25 or 26, wherein the FGF-2 is at a concentration of 8 ng/mL.

28. The composition of any one of alternatives 24-26, wherein the V+/C− cells and V+/C+ cells are co-cultured in at least one tissue culture container that is not pre-treated with biological or synthetic coatings that enhance cell attachment and/or growth, including but not limited to cell-based feeder layers, polymers, proteins, polypeptides, peptides, antibodies, nucleic acids, DNA, RNA, sugars, polysaccharides, carbohydrates, lipids, poly-lysine, poly-ornithine, collagen, gelatin, fibronectin, vitronectin, laminin, elastin, tenascin, heparan sulfate, entactin, nidogen, osteopontin, extracellular matrix, basement membrane, Matrigel, hydrogel, PEI, WGA, hyaluronic acid, or any combination thereof.

29. The composition of any one of alternatives 24-28, wherein the V+/C− cells and V+/C+ cells are co-cultured in at least one tissue culture container for 3, 4, 5, or 6 passages, days, or culture intervals.

30. The composition of any one of alternatives 24-29, wherein the uterine tissue is obtained from a spay procedure.

31. The composition of any one of alternatives 24-30, comprising 5 million, 6 million, 7 million, 8 million, 9 million, 10 million, 11 million, 12 million, 13 million, 14 million, 15 million, 16 million, 17 million, 18 million, 19 million, 20 million, 30 million, 40 million, 50 million, 60 million, 70 million, 80 million, 90 million, or 100 million or about 5 million, about 6 million, about 7 million, about 8 million, about 9 million, about 10 million, about 11 million, about 12 million, about 13 million, about 14 million, about 15 million, about 16 million, about 17 million, about 18 million, about 19 million, about 20 million, about 30 million, about 40 million, about 50 million, about 60 million, about 70 million, about 80 million, about 90 million, or about 100 million V+/C− cells, or any number within a range defined by any two of the aforementioned numbers.

32. The composition of any one of alternatives 24-31, comprising 5 million, 6 million, 7 million, 8 million, 9 million, 10 million, 11 million, 12 million, 13 million, 14 million, 15 million, 16 million, 17 million, 18 million, 19 million, 20 million, 30 million, 40 million, 50 million, 60 million, 70 million, 80 million, 90 million, or 100 million or about 5 million, about 6 million, about 7 million, about 8 million, about 9 million, about 10 million, about 11 million, about 12 million, about 13 million, about 14 million, about 15 million, about 16 million, about 17 million, about 18 million, about 19 million, about 20 million, about 30 million, about 40 million, about 50 million, about 60 million, about 70 million, about 80 million, about 90 million, or about 100 million V+/C+ cells, or any number within a range defined by any two of the aforementioned numbers.

33. The composition of any one of alternatives 24-32, further comprising an additive, supplement, antibiotic, vitamin, growth factor, cryoprotectant, buffer, salt, protein, polypeptide, peptide, sugar, polysaccharide, or carbohydrate including but not limited to trehalose, DMSO, or albumin, or any combination thereof.

34. The composition of any one of alternatives 24-33, wherein the V+/C− cells and V+/C+ cells are obtained or derived from the same canine or feline uterine tissue.

35. The composition of any one of alternatives 24-34, further comprising a cryopreservation medium.

36. The composition of alternative 35, wherein the cryopreservation medium comprises:
(a) CryoStor CS5 and/or BioLife Solutions CS10;
(b) 98% Hespan and 2% DMSO;
(c) about 98% Hespan and about 2% DMSO;
(d) 2-10% DMSO and 2-20% FCS in a growth medium; or
(e) about 2-10% DMSO and about 2-20% FCS in a growth medium.

37. A method of preparing a heterogeneous cell composition, comprising:
contacting a single cell suspension comprising V+/C− cells and V+/C+ cells with FGF-2; and
culturing the single cell suspension with FGF-2 for 3, 4, 5, or 6 passages, days, or culture intervals, wherein the single cell suspension is obtained or derived from canine or feline uterine tissue; and
wherein at the end of 3, 4, 5 or 6 passages, days, or culture intervals, the V+/C− cells and V+/C+ cells are in a ratio of 20% to 80%, 40% to 60%, 50% to 50%, 60% to 40%, 80% to 20%, about 20% to about 80%, about 40% to about 60%, about 50% to about 50%, about 60% to about 40%, or about 80% to about 20%, or a ratio within a range defined by any two of the aforementioned percentages.

38. The method of alternative 37, wherein the single cell suspension is obtained or derived from the same canine or feline uterine tissue.

39. The method of alternative 37 or 38, wherein the canine or feline uterine tissue is enzymatically dissociated to form the single cell suspension.

40. The method of any one of alternatives 37-39, wherein the FGF-2 is recombinant human FGF-2.

41. The method of any one of alternatives 37-40, wherein the FGF-2 is at a concentration of 8 ng/mL.

42. The method of any one of alternatives 37-41, wherein the single cell suspension is cultured for at least 4 passages, days, or culture intervals.

43. A method of treating, inhibiting, or ameliorating chronic kidney disease, atopic dermatitis, immune mediated arthritis, hepatitis, liver disease, inflammatory bowel disease, osteoarthritis, intravertebral disc disease, keratoconjunctivitis sicca (dry eye), pancreatitis, fibrosis, sclerosis, amyloidosis, immune mediated polyarthritis, or wounds in a canine or feline subject in need thereof, comprising:
providing at least one heterogeneous cell composition comprising a population of V+/C− cells and a population of V+/C+ cells, wherein the V+/C− cells and V+/C+ cells are obtained or derived from canine or feline uterine tissue and wherein the canine or feline uterine tissue is autologous or allogeneic to the canine or feline subject; and
administering the at least one heterogeneous cell composition to the canine or feline subject.

44. The method of alternative 43, wherein the V+/C− cells and V+/C+ cells are in a ratio of 20% to 80%, 40% to 60%, 50% to 50%, 60% to 40%, 80% to 20%, about 20% to about 80%, about 40% to about 60%, about 50% to about 50%, about 60% to about 40%, or about 80% to about 20%, 90% to 10%, 99% to 1%, about 20% to about 80%, about 40% to about 60%, about 50% to about 50%, about 60% to about 40%, about 80% to about 20%, about 90% to about 10%, about 99% to about 1%, or a ratio within a range defined by any two of the aforementioned percentages.

45. A method of treating, inhibiting, or ameliorating chronic kidney disease, atopic dermatitis, immune mediated arthritis, hepatitis, liver disease, inflammatory bowel disease, osteoarthritis, intravertebral disc disease, keratoconjunctivitis sicca (dry eye), pancreatitis, fibrosis, sclerosis, amyloidosis, immune mediated polyarthritis or wounds in a canine or feline subject in need thereof, comprising:
providing at least one heterogenous cell composition of any one of alternatives 1-14 or 24-36; and
administering the at least one heterogeneous cell composition to the canine or feline subject.

46. The method of any one of alternatives 37-45, wherein the at least one heterogeneous cell composition is administered intravenously, intraarterially, subcutaneously, intramuscularly, intradermally, intrathecally, intraperitoneally, intraportally, intra-articularly, intraocularly or intrarenally, or any combination thereof.

47. The method of any one of alternatives 37-46, wherein the at least one heterogeneous cell composition is thawed from a cryopreserved state and transferred to a delivery device or container, such as a syringe, comprising a suitable buffer, diluent or fluid, such as phosphate buffered saline or lactated Ringer's solution, before administration.

48. The composition of any one of alternatives 1-14 or 24-36 for use in the treatment of canine or feline chronic kidney disease, atopic dermatitis, immune mediated arthritis, hepatitis, liver disease, inflammatory bowel disease, osteoarthritis, intravertebral disc disease, keratoconjunctivitis sicca (dry eye), pancreatitis, fibrosis, sclerosis, amyloidosis, immune mediated polyarthritis or wounds.

49. The composition of any one of alternatives 1-14 or 24-36 for use as a medicament.

50. A heterogeneous cell composition comprising:
(a) a population of vimentin-positive (V+)/cytokeratin-negative (C−) cells;
(b) a population of vimentin-negative (V−)/cytokeratin-positive (C+) cells; and
(c) a population of V+/C+ cells;
wherein the populations of (a)-(c) are co-cultured;
wherein the populations of (a)-(c) are obtained or derived from canine or feline uterine tissue; and
wherein the population of V+/C+ cells is found at a percentage of 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, or 30%, or any percentage within a range defined by any two of the aforementioned percentages, of the total number of the cells of the heterogeneous cell composition.

51. The heterogeneous cell composition of alternative 50, wherein the population of V+/C− cells is found at a percentage of 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%, or any percentage within a range defined by any two of the aforementioned percentages, of the total number of cells of the heterogeneous cell composition.

52. The heterogeneous cell composition of alternative 50 or 51, wherein the population of V−/C+ cells is found at a percentage of 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, or 60%, or any percentage within a range defined by any two of the aforementioned percentages, of the total number of cells of the heterogeneous cell composition.

53. The heterogeneous cell composition of any one of alternatives 50-52, wherein the population of V+/C− cells and the population of V−/C+ cells are in a ratio of 20% to 80%, 40% to 60%, 50% to 50%, 60% to 40%, 80% to 20%, 90% to 10%, 99% to 1%, about 20% to about 80%, about 40% to about 60%, about 50% to about 50%, about 60% to about 40%, about 80% to about 20%, about 90% to about 10%, about 99% to about 1%, or a ratio within a range defined by any two of the aforementioned percentages.

54. The heterogeneous cell composition of any one of alternatives 50-53, further comprising FGF-2.

55. The heterogeneous cell composition of any one of alternatives 50-54, wherein the FGF-2 is recombinant human FGF-2.

56. The heterogeneous cell composition of any one of alternatives 50-55, wherein the FGF-2 is at a concentration of 8 ng/mL or about 8 ng/mL.

57. The heterogeneous cell composition of any one of alternatives 50-56, wherein the populations of (a)-(c) are co-cultured in at least one tissue culture container that is not pre-treated with biological or synthetic coatings that enhance cell attachment and/or growth, including but not limited to cell-based feeder layers, polymers, proteins, polypeptides, peptides, antibodies, nucleic acids, DNA, RNA, sugars, polysaccharides, carbohydrates, lipids, poly-lysine, poly-ornithine, collagen, gelatin, fibronectin, vitronectin, laminin, elastin, tenascin, heparan sulfate, entactin, nidogen, osteopontin, extracellular matrix, basement membrane, Matrigel, hydrogel, PEI, WGA, hyaluronic acid, or any combination thereof.

58. The heterogeneous cell composition of any one of alternatives 50-57, wherein the populations of (a)-(c) are co-cultured in at least one tissue culture container for 3, 4, 5, or 6 passages, days, or culture intervals.

59. The heterogeneous cell composition of any one of alternatives 50-58, wherein the uterine tissue is obtained from a spay procedure.

60. The heterogeneous cell composition of any one of alternatives 50-59, comprising 5 million, 6 million, 7 million, 8 million, 9 million, 10 million, 11 million, 12 million, 13 million, 14 million, 15 million, 16 million, 17 million, 18 million, 19 million, 20 million, 30 million, 40 million, 50 million, 60 million, 70 million, 80 million, 90 million, or 100 million or about 5 million, about 6 million, about 7 million, about 8 million, about 9 million, about 10 million, about 11 million, about 12 million, about 13 million, about 14 million, about 15 million, about 16 million, about 17 million, about 18 million, about 19 million, about 20 million, about 30 million, about 40 million, about 50 million, about 60 million, about 70 million, about 80 million, about 90 million, or about 100 million V+/C− cells, or any number within a range defined by any two of the aforementioned numbers.

61. The heterogeneous cell composition of any one of alternatives 50-60, comprising 5 million, 6 million, 7 million, 8 million, 9 million, 10 million, 11 million, 12 million, 13 million, 14 million, 15 million, 16 million, 17 million, 18 million, 19 million, 20 million, 30 million, 40 million, 50 million, 60 million, 70 million, 80 million, 90 million, or 100 million or about 5 million, about 6 million, about 7 million, about 8 million, about 9 million, about 10 million, about 11 million, about 12 million, about 13 million, about 14 million, about 15 million, about 16 million, about 17 million, about 18 million, about 19 million, about 20 million, about 30 million, about 40 million, about 50 million, about 60 million, about 70 million, about 80 million, about 90 million, or about 100 million V−/C+ cells, or any number within a range defined by any two of the aforementioned numbers.

62. The heterogeneous cell composition of any one of alternatives 50-61, comprising 5 million, 6 million, 7 million, 8 million, 9 million, 10 million, 11 million, 12 million, 13 million, 14 million, 15 million, 16 million, 17 million, 18 million, 19 million, 20 million, 30 million, 40 million, 50 million, 60 million, 70 million, 80 million, 90 million, or 100 million or about 5 million, about 6 million, about 7 million, about 8 million, about 9 million, about 10 million, about 11 million, about 12 million, about 13 million, about 14 million, about 15 million, about 16 million, about 17 million, about 18 million, about 19 million, about 20 million, about 30 million, about 40 million, about 50 million, about 60 million, about 70 million, about 80 million, about 90 million, or about 100 million V+/C+ cells, or any number within a range defined by any two of the aforementioned numbers.

63. The heterogeneous cell composition of any one of alternatives 50-62, wherein the heterogeneous cell composition is further defined by a population of cells positive for both CD44 and CD326.

64. The heterogeneous cell composition of alternative 63, wherein the population of cells positive for both CD44 and CD326 is found at a percentage of 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55% or any percentage within a range defined by any two of the aforementioned percentages, of the total number of the cells of the heterogeneous cell composition.
65. The heterogeneous cell composition of any one of alternatives 50-64, further comprising an additive, supplement, antibiotic, vitamin, growth factor, cryoprotectant, buffer, salt, protein, polypeptide, peptide, sugar, polysaccharide, or carbohydrate including but not limited to trehalose, DMSO, or albumin, or any combination thereof.
66. The heterogeneous cell composition of any one of alternatives 50-65, wherein the populations of (a)-(c) are obtained or derived from the same canine or feline uterine tissue.
67. The heterogeneous cell composition of any one of alternatives 50-66, further comprising a cryopreservation medium.
68. The heterogeneous cell composition of alternative 67, wherein the cryopreservation medium comprises:
(a) CryoStor CS5 and/or BioLife Solutions CS10;
(b) 98% Hespan and 2% DMSO;
(c) about 98% Hespan and about 2% DMSO;
(d) 2-10% DMSO and 2-20% FCS in a growth medium; or
(e) about 2-10% DMSO and about 2-20% FCS in a growth medium.
69. A method of preparing a heterogeneous cell composition, comprising:
dissociating canine or feline uterine tissue into a single cell suspension; and
culturing the single cell suspension for 3, 4, 5, or 6 passages, days, or culture intervals;
thereby preparing the heterogeneous cell composition from the cultured single cell suspension;
wherein at the end of the 3, 4, 5 or 6 passages, days, or culture intervals, the heterogeneous cell composition comprises a population of cells positive for both Vimentin and Cytokeratin-18.
70. The method of alternative 69, wherein the population of cells positive for both Vimentin and Cytokeratin-18 is present at a percentage of 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55% or any percentage within a range defined by any two of the aforementioned percentages, of the total number of the cells of the heterogeneous cell composition.
71. The method of alternative 69 or 70, wherein the dissociating step comprises enzymatic dissociation.
72. The method of alternative 71, wherein the enzymatic dissociation comprises contacting the canine or feline uterine tissue with trypsin, chymotrypsin, collagenase, papain, hyaluronidase, elastase, thermolysin, neutral protease, or any combination thereof.
73. The method of any one of alternatives 69-72, wherein the single cell suspension is cultured with FGF-2.
74. The method of alternative 73, wherein the FGF-2 is recombinant human FGF-2.
75. The method of alternative 73 or 74, wherein the FGF-2 is at a concentration of 8 ng/mL or about 8 ng/mL.
76. The method of any one of alternatives 69-75, wherein the single cell suspension is cultured for at least 4 passages, days, or culture intervals.
77. The method of any one of alternatives 69-76, wherein the heterogeneous cell composition is further defined by a population of cells positive for both CD44 and CD326.
78. The method of alternative 77, wherein the population of cells positive for both CD44 and CD326 is found at a percentage of 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55% or any percentage within a range defined by any two of the aforementioned percentages, of the total number of the cells of the heterogeneous cell composition.
79. The method of any one of alternatives 69-78, wherein the heterogeneous cell composition is the heterogeneous cell composition of any one of alternatives 50-68.
80. A method of treating, inhibiting, or ameliorating chronic kidney disease, atopic dermatitis, immune mediated arthritis, hepatitis, liver disease, inflammatory bowel disease, osteoarthritis, intravertebral disc disease, keratoconjunctivitis sicca (dry eye), pancreatitis, fibrosis, sclerosis, amyloidosis, immune mediated polyarthritis, or wounds in a canine or feline subject in need thereof, comprising:
administering at least one heterogeneous cell composition to the canine or feline subject;
wherein the at least one heterogeneous cell composition comprises a population of cells positive for both Vimentin and Cytokeratin-18.
81. The method of alternative 80, wherein the population of cells positive for both Vimentin and Cytokeratin-18 is present at a percentage of 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55% or any percentage within a range defined by any two of the aforementioned percentages, of the total number of the cells of the heterogeneous cell composition.
82. The method of alternative 80 or 81, wherein the heterogeneous cell composition is further defined by a population of cells positive for both CD44 and CD326.
83. The method of alternative 82, wherein the population of cells positive for both CD44 and CD326 is found at a percentage of 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55% or any percentage within a range defined by any two of the aforementioned percentages, of the total number of the cells of the heterogeneous cell composition.
84. The method of any one of alternatives 80-83, wherein the heterogeneous cell composition is autologous or allogeneic to the canine or feline subject.
85. The method of any one of alternatives 80-84, wherein the at least one heterogeneous cell composition is the heterogeneous cell composition of any one of alternatives 50-68 or is produced by the method of any one of alternatives 69-79.

86. The method of any one of alternatives 80-85, wherein the at least one heterogeneous cell composition is administered intravenously, intraarterially, subcutaneously, intramuscularly, intradermally, intrathecally, intraperitoneally, intraportally, intra-articularly, intraocularly or intrarenally, or any combination thereof.

87. The method of any one of alternatives 80-86, wherein the at least one heterogeneous cell composition is thawed from a cryopreserved state and transferred to a delivery device or container, such as a syringe, comprising a suitable buffer, diluent or fluid, such as phosphate buffered saline or lactated Ringer's solution, before administration.

88. The method of alternative 87, wherein thawing the at least one heterogeneous cell composition from the cryopreserved state comprises diluting the at least one heterogeneous cell composition by 1.5×, 2×, 3×, 4×, 5×, 6×, 7×, 8×, 9×, 10×, or at least 1.5×, 2×, 3×, 4×, 5×, 6×, 7×, 8×, 9×, or 10×.

89. The heterogeneous cell composition of any one of alternatives 50-68 for use in the treatment of canine or feline chronic kidney disease, atopic dermatitis, immune mediated arthritis, hepatitis, liver disease, inflammatory bowel disease, osteoarthritis, intravertebral disc disease, keratoconjunctivitis sicca (dry eye), pancreatitis, fibrosis, sclerosis, amyloidosis, immune mediated polyarthritis or wounds.

90. The heterogeneous cell composition of any one of alternatives 50-68 for use as a medicament, such as a medicament for treating or inhibiting canine or feline chronic kidney disease, atopic dermatitis, immune mediated arthritis, hepatitis, liver disease, inflammatory bowel disease, osteoarthritis, intravertebral disc disease, keratoconjunctivitis sicca (dry eye), pancreatitis, fibrosis, sclerosis, amyloidosis, immune mediated polyarthritis or wounds.

91. A cell composition comprising a canine or feline cell, which is positive for both Vimentin and Cytokeratin-18, preferably a uterine cell.

92. The cell composition of alternative 91, wherein said cell composition further comprises mesenchymal progenitor cells and/or epithelial progenitor cells.

93. The cell composition of alternative 91 or 92, further comprising fibroblast growth factor 2 (FGF-2).

94. The cell composition of alternative 93, wherein the FGF-2 is recombinant human FGF-2.

95. The cell composition of alternative 93 or 94, wherein the FGF-2 is present at a concentration of 8 ng/mL.

96. The cell composition of any one of alternatives 91-95, wherein the cell composition is cultured in at least one tissue culture container that is not pre-treated with biological or synthetic coatings that enhance cell attachment and/or growth, including but not limited to cell-based feeder layers, polymers, proteins, polypeptides, peptides, antibodies, nucleic acids, DNA, RNA, sugars, polysaccharides, carbohydrates, lipids, polylysine, poly-ornithine, collagen, gelatin, fibronectin, vitronectin, laminin, elastin, tenascin, heparan sulfate, entactin, nidogen, osteopontin, extracellular matrix, basement membrane, Matrigel, hydrogel, PEI, WGA, hyaluronic acid, or any combination thereof.

97. The cell composition of any one of alternatives 91-96, wherein the uterine tissue is obtained from a spay procedure.

98. The cell composition of any one of alternatives 91-97, further comprising an additive, supplement, antibiotic, vitamin, growth factor, cryoprotectant, buffer, salt, protein, polypeptide, peptide, sugar, polysaccharide, or carbohydrate including but not limited to trehalose, DMSO, or albumin, or any combination thereof.

99. The cell composition of any one of alternatives 91-98, further comprising a cryopreservation medium.

100. The cell composition of alternative 99, wherein the cryopreservation medium comprises:
(a) CryoStor CS5 and/or BioLife Solutions CS10;
(b) 98% Hespan and 2% DMSO;
(c) about 98% Hespan and about 2% DMSO;
(d) 2-10% DMSO and 2-20% FCS in a growth medium; or
(e) about 2-10% DMSO and about 2-20% FCS in a growth medium.

101. A method of treating, inhibiting, or ameliorating chronic kidney disease, atopic dermatitis, immune mediated arthritis, hepatitis, liver disease, inflammatory bowel disease, osteoarthritis, intravertebral disc disease, keratoconjunctivitis sicca (dry eye), pancreatitis, fibrosis, sclerosis, amyloidosis, immune mediated polyarthritis or wounds in a canine or feline subject in need thereof, comprising:
administering the cell composition of any one of alternatives 91-100 to the canine or feline subject.

102. The method of alternative 101, wherein the cell composition is administered intravenously, intraarterially, subcutaneously, intramuscularly, intradermally, intrathecally, intraperitoneally, intraportally, intra-articularly, intraocularly or intrarenally, or any combination thereof.

103. The method of alternative 101 or 102, wherein the cell composition is thawed from a cryopreserved state and transferred to a delivery device or container, such as a syringe, comprising a suitable buffer, diluent or fluid, such as phosphate buffered saline or lactated Ringer's solution, before administration.

104. The method of alternative 103, wherein thawing the at least one heterogeneous cell composition from the cryopreserved state comprises diluting the at least one heterogeneous cell composition by 1.5×, 2×, 3×, 4×, 5×, 6×, 7×, 8×, 9×, 10×, or at least 1.5×, 2×, 3×, 4×, 5×, 6×, 7×, 8×, 9×, or 10×.

105. The cell composition of any one of alternatives 91-100 for use in the treatment or inhibition of canine or feline chronic kidney disease, atopic dermatitis, immune mediated arthritis, hepatitis, liver disease, inflammatory bowel disease, osteoarthritis, intravertebral disc disease, keratoconjunctivitis sicca (dry eye), pancreatitis, fibrosis, sclerosis, amyloidosis, immune mediated polyarthritis or wounds.

106. The composition of any one of alternatives 91-100 for use as a medicament.

BRIEF DESCRIPTION OF THE DRAWINGS

In addition to the features described above, additional features and variations will be readily apparent from the following descriptions of the drawings and exemplary embodiments. It is to be understood that these drawings depict typical embodiments and are not intended to be limiting in scope.

FIG. 15A-C depict dual staining of Vimentin and Cytokeratin-18 staining in single cells of one exemplary feline URC preparation. FIG. 15A depicts Vimentin staining. FIG. 15B depicts Cytokeratin-18 staining. FIG. 15C depicts the merge of Vimentin and Cytokeratin-18 staining.

FIG. 16A-C depict dual staining of Vimentin and Cytokeratin-18 staining in single cells of a second exemplary feline URC preparation. FIG. 16A depicts Vimentin staining. FIG. 16B depicts Cytokeratin-18 staining. FIG. 16C depicts the merge of Vimentin and Cytokeratin-18 staining.

DETAILED DESCRIPTION

Figure 1:
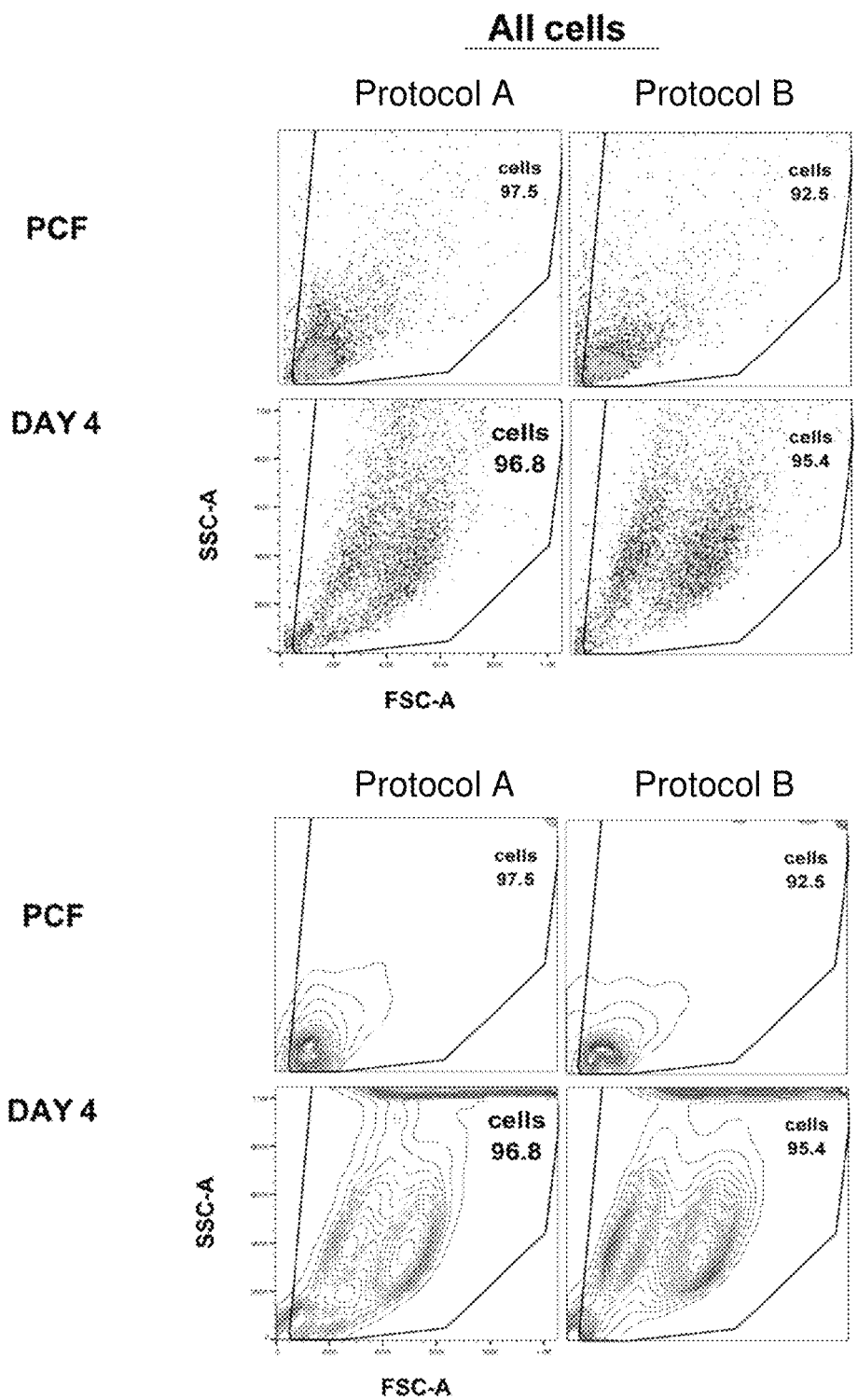
FIG. 1 depicts dot and contour flow cytometric plots of forward scatter (FSC-A) and side scatter (SSC-A) for total cell populations of PCF and Day 4 samples of canine uterine-derived cells processed according to Protocols A and B for Example 3.

Provided herein are cell compositions, preferably heterologous cell compositions obtained from uterine tissue (such as from a spay procedure), termed Uterine-derived Regenerative Cells (URCs). As provided herein, URCs may be classified as stem/progenitor cells based on several well-established characteristics of stem/progenitor cells. The canine and feline URCs disclosed herein have CD marker profiles that qualitatively match profiles for human MSCs. The canine and feline URCs also are strongly positive for CD44, a known marker of stem/progenitor cells. The canine and feline URCs can also be induced to differentiate into adipo-chondro-, and osteogenic cell lineages, which is another requirement associated with multipotent human MSCs. Finally, the canine and feline URCs grow in an adherent manner in culture. Thus, the canine and feline URCs disclosed herein meet the requirements for being multipotent stem/progenitor cells.

However, the canine and feline URCs demonstrate a number of unexpected characteristics for stem/progenitor cells. Both canine and feline URCs display the unexpected property of dual-expression of progenitor cell-like and epithelial cell-like characteristics in the same cell. This appears to be the first report of dual-expression of markers for stemness and epithelial cells in a single cell. The dual-expression was observed in several ways. The physical existence of dual-expressing cells in feline URCs was demonstrated by immunofluorescence, where some cells clearly expressed Vimentin (a stemness biomarker) and some cells expressed Cytokeratin-18 (an epithelial biomarker), while a small population co-expressed both biomarkers. Both canine and feline URCs were observed to express Vimentin and Cytokeratin-18 by flow cytometric analysis. In addition, both canine and feline URCs expressed CD44 and CD326, in which CD44 is a biomarker for stemness and CD326 is a biomarker for epithelial cells. Furthermore, canine URCs also were observed by flow cytometric analysis to express CD44 and Cytokeratin-18. Thus, the URC preparations disclosed herein demonstrate the presence of cells that express both progenitor cell-like and epithelial cell-like properties in the same cells. The dual-expressing cell populations were observed in higher passage cultures of both canine and feline URCs, which supports their unique potential as therapeutic agents. Accordingly, some embodiments include a cell composition and methods of use thereof, wherein said cell composition comprises a cell that expresses both Vimentin and Cytokeratin-18, wherein said cell that expresses both Vimentin and Cytokeratin-18 can be in a purified or isolated form or present in a heterogeneous population of cells, such as mixed with mesenchymal cells that express Vimentin and/or epithelial cells that express Cytokeratin-18.

A canine URC preparation has been evaluated in a clinical study for treating canine atopic dermatitis. Reductions in 30 day post-treatment assessment scores of PVAS, CADESI-4 and CADLI (clinical metrics for assessing atopic dermatitis in dogs) compared to pre-treatment scores suggest that the canine URC preparation used has provided a therapeutic benefit.

A feline URC preparation has been evaluated in a clinical study on improving the status of cats with chronic kidney disease. One of the primary study outcomes of a 20% increase in GFR values in more than 50% of the treated cats for the 6-month study was met in the study, along with improved diet and water consumption. This is the first study in which a primary endpoint like improved GFR was reached out of seven published studies.

Without being limited to a single mechanism of therapeutic benefit, one disease condition common to both atopic dermatitis and chronic kidney disease is the presence of a pro-inflammatory tissue reaction. Both the canine and feline URCs described herein have demonstrated the ability of downregulating a pro-inflammatory environment as measured in a MLR assay. Thus, the URCs as disclosed herein provide a therapeutic benefit in part due to their ability to reduce pro-inflammatory tissue responses.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein.

Definitions

Unless otherwise defined, all technical and scientific terms used herein have the same meaning as commonly understood by one of ordinary skill in the art to which this subject matter belongs. The terminology used in the description of the subject matter herein is for the purpose of describing particular embodiments only and is not intended to be limiting of the subject matter.

The articles "a" and "an" are used herein to refer to one or to more than one (for example, at least one) of the grammatical object of the article. By way of example, "an element" means one element or more than one element.

The terms "about" or "around" as used herein refer to a quantity, level, value, number, frequency, percentage, dimension, size, amount, weight or length that varies by as much as 30, 25, 20, 15, 10, 9, 8, 7, 6, 5, 4, 3, 2 or 1% to a reference quantity, level, value, number, frequency, percentage, dimension, size, amount, weight or length.

Throughout this specification, unless the context requires otherwise, the words "comprise," "comprises," and "comprising" will be understood to imply the inclusion of a stated step or element or group of steps or elements but not the exclusion of any other step or element or group of steps or elements. By "consisting of" is meant including, and limited to, whatever follows the phrase "consisting of" Thus, the phrase "consisting of" indicates that the listed elements are required or mandatory, and that no other elements may be present. By "consisting essentially of" is meant including any elements listed after the phrase and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they materially affect the activity or action of the listed elements.

The "individual", "patient" or "subject" treated as disclosed herein is, in some embodiments, a mammal. The term "mammal" as used herein includes, but is not limited to, humans, non-human animals, including primates, cattle, sheep, goats, pigs, horses, cats, dogs, rabbits, rodents (e.g., rats or mice), monkeys, etc. In some embodiments, the individual, patient, or subject is a cat (feline) or dog (canine). The subject can be a subject "in need of" the methods disclosed herein or can be a subject that is experiencing a disease state and/or is anticipated to experience a disease state, and the methods and compositions of the invention are used for therapeutic and/or prophylactic treatment. A subject can be a patient, which refers to a subject presenting to a medical provider for diagnosis or treatment of a disease. A subject can be afflicted with or is susceptible to a disease or disorder but may or may not display symptoms of the disease or disorder.

Some embodiments disclosed herein relate to selecting a subject or patient in need. In some embodiments, a subject is selected who has a disease, in need of treatment or therapy for a disease, at risk of contracting a disease, previously had a disease, or does not currently have a disease. In some embodiments, a subject is selected who has previously been non-responsive to another therapy. In some embodiments, the disease is chronic kidney disease, atopic dermatitis, immune mediated arthritis, hepatitis, liver disease, inflammatory bowel disease, osteoarthritis, intravertebral disc disease, keratoconjunctivitis sicca (dry eye), pancreatitis, fibrosis, sclerosis, amyloidosis, immune mediated polyarthritis or a wound. In some embodiments, a subject is selected who may have any combination of the aforementioned selection criteria. Such selection of subjects or patients can be made by a clinician or veterinarian or both by clinical or diagnostic evaluation or both.

The term "wound" as used herein refers to an injury of the skin, epidermis, and/or dermis of a subject. A wound can be an open wound or a closed wound. An open wound includes but is not limited to incisions, lacerations, abrasions, avulsions, punctures, penetration, or gunshot wounds. A closed wound includes but is not limited to hematomas or crush injuries. A wound may be at risk of infection by a pathogen such as a bacterium, virus, fungus, or protozoan.

The terms "atopic dermatitis" and "eczema" as used herein relate to the common inflammation-associated disease resulting in pruritic skin. This disease may be caused by a wide range of factors, such as allergens in food, airborne allergens such as pollen and dust, or genetic disposition. Atopic dermatitis affects animals, including pets such as cats and dogs, in addition to humans. Some cases of atopic dermatitis may be relatively easily treated, such as termination of use of a certain type of food. However, in many cases, there is no cure for atopic dermatitis, and the only treatment available are anti-histamines or anti-inflammatory steroids. However, these treatments may cause other side effects, such as increased susceptibility to infection.

The terms "effective amount" or "effective dose" as used herein, refers to that amount of a recited composition or compound that results in an observable effect. Actual dosage levels of active ingredients in an active composition of the presently disclosed subject matter can be varied so as to administer an amount of the active composition or compound that is effective to achieve the desired response for a particular subject and/or application. The selected dosage level will depend upon a variety of factors including, but not limited to, the activity of the composition, formulation, route of administration, combination with other drugs or treatments, severity of the condition being treated, and the physical condition and prior medical history of the subject being treated. In some embodiments, a minimal dose is administered, and dose is escalated in the absence of dose-limiting toxicity to a minimally effective amount. Determination and adjustment of an effective dose, as well as evaluation of when and how to make such adjustments, are contemplated herein.

The terms "function" and "functional" as used herein refer to a biological, enzymatic, or therapeutic function.

As used herein, the term "isolated" refers to a substance and/or entity that has been (1) separated from at least some of the components with which it was associated when initially produced (whether in nature and/or in an experimental setting), and/or (2) produced, prepared, and/or manufactured by the hand of man. Isolated substances and/or entities may be separated from equal to or at least about 10%, about 20%, about 30%, about 40%, about 50%, about 60%, about 70%, about 80%, about 90%, about 95%, about 98%, about 99%, substantially 100%, or 100% of the other components with which they were initially associated (or ranges including and/or spanning the aforementioned values). In some embodiments, isolated agents are more than about 80%, about 85%, about 90%, about 91%, about 92%, about 93%, about 94%, about 95%, about 96%, about 97%, about 98%, about 99%, substantially 100%, or 100% pure (or ranges including and/or spanning the aforementioned values). As used herein, a substance that is "isolated" may be "pure" (e.g., substantially free of other components). As used herein, the term "isolated cell" may refer to a cell not contained in a multi-cellular organism or tissue.

The terms "primary cell fraction" or "PCF" refer to the population of cells obtained from the isolation, dissociation, and/or purification steps taken to prepare a viable single cell suspension from the target tissue prior to culturing steps. The PCF population is distinct from the population of cells that are obtained after the one or more culturing steps, as the relative fraction of certain cell types within the heterogenous population and the properties of said cell types changes over the one or more culturing steps.

The terms "mesenchymal progenitor cell" or "MPC" refer to a population of spindle-shaped adherent cells that exhibit the potential to differentiate into osteogenic, chondrogenic, and adipogenic lineages. MPCs may also be referred as "mesenchymal stromal cells", "mesenchymal stem cells", "MSCs", or "stromal cells". MPCs have been isolated primarily from bone marrow, but are also present in umbilical cord tissue, umbilical cord blood, white adipose tissue, and placenta tissue, among other tissues. Upon culture, MPCs generally express CD105, CD73, CD90 and generally do not express CD14, CD19, CD34, CD45, and HLA-DR (Class II). Furthermore, the cytoskeletal intermediate filament vimentin (V) is a known marker of MPCs. Their ability to differentiate into multiple cell types, as well as lack of MHC class II, have prompted investigation for use in autologous or allogeneic regenerative cell therapy.

The term "epithelial progenitor cells" refers to a population of cuboidal-shaped adherent cells that are responsible for the production and regeneration of the epithelium and constituent extracellular matrix that make up the surface of tissues in the body. These cells generally express CD44, and cell adhesion proteins such as E-cadherin, epithelial cell adhesion molecule (EpCAM, CD326), among others, and generally do not express CD45. Furthermore, keratin intermediate filament proteins such as cytokeratin (C), e.g. cytokeratin-14, cytokeratin-18, are known markers for epithelial cells and EPCs.

The terms "fibroblast growth factor" or "FGF" refer to the family of polypeptide growth factors with pleiotropic effects on cell proliferation, differentiation, and reorganization by binding to fibroblast growth factor receptor (FGFR) proteins on cell surfaces. There are 22 known FGFs in humans. One of these is fibroblast growth factor 2 (FGF-2, basic fibroblast growth factor, bFGF, FGF-β), which, among other functions, has been shown to maintain an undifferentiated state in stem cells. In some embodiments, FGF-2 is present in a growth medium for cell culture. In some embodiments, the FGF-2 is present at a concentration of 0.01, 0.05, 0.1, 1, 2, 3, 4, 5, 6, 7, 8, 9, 10, 15, 20, 30, 40, 50, 60, 70, 80, 90, or 100 ng/mL or any concentration within a range defined by any two of the aforementioned concentrations. In some embodiments, the FGF-2 is present at a concentration of 0.1, 0.5, 1, 2, 3, 4, 5, 6, 7, 8, 9, or 10 ng/mL or any concentration within a range defined by any two of the aforementioned concentrations. In some embodiments, the FGF-2 is present at a concentration of 8 ng/mL. In some embodiments, the FGF-2 is human FGF-2. In some embodiments, the FGF-2 is canine or feline FGF-2. In some embodiments, the FGF-2 is recombinantly produced. In some embodiments, the FGF-2 is recombinantly produced in *E. coli*. In some embodiments, the FGF-2 is produced according to research grade standards or current good manufacturing practice (cGMP) standards.

As used herein, the term "enzymatic dissociation" refers to fragmentation or dissociation of a cellular tissue using the catalytic activity of one or more enzymes. A process generally well known in the art, enzymatic dissociation typically involves the use of proteolytic enzymes (e.g. trypsin or collagenase), or enzymes specific for other molecules (e.g. hyaluronidase) involved in adherence to surface or intercellular bonds.

As used herein, "in vivo" is given its ordinary meaning and refers to the performance of a method inside living organisms, usually animals, mammals, including humans, and plants, as opposed to a tissue extract or dead organism.

As used herein, "ex vivo" is given its ordinary meaning and refers to the performance of a method outside a living organism with little alteration of natural conditions.

As used herein, "in vitro" is given its ordinary meaning and refers to the performance of a method outside of biological conditions, e.g., in a petri dish or test tube.

The term "purity" of any given substance, compound, or material as used herein refers to the actual abundance of the substance, compound, or material relative to the expected abundance. For example, the substance, compound, or material may be at least 80, 85, 90, 91, 92, 93, 94, 95, 96, 97, 98, 99, or 100% pure, including all decimals in between. Purity may be affected by unwanted impurities, including but not limited to nucleic acids, DNA, RNA, nucleotides, proteins, polypeptides, peptides, amino acids, lipids, cell membrane, cell debris, small molecules, degradation products, solvent, carrier, vehicle, or contaminants, or any combination thereof. In some embodiments, the substance, compound, or material is substantially free of host cell proteins, host cell nucleic acids, plasmid DNA, contaminating viruses, proteasomes, host cell culture components, process related components, mycoplasma, pyrogens, bacterial endotoxins, and adventitious agents. Purity can be measured using technologies including but not limited to electrophoresis, SDS-PAGE, capillary electrophoresis, PCR, rtPCR, qPCR, chromatography, liquid chromatography, gas chromatography, thin layer chromatography, enzyme-linked immunosorbent assay (ELISA), spectroscopy, UV-visible spectrometry, infrared spectrometry, mass spectrometry, nuclear magnetic resonance, gravimetry, or titration, or any combination thereof.

The term "yield" of any given substance, compound, or material as used herein refers to the actual overall amount of the substance, compound, or material relative to the expected overall amount. For example, the yield of the substance, compound, or material may be at least 80, 85, 90, 91, 92, 93, 94, 95, 96, 97, 98, 99, or 100% of the expected overall amount, including all decimals in between. Yield may be affected by the efficiency of a reaction or process, unwanted side reactions, degradation, quality of the input substances, compounds, or materials, or loss of the desired substance, compound, or material during any step of the production.

As used herein, "pharmaceutically acceptable" refers to carriers, excipients, and/or stabilizers that are nontoxic to the cell or mammal being exposed thereto at the dosages and concentrations employed or that have an acceptable level of toxicity. A "pharmaceutically acceptable" "diluent," "excipient," and/or "carrier" as used herein is intended to include any and all solvents, dispersion media, coatings, antibacterial and antifungal agents, isotonic and absorption delaying agents, and the like, compatible with administration to humans, cats, dogs, or other vertebrate hosts. Typically, a pharmaceutically acceptable diluent, excipient, and/or carrier is a diluent, excipient, and/or carrier approved by a regulatory agency of a Federal, a state government, or other regulatory agency, or listed in the U.S. Pharmacopeia or other generally recognized pharmacopeia for use in animals, including humans as well as non-human mammals, such as cats and dogs. The term diluent, excipient, and/or "carrier" can refer to a diluent, adjuvant, excipient, or vehicle with which the pharmaceutical composition is administered. Such pharmaceutical diluent, excipient, and/or carriers can be sterile liquids, such as water and oils, including those of petroleum, animal, vegetable or synthetic origin. Water, saline solutions and aqueous dextrose and glycerol solutions can be employed as liquid diluents, excipients, and/or carriers, particularly for injectable solutions. Some examples of a liquid diluent used for injectable solutions include but are not limited to saline, phosphate buffered saline, lactated Ringer's solution, Ringer's acetate solution, or dextrose solution. Suitable pharmaceutical diluents and/or excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, or ethanol and the like. A non-limiting example of a physiologically acceptable carrier is an aqueous pH buffered solution. The physiologically acceptable carrier may also comprise one or more of the following: antioxidants, such as ascorbic acid, low molecular weight (less than about 10 residues) polypeptides, proteins, such as serum albumin, gelatin, immunoglobulins, hydrophilic polymers such as polyvinylpyrrolidone, amino acids, carbohydrates such as glucose, mannose, or dextrins, chelating agents such as EDTA, sugar alcohols such as mannitol or sorbitol, salt-forming counterions such as sodium, and polyethylene glycol (PEG). The composition, if desired, can also contain minor amounts of wetting, bulking, emulsifying agents, or pH buffering agents. These compositions can take the form of solutions, suspensions, emulsion, sustained release formulations and the like. The formulation should suit the mode of administration.

Cryoprotectants are cell composition additives to improve efficiency and yield of low temperature cryopreservation by preventing formation of large ice crystals. Cryoprotectants include but are not limited to DMSO, ethylene glycol, glycerol, propylene glycol, trehalose, formamide, methyl-formamide, dimethyl-formamide, glycerol 3-phosphate, proline, sorbitol, diethyl glycol, sucrose, triethylene glycol, polyvinyl alcohol, polyethylene glycol, or hydroxyethyl starch. Cryoprotectants can be used as part of a cryopreservation medium, which include other components such as nutrients (e.g. albumin, serum, bovine serum, or fetal calf serum [FCS]) to enhance post-thawing survivability of the cells. Some examples of cryopreservation media are CryoStor® CS5, BioLife Solutions CS10, Hespan® (6% hetastarch [hydroxyethyl starch] in 0.9% sodium chloride), and other compositions known in the art comprising DMSO, FCS, and standard growth medium. In these compositions, DMSO may be found at a concentration of 2%, 3%, 4%, 5%, 6%, 7%, 8%, 9%, 10%, 11%, 12%, 13%, 14%, 15%, 16%, 17%, 18%, 19% or 20%, or any percentage within a range defined by any two of the aforementioned numbers. In these compositions, FCS may be found at a concentration of 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, or 30%, or any percentage within a range defined by any two of the aforementioned numbers. These compositions may also include other cryoprotectants listed herein, such as trehalose.

Additional excipients with desirable properties include but are not limited to preservatives, adjuvants, stabilizers, solvents, buffers, diluents, chelating agents, antioxidants, alcohols, ethylenediaminetetraacetic acid (EDTA), citric acid, salts, sodium chloride, sodium bicarbonate, sodium phosphate, sodium borate, sodium citrate, potassium chloride, potassium phosphate, magnesium sulfate sugars, dextrose, fructose, mannose, lactose, galactose, sucrose, sorbitol, cellulose, serum, amino acids, polysorbate 20, polysorbate 80, gelatin, esters, ethers, 2-phenoxyethanol, or vitamins, or any combination thereof. Some excipients may be in residual amounts or contaminants from the process of manufacturing, including but not limited to serum, albumin, ovalbumin, antibiotics, inactivating agents, gelatin, cell debris, nucleic acids, peptides, amino acids, or growth medium components or any combination thereof. The amount of the excipient may be found in composition at a percentage of 0%, 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, 10%, 20%, 30%, 40%, 50%, 60%, 70%, 80%, 90%, 95%, 100% w/w or any percentage by weight in a range defined by any two of the aforementioned numbers.

The term "pharmaceutically acceptable salts" includes relatively non-toxic, inorganic and organic acid, or base addition salts of compositions or excipients, including without limitation, analgesic agents, therapeutic agents, other materials, and the like. Examples of pharmaceutically acceptable salts include those derived from mineral acids, such as hydrochloric acid and sulfuric acid, and those derived from organic acids, such as ethanesulfonic acid, benzenesulfonic acid, p-toluenesulfonic acid, and the like. Examples of suitable inorganic bases for the formation of salts include the hydroxides, carbonates, and bicarbonates of ammonia, sodium, lithium, potassium, calcium, magnesium, aluminum, zinc, and the like. Salts may also be formed with suitable organic bases, including those that are non-toxic and strong enough to form such salts. For example, the class of such organic bases may include but are not limited to mono-, di-, and trialkylamines, including methylamine, dimethylamine, and triethylamine; mono-, di-, or trihydroxyalkylamines including mono-, di-, and triethanolamine; amino acids, including glycine, arginine and lysine; guanidine; N-methylglucosamine; N-methylglucamine; L-glutamine; N-methylpiperazine; morpholine; ethylenediamine; N-benzylphenethylamine; or trihydroxymethyl aminoethane.

Proper formulation is dependent upon the route of administration chosen. Techniques for formulation and administration of the compounds described herein are known to those skilled in the art. Multiple techniques of administering a compound exist in the art including, but not limited to, enteral, oral, rectal, topical, sublingual, buccal, intraaural, epidural, epicutaneous, aerosol, parenteral delivery, including intramuscular, subcutaneous, intra-arterial, intravenous, intraportal, intra-articular, intradermal, peritoneal, intramedullary injections, intrathecal, direct intraventricular, intraperitoneal, intranasal or intraocular injections. Pharmaceutical compositions will generally be tailored to the specific intended route of administration.

As used herein, a "carrier" refers to a compound, particle, solid, semi-solid, liquid, or diluent that facilitates the passage, delivery and/or incorporation of a compound to cells, tissues and/or bodily organs.

As used herein, a "diluent" refers to an ingredient in a pharmaceutical composition that lacks pharmacological activity but may be pharmaceutically necessary or desirable. For example, a diluent may be used to increase the bulk of a potent drug whose mass is too small for manufacture and/or administration. It may also be a liquid for the dissolution of a drug to be administered by injection, ingestion or inhalation. A common form of diluent in the art is a buffered aqueous solution such as, without limitation, phosphate buffered saline that mimics the composition of human blood.

The term "% w/w" or "% wt/wt" as used herein has its ordinary meaning as understood in light of the specification and refers to a percentage expressed in terms of the weight of the ingredient or agent over the total weight of the composition multiplied by 100. The term "% v/v" or "% vol/vol" as used herein has its ordinary meaning as understood in the light of the specification and refers to a percentage expressed in terms of the liquid volume of the compound, substance, ingredient, or agent over the total liquid volume of the composition multiplied by 100.

Uterine-Derived Regenerative Cells (URCs)

The uterus undergoes renewal of the outer structure of the endometrium (aka functionalis in humans) on a periodic basis. Humans cycle approximately every 30-days, but in animals like cats and dogs the cycling is less frequent. There is rapid renewal of the outer endometrial layer, following the shedding (humans) or adsorption (mice) of the outer endometrial layer. For example, after the functionalis is shed in a human, the newly exposed surface undergoes re-epithelialization within 24 hours. Thus, there is a significant pool of stem and progenitor cells found in the basal layer of the endometrium that support the regeneration of the functionalis. The stem and progenitor cells present in the basalis layer are both stromal (mesenchymal, pericyte, etc.) and epithelial, including epithelial stem cells. The epithelial stem cells have been identified as "founder" cells, since they are associated with the extensive proliferation that results from the "natural" uterine endometrial injury of pregnancy and parturition.

Another important cell type found in epithelial tissues is the "transit-amplifying" (TA) cell. TA cells are derived from epithelial stem cells, are unable to "self-renew" (a trait of true stem cells) and are destined to become adult cells required in the homeostasis and repair of stratified epithelial tissues, like the endometrium. Epithelial cells that are CD44+ are considered to be a candidate for the uterine progenitor cell (epithelial progenitor cell). A variety of other cells are present in the endometrium, including stromal fibroblasts, vascular smooth muscle cells, endothelial cells and leukocytes.

Epithelial tissue frequently is found at the interface between the external environment and internal structures, including the uterus, skin, gut, airway tracts, kidney, liver, mammary glands and prostate. An important aspect of epithelial stem cells is their plasticity, which is demonstrated when they are removed from their "niche" in epithelial layers. When epithelial stem cells are removed from their niche and transplanted (either directly or after culturing), the epithelial stem cells assume a greater multipotency, in which unipotent or committed epithelial cells adopt a more "stem cell-like" state via a de-differentiation mechanism.

Uterine tissue is processed according to Protocols B, C, or D, or similar protocols, and yields two main types of cells after being grown in culture: 1) cells that are singly-positive for vimentin (V+; an MSC marker); and 2) cells that are doubly positive for cytokeratin-18 and vimentin (C+/V+) and/or doubly positive for CD44 and CD326 (CD44+/CD326+). Cytokeratin is associated with epithelial cells. Cells obtained from a canine uterus processed with the same protocols described herein yields frequencies of V+ and C+/V+ cells that were roughly 1:1 when examined at day 4 or in later passages, days, or culture intervals in culture. Furthermore, the canine uterus tissue-derived cells also were doubly positive for CD90/CD44, and singly positive for CD44. As mentioned above, the CD44 marker is thought to be associated with epithelial progenitor cells, while the other markers are associated with progenitor cells and fibroblasts.

Described herein is a stable culturing environment in which an "epithelial-like" cell co-existed with a "mesenchymal-like" cell out through Passage 4 and beyond. It has been previously reported that a single cell suspension obtained after an enzymatic digestion of human endometrial tissue when cultured produced two types of plastic-adherent cells: mesenchymal/fibroblastic and epithelial/small round cells. However, most of the adherent cells present in a Passage 3 culture were fibroblastic in appearance. Thus, the presence of two progenitor cells in the protocols described herein out to Passage 4 is unusual. Furthermore, a clinical study using the two-cell type preparation was performed for treating feline chronic kidney disease (CKD). The pilot study resulted in a therapeutically beneficial outcome in approximately 70% of the study subjects. This very positive outcome was in contrast to other clinical studies using cultured cell preparations, which were based on cell preparations that contained only MSCs.

Chronic kidney disease is marked by injury to the epithelial layer in the nephron of the kidney. Prolonged exposure to a pro-inflammatory environment, which results when the epithelial layer is injured, contributes to the progressive pathology associated with chronic kidney disease. Thus, in the clinical study on CKD described herein, it would appear that the two-cell type preparation was able to reverse the progression of CKD, presumably by reducing inflammation, which is thought to be a key contributor to CKD.

One of the important properties of progenitor cells like MSCs is to mitigate pro-inflammatory environments through the secretion of a variety of biochemicals, including cytokines like IL-10, which act directly on a variety of immune cells that are associated with promoting an inflammatory reaction. This capability also is associated with broad-based immunomodulatory properties, like promoting the shift in macrophages from a pro-inflammatory type (M1) to an anti-inflammatory type (M2). The presence of MSC-like cells in the preparations described herein would support the mitigation of a pro-inflammatory environment associated with CKD and/or atopic dermatitis.

Apoptosis results when a cell (adult tissue cell, neutrophil, chondrocyte, etc.) receives a "signal" to alter its genome and adopt a programmed cell death. For example, alveolar epithelial cells when exposed to a suboptimal level of oxygen produce hypoxic-inducing factors, which lead to apoptosis of the alveolar epithelial cells and cell death. MSCs produce factors that are directly anti-apoptotic. The presence of MSC-like cells in the preparations described herein would support the rescue of tissue cells that had become apoptotic due to signals that were present in the site of pathology, like a pro-inflammatory nephron.

In addition to rescuing apoptotic cells, MSCs have been demonstrated to aid in the restoration of the activity of alveolar type II epithelial cells when those cells were impaired in a human lung injury model after the MSCs were delivered intratracheally. In the case of the feline CKD clinical trial and canine atopic dermatitis treatment, an epithelial stem cell-like cell was injected along with the mesenchymal-like stem cell. The combination might have reinforced the beneficial interaction of the MSC-type cell with epithelial cells present in the affected nephrons. In addition, the epithelial stem cell-like cells also could have responded to the epithelial niche by restoring the normal environment found in epithelial tissues, including the generation of TA cells, which could aid in the repairing and re-establishing a functional epithelial barrier in the nephron.

Another manifestation of stem cells supporting resident cells, is the secretion of biochemical factors, like Fibroblast Growth Factor (FGF), which are known to promote the proliferation of a wide variety of resident tissue cells. For example, chondrocyte proliferation is regulated in part by FGF when chondrocytes are injured, as occurs in osteoarthritis. FGF-2 promotes stromal-derived "stem cells" to form colonies and grow in culture, but this factor does not promote epithelial stem cell clonogenic activity. On the other hand, TGF-beta, EGF and PDGF-BB all promoted both epithelial and stromal cell clonogenicity. Epithelial cells are critical to the regeneration of endometrial "functionalis" layer (outer layer of the endometrium that gets released during a period). Re-epithelialization of the functionalis occurs within 24 hours, and those epithelial cells come from epithelial progenitor cells.

The fact that there are two types of cells present at Passage 4 in the therapeutic preparation used in the feline CKD and canine atopic dermatitis clinical trials described herein means that the two cell types have been co-cultured for an extended period of time, which could result in alterations in the two cell types due to "cross-talk". For example, adipose-derived MSCs formed acinar-like structures when cultured in medium that was conditioned by the growth of a human breast epithelial cell line. The resulting modified MSCs upregulated epithelial genes, indicating that the MSCs were influenced by factors released by the human breast epithelial cells. In a mixed co-culture experiment involving bone marrow-derived MSCs and alveolar epithelial cells, the alveolar cells maintained a Type II morphology, when normally Type II alveolar cells when grown on plastic will differentiate into Type I cells. Thus, MSCs and epithelial cells have been demonstrated to influence each other in in vitro experiments.

When cells are co-cultured together the cells can influence each other via the secretion of a multitude of biochemical factors. For example, when a cell line was established from mouse kidney tubuli, the epithelial cells when cultured in the presence of FGF-2, a cytokine that is secreted by MSCs, began to lose their reactivity for cytokeratin, which is a marker for epithelial cells, but gained reactivity for vimentin—a marker for mesenchymal stem cells, which the authors indicated might represent a known in vivo phenomenon called "epithelial to mesenchymal transition". Furthermore, the typical pattern in the case where multiple cell types are initially cultured, which includes MSCs, is that within a few passages the other types of cells disappear and the culture is dominated by MSCs.

Thus, the presence of cytokeratin-positive epithelial stem cell-like cells that also are CD44+ in the therapeutic preparations described herein suggests that the epithelial progenitor cells present at the initiation of the culture were able to influence the MSC-like progenitor cells in a manner that enable their survival through Passage 4 through a type of molecular cross-talk. The presence of epithelial progenitor cells in the therapeutic treatment used in the feline CKD clinical trial described herein might have provided a therapeutic benefit due to the critical role epithelial stem cells play in regenerating epithelial tissues, including regenerating the functionalis in the endometrium after shedding. The epithelial stem cell-like cells present in the therapeutic preparation also could aid in restoring the TA cell-dependent reparative mechanism fundamental to maintaining healthy epithelial tissues in the dysfunctional epithelial tissue of nephrons in CKD.

Finally, although the focus on potential cross-talk between the cells in co-culture has been on the role of biochemicals like IL-10, FGF and other cytokines, an important contributor to the communication occurring between the epithelial progenitor cell and the MSC-like cell is the exosome. Exosomes are produced by all cells in the body and released in vivo under very specific conditions. They are designed to contain "cargo", which consists of proteins, lipids, proteoglycans, RNA species and DNA, depending on the source of the exosome. Proteins carried as cargo in exosomes might include FGF or IL-10. Once the exosome binds to a cell, which might be considered as its "target" recipient, it will release its cargo. Mature proteins will be able to influence the target cell's metabolism right away. However, RNA components will integrate into the target cell's genome, or protein synthesis machinery and begin to produce proteins based on the exosome's cargo. Other types of RNA components (miRNA) might inhibit the activation of target cell genes, thereby changing the cell's production of proteins. Consequently, the influences of the two cell types present in the therapeutic preparations described herein on each other might include the intake of exosomes released in culture, which could modify the functional behavior of the cells during the co-culture period and subsequently when injected into the study subjects.

Cell Compositions

Some embodiments described herein relate to cell compositions comprising cells exhibiting certain properties. In some embodiments, the certain properties may include morphology (spindle shaped and cuboidal shaped) or expression of cell markers associated with mesenchymal or epithelial cell types (e.g. Vimentin, Cytokeratin-18, CD44, or CD326). In some embodiments, the cell compositions may comprise one or more populations of cells exhibiting certain properties. In some embodiments, the cell compositions may be heterogeneous cell compositions comprising more than one population of cells. In some embodiments, some populations of cells in the heterogeneous cell compositions may exhibit properties of more than one cell type.

Disclosed herein are heterogeneous cell compositions. In some embodiments, the heterogeneous cell compositions comprise a population of mesenchymal progenitor cells and a population of epithelial progenitor cells. In some embodiments, the mesenchymal progenitor cells and epithelial progenitor cells are co-cultured. In some embodiments, the mesenchymal progenitor cells and epithelial progenitor cells are obtained or derived from canine or feline uterine tissue. In some embodiments, the mesenchymal progenitor cells and epithelial progenitor cells are in a ratio of 20% to 80%, 40% to 60%, 50% to 50%, 60% to 40%, 80% to 20%, 90% to 10%, 99% to 1%, about 20% to about 80%, about 40% to about 60%, about 50% to about 50%, about 60% to about 40%, about 80% to 20%, about 90% to about 10%, or about 99% to about 1%, or a ratio within a range defined by any two of the aforementioned percentages. In some embodiments, the mesenchymal progenitor cells are present at a percentage of 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%, or any percentage within a range defined by any two of the aforementioned percentages, of the total number of cells of the heterogeneous cell composition. In some embodiments, the epithelial progenitor cells are present at a percentage of 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, or 60%, or any percentage within a range defined by any two of the aforementioned percentages, of the total number of cells of the heterogeneous cell composition. In some embodiments, the heterogeneous cell compositions further comprise fibroblast growth factor 2 (FGF-2). In some embodiments, the FGF-2 is recombinant human FGF-2. In some embodiments, the FGF2 is present at a concentration of 8 ng/mL or about 8 ng/mL. In some embodiments, the mesenchymal progenitor cells and epithelial progenitor cells are co-cultured in at least one tissue culture container that is not pre-treated with biological or synthetic coatings that enhance cell attachment and/or growth, including but not limited to cell-based feeder layers, polymers, proteins, polypeptides, peptides, antibodies, nucleic acids, DNA, RNA, sugars, polysaccharides, carbohydrates, lipids, poly-lysine, poly-ornithine, collagen, gelatin, fibronectin, vitronectin, laminin, elastin, tenascin, heparan sulfate, entactin, nidogen, osteopontin, extracellular matrix, basement membrane, Matrigel, hydrogel, PEI, WGA, hyaluronic acid, or any combination thereof. In some embodiments, the mesenchymal progenitor cells and epithelial progenitor cells are co-cultured in at least one tissue culture container for 3, 4, 5, or 6 passages, days, or culture intervals. In some embodiments, the uterine tissue is obtained from a spay procedure. In some embodiments, the heterogeneous cell compositions comprise 5 million, 6 million, 7 million, 8 million, 9 million, 10 million, 11 million, 12 million, 13 million, 14 million, 15 million, 16 million, 17 million, 18 million, 19 million, 20 million, 30 million, 40 million, 50 million, 60 million, 70 million, 80 million, 90 million, or 100 million or about 5 million, about 6 million, about 7 million, about 8 million, about 9 million, about 10 million, about 11 million, about 12 million, about 13 million, about 14 million, about 15 million, about 16 million, about 17 million, about 18 million, about 19 million, about 20 million, about 30 million, about 40 million, about 50 million, about 60 million, about 70 million, about 80 million, about 90 million, or about 100 million mesenchymal progenitor cells, or a number mesenchymal progenitor cells within a range defined by any two of the aforementioned numbers. In some embodiments, the heterogeneous cell compositions comprise 5 million, 6 million, 7 million, 8 million, 9 million, 10 million, 11 million, 12 million, 13 million, 14 million, 15 million, 16 million, 17 million, 18 million, 19 million, 20 million, 30 million, 40 million, 50 million, 60 million, 70 million, 80 million, 90 million, or 100 million or about 5 million, about 6 million, about 7 million, about 8 million, about 9 million, about 10 million, about 11 million, about 12 million, about 13 million, about 14 million, about 15 million, about 16 million, about 17 million, about 18 million, about 19 million, about 20 million, about 30 million, about 40 million, about 50 million, about 60 million, about 70 million, about 80 million, about 90 million, or about 100 million epithelial progenitor cells, or a number of epithelial progenitor cells within a range defined by any two of the aforementioned numbers. In some embodiments, the heterogeneous cell compositions comprise 5 million, 6 million, 7 million, 8 million, 9 million, 10 million, 11 million, 12 million, 13 million, 14 million, 15 million, 16 million, 17 million, 18 million, 19 million, 20 million, 30 million, 31 million, 32 million, 33 million, 34 million, 35 million, 36 million, 37 million, 38 million, 39 million, 40 million, 50 million, 60 million, 70 million, 80 million, 90 million, or 100 million or about 5 million, about 6 million, about 7 million, about 8 million, about 9 million, about 10 million, about 11 million, about 12 million, about 13 million, about 14 million, about 15 million, about 16 million, about 17 million, about 18 million, about 19 million, about 20 million, about 30 million, about 31 million, about 32 million, about 33 million, about 34 million, about 35 million, about 36 million, about 37 million, about 38 million, about 39 million, about 40 million, about 50 million, about 60 million, about 70 million, about 80 million, about 90 million, or about 100 million cells in total, or a number of cells in total within a range defined by any two of the aforementioned numbers. In some embodiments, the heterogeneous cell compositions comprise 30-36 million or about 30-36 million cells in total. In some embodiments, the heterogeneous cell compositions further comprise an additive, supplement, antibiotic, vitamin, growth factor, cryoprotectant, buffer, salt, protein, polypeptide, peptide, sugar, polysaccharide, or carbohydrate including but not limited to trehalose, DMSO, or albumin, or any combination thereof. In some embodiments, the heterogeneous cell compositions further comprise a population of cells, wherein each cell exhibits both mesenchymal progenitor cell and epithelial progenitor cell markers. In some embodiments, the mesenchymal progenitor cells and epithelial progenitor cells are obtained or derived from the same canine or feline uterine tissue. In some embodiments, the cell composition described herein e.g., a cell composition comprising a canine or feline cell, which is positive for both Vimentin and Cytokeratin-18, wherein the canine or feline cell is preferably a uterine-derived cell and/or a cell composition comprising any one or more of the heterogeneous cell populations described herein e.g., canine or feline cells, which are positive for Vimentin or Cytokeratin-18 and/or both markers, wherein the canine or feline cells are preferably uterine-derived cells, is prepared according to Protocol B, C, D, or a similar protocol. In some embodiments, the heterogeneous cell compositions further comprise a cryopreservation medium. In some embodiments, the cryopreservation medium comprises (a) CryoStor CS5 and/or BioLife Solutions CS10, (b) 98% Hespan and 2% DMSO, (c) about 98% Hespan and about 2% DMSO, (d) 2-10% DMSO and 2-20% FCS in a growth medium, or (e) about 2-10% DMSO and about 2-20% FCS in a growth medium. In some embodiments, the heterogeneous cell composition is further defined by a population of cells positive for both CD44 and CD326. In some embodiments, the population of cells positive for both CD44 and CD326 is found at a percentage of 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, or 30%, or any percentage within a range defined by any two of the aforementioned percentages, of the total number of the cells of the heterogeneous cell composition.

Also disclosed herein are heterogeneous cell compositions that comprise a population of vimentin-positive (V+)/cytokeratin-negative (C−) cells and a population of V+/cytokeratin-positive (C+) cells. In some embodiments, the V+/C− cells and V+/C+ cells are co-cultured. In some embodiments, the V+/C− cells and V+/C+ cells are obtained or derived from canine or feline uterine tissue. In some embodiments, the V+/C− cells and V+/C+ cells are in a ratio of 20% to 80%, 40% to 60%, 50% to 50%, 60% to 40%, 80% to 20%, 90% to 10%, 99% to 1%, about 20% to about 80%, about 40% to about 60%, about 50% to about 50%, about 60% to about 40%, about 80% to about 20%, about 90% to about 10%, or about 99% to about 1%, or a ratio within a range defined by any two of the aforementioned percentages. In some embodiments, the V+/C− cells are present at a percentage of 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%, or any percentage within a range defined by any two of the aforementioned percentages, of the total number of cells of the heterogeneous cell composition. In some embodiments, the V−/C+ cells are present at a percentage of 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, or 60%, or any percentage within a range defined by any two of the aforementioned percentages, of the total number of cells of the heterogeneous cell composition. In some embodiments, the heterogeneous cell compositions further comprise FGF-2. In some embodiments, the FGF-2 is recombinant human FGF-2. In some embodiments, the FGF-2 is at a concentration of 8 ng/mL or about 8 ng/mL. In some embodiments, the V+/C− cells and V+/C+ cells are co-cultured in at least one tissue culture container that is not pre-treated with biological or synthetic coatings that enhance cell attachment and/or growth, including but not limited to cell-based feeder layers, polymers, proteins, polypeptides, peptides, antibodies, nucleic acids, DNA, RNA, sugars, polysaccharides, carbohydrates, lipids, poly-lysine, poly-ornithine, collagen, gelatin, fibronectin, vitronectin, laminin, elastin, tenascin, heparan sulfate, entactin, nidogen, osteopontin, extracellular matrix, basement membrane, Matrigel, hydrogel, PEI, WGA, hyaluronic acid, or any combination thereof. In some embodiments, the V+/C− cells and V+/C+ cells are co-cultured in at least one tissue culture container for 3, 4, 5, or 6 passages, days, or culture intervals. In some embodiments, the uterine tissue is obtained from a spay procedure. In some embodiments, the heterogeneous cell composition comprises 5 million, 6 million, 7 million, 8 million, 9 million, 10 million, 11 million, 12 million, 13 million, 14 million, 15 million, 16 million, 17 million, 18 million, 19 million, 20 million, 30 million, 40 million, 50 million, 60 million, 70 million, 80 million, 90 million, or 100 million or about 5 million, about 6 million, about 7 million, about 8 million, about 9 million, about 10 million, about 11 million, about 12 million, about 13 million, about 14 million, about 15 million, about 16 million, about 17 million, about 18 million, about 19 million, about 20 million, about 30 million, about 40 million, about 50 million, about 60 million, about 70 million, about 80 million, about 90 million, or about 100 million V+/C− cells, or any number within a range defined by any two of the aforementioned numbers. In some embodiments, the heterogeneous cell composition comprises 5 million, 6 million, 7 million, 8 million, 9 million, 10 million, 11 million, 12 million, 13 million, 14 million, 15 million, 16 million, 17 million, 18 million, 19 million, 20 million, 30 million, 40 million, 50 million, 60 million, 70 million, 80 million, 90 million, or 100 million or about 5 million, about 6 million, about 7 million, about 8 million, about 9 million, about 10 million, about 11 million, about 12 million, about 13 million, about 14 million, about 15 million, about 16 million, about 17 million, about 18 million, about 19 million, about 20 million, about 30 million, about 40 million, about 50 million, about 60 million, about 70 million, about 80 million, about 90 million, or about 100 million V+/C+ cells, or any number within a range defined by any two of the aforementioned numbers. In some embodiments, the heterogeneous cell compositions comprise 5 million, 6 million, 7 million, 8 million, 9 million, 10 million, 11 million, 12 million, 13 million, 14 million, 15 million, 16 million, 17 million, 18 million, 19 million, 20 million, 30 million, 31 million, 32 million, 33 million, 34 million, 35 million, 36 million, 37 million, 38 million, 39 million, 40 million, 50 million, 60 million, 70 million, 80 million, 90 million, or 100 million or about 5 million, about 6 million, about 7 million, about 8 million, about 9 million, about 10 million, about 11 million, about 12 million, about 13 million, about 14 million, about 15 million, about 16 million, about 17 million, about 18 million, about 19 million, about 20 million, about 30 million, about 31 million, about 32 million, about 33 million, about 34 million, about 35 million, about 36 million, about 37 million, about 38 million, about 39 million, about 40 million, about 50 million, about 60 million, about 70 million, about 80 million, about 90 million, or about 100 million cells in total, or a number of cells in total within a range defined by any two of the aforementioned numbers. In some embodiments, the heterogeneous cell compositions comprise 30-36 million or about 30-36 million cells in total. In some embodiments, the heterogeneous cell composition further comprises an additive, supplement, antibiotic, vitamin, growth factor, cryoprotectant, buffer, salt, protein, polypeptide, peptide, sugar, polysaccharide, or carbohydrate including but not limited to trehalose, DMSO, or albumin, or any combination thereof. In some embodiments, the V+/C− cells and V+/C+ cells are obtained or derived from the same canine or feline uterine tissue. In some embodiments, the cell composition described herein e.g., a cell composition comprising a canine or feline cell, which is positive for both Vimentin and Cytokeratin-18, wherein the canine or feline cell is preferably a uterine-derived cell and/or a cell composition comprising any one or more of the heterogeneous cell populations described herein e.g., canine or feline cells, which are positive for Vimentin or Cytokeratin-18 and/or both markers, wherein the canine or feline cells are preferably uterine-derived cells, is prepared according to Protocol B, C, or D or a similar protocol. In some embodiments, the heterogeneous cell composition further comprises a cryopreservation medium. In some embodiments, the cryopreservation medium comprises (a) CryoStor CS5 and/or BioLife Solutions CS10, (b) 98% Hespan and 2% DMSO, (c) about 98% Hespan and about 2% DMSO, (d) 2-10% DMSO and 2-20% FCS in a growth medium, or (e) about 2-10% DMSO and about 2-20% FCS in a growth medium. In some embodiments, the heterogeneous cell composition is further defined by a population of cells positive for both CD44 and CD326. In some embodiments, the population of cells positive for both CD44 and CD326 is found at a percentage of 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, or 30%, or any percentage within a range defined by any two of the aforementioned percentages, of the total number of the cells of the heterogeneous cell composition.

Also disclosed herein are heterogeneous cell compositions. In some embodiments, the heterogeneous cell compositions comprise (a) a population of vimentin-positive (V+)/cytokeratin-negative (C−) cells, (b) a population of vimentin-negative (V−)/cytokeratin-positive (C+) cells, and (c) a population of V+/C+ cells. In some embodiments, the populations of (a)-(c) are co-cultured. In some embodiments, the populations of (a)-(c) are obtained or derived from canine or feline uterine tissue. In some embodiments, the population of V+/C+ cells is found at a percentage of 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, or 30%, or any percentage within a range defined by any two of the aforementioned percentages, of the total number of the cells of the heterogeneous cell composition. In some embodiments, the population of V+/C− cells is found at a percentage of 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%, or any percentage within a range defined by any two of the aforementioned percentages, of the total number of cells of the heterogeneous cell composition. In some embodiments, the population of V−/C+ cells is found at a percentage of 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, or 60%, or any percentage within a range defined by any two of the aforementioned percentages, of the total number of cells of the heterogeneous cell composition. In some embodiments, the population of V+/C− cells and the population of V−/C+ cells are in a ratio of 20% to 80%, 40% to 60%, 50% to 50%, 60% to 40%, 80% to 20%, 90% to 10%, 99% to 1%, about 20% to about 80%, about 40% to about 60%, about 50% to about 50%, about 60% to about 40%, about 80% to about 20%, about 90% to about 10%, about 99% to about 1%, or a ratio within a range defined by any two of the aforementioned percentages. In some embodiments, the heterogeneous cell composition further comprises FGF-2. In some embodiments, the FGF-2 is recombinant human FGF-2. In some embodiments, the FGF-2 is at a concentration of 8 ng/mL or about 8 ng/mL. In some embodiments, the populations of (a)-(c) are co-cultured in at least one tissue culture container that is not pre-treated with biological or synthetic coatings that enhance cell attachment and/or growth, including but not limited to cell-based feeder layers, polymers, proteins, polypeptides, peptides, antibodies, nucleic acids, DNA, RNA, sugars, polysaccharides, carbohydrates, lipids, polylysine, poly-ornithine, collagen, gelatin, fibronectin, vitronectin, laminin, elastin, tenascin, heparan sulfate, entactin, nidogen, osteopontin, extracellular matrix, basement membrane, Matrigel, hydrogel, PEI, WGA, hyaluronic acid, or any combination thereof. In some embodiments, the populations of (a)-(c) are co-cultured in at least one tissue culture container for 3, 4, 5, or 6 passages, days, or culture intervals. In some embodiments, the uterine tissue is obtained from a spay procedure. In some embodiments, the heterogeneous cell compositions comprise 5 million, 6 million, 7 million, 8 million, 9 million, 10 million, 11 million, 12 million, 13 million, 14 million, 15 million, 16 million, 17 million, 18 million, 19 million, 20 million, 30 million, 40 million, 50 million, 60 million, 70 million, 80 million, 90 million, or 100 million or about 5 million, about 6 million, about 7 million, about 8 million, about 9 million, about 10 million, about 11 million, about 12 million, about 13 million, about 14 million, about 15 million, about 16 million, about 17 million, about 18 million, about 19 million, about 20 million, about 30 million, about 40 million, about 50 million, about 60 million, about 70 million, about 80 million, about 90 million, or about 100 million V+/C− cells, or any number within a range defined by any two of the aforementioned numbers. In some embodiments, the heterogeneous cell compositions comprise 5 million, 6 million, 7 million, 8 million, 9 million, 10 million, 11 million, 12 million, 13 million, 14 million, 15 million, 16 million, 17 million, 18 million, 19 million, 20 million, 30 million, 40 million, 50 million, 60 million, 70 million, 80 million, 90 million, or 100 million or about 5 million, about 6 million, about 7 million, about 8 million, about 9 million, about 10 million, about 11 million, about 12 million, about 13 million, about 14 million, about 15 million, about 16 million, about 17 million, about 18 million, about 19 million, about 20 million, about 30 million, about 40 million, about 50 million, about 60 million, about 70 million, about 80 million, about 90 million, or about 100 million V−/C+ cells, or any number within a range defined by any two of the aforementioned numbers. In some embodiments, the heterogeneous cell compositions comprise 5 million, 6 million, 7 million, 8 million, 9 million, 10 million, 11 million, 12 million, 13 million, 14 million, 15 million, 16 million, 17 million, 18 million, 19 million, 20 million, 30 million, 40 million, 50 million, 60 million, 70 million, 80 million, 90 million, or 100 million or about 5 million, about 6 million, about 7 million, about 8 million, about 9 million, about 10 million, about 11 million, about 12 million, about 13 million, about 14 million, about 15 million, about 16 million, about 17 million, about 18 million, about 19 million, about 20 million, about 30 million, about 40 million, about 50 million, about 60 million, about 70 million, about 80 million, about 90 million, or about 100 million V+/C+ cells, or any number within a range defined by any two of the aforementioned numbers. In some embodiments, the heterogeneous cell compositions comprise 5 million, 6 million, 7 million, 8 million, 9 million, 10 million, 11 million, 12 million, 13 million, 14 million, 15 million, 16 million, 17 million, 18 million, 19 million, 20 million, 30 million, 31 million, 32 million, 33 million, 34 million, 35 million, 36 million, 37 million, 38 million, 39 million, 40 million, 50 million, 60 million, 70 million, 80 million, 90 million, or 100 million or about 5 million, about 6 million, about 7 million, about 8 million, about 9 million, about 10 million, about 11 million, about 12 million, about 13 million, about 14 million, about 15 million, about 16 million, about 17 million, about 18 million, about 19 million, about 20 million, about 30 million, about 31 million, about 32 million, about 33 million, about 34 million, about 35 million, about 36 million, about 37 million, about 38 million, about 39 million, about 40 million, about 50 million, about 60 million, about 70 million, about 80 million, about 90 million, or about 100 million cells in total, or a number of cells in total within a range defined by any two of the aforementioned numbers. In some embodiments, the heterogeneous cell compositions comprise 30-36 million or about 30-36 million cells in total. In some embodiments, the heterogeneous cell composition is further defined by a population of cells positive for both CD44 and CD326. In some embodiments, the population of cells positive for both CD44 and CD326 is found at a percentage of 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, or 30%, or any percentage within a range defined by any two of the aforementioned percentages, of the total number of the cells of the heterogeneous cell composition. In some embodiments, the heterogeneous cell compositions further comprise an additive, supplement, antibiotic, vitamin, growth factor, cryoprotectant, buffer, salt, protein, polypeptide, peptide, sugar, polysaccharide, or carbohydrate including but not limited to trehalose, DMSO, or albumin, or any combination thereof. In some embodiments, the populations of (a)-(c) are obtained or derived from the same canine or feline uterine tissue. In some embodiments, the cell composition described herein e.g., a cell composition comprising a canine or feline cell, which is positive for both Vimentin and Cytokeratin-18, wherein the canine or feline cell is preferably a uterine-derived cell and/or a cell composition comprising any one or more of the heterogeneous cell populations described herein e.g., canine or feline cells, which are positive for Vimentin or Cytokeratin-18 and/or both markers, wherein the canine or feline cells are preferably uterine-derived cells, is prepared according to Protocol B, C, or D, or a similar protocol. In some embodiments, the heterogeneous cell compositions further comprise a cryopreservation medium. In some embodiments, the cryopreservation medium comprises (a) CryoStor CS5 and/or BioLife Solutions CS10, (b) 98% Hespan and 2% DMSO, (c) about 98% Hespan and about 2% DMSO, (d) 2-10% DMSO and 2-20% FCS in a growth medium, or (e) about 2-10% DMSO and about 2-20% FCS in a growth medium.

Also disclosed herein are cell compositions. In some embodiments, the cell composition comprises a canine or feline cell, which is positive for both Vimentin and Cytokeratin-18. In some embodiments, the canine or feline cell is a uterine cell. In some embodiments, the cell composition further comprises mesenchymal progenitor cells and/or epithelial progenitor cells. In some embodiments, the cell composition further comprises V+/C− and/or V−/C+ cells. In some embodiments, the canine or feline cells are obtained or derived from canine or feline uterine tissue. In some embodiments, the canine or feline cells are obtained or derived from a spay procedure. In some embodiments, the cell composition further comprises FGF-2. In some embodiments, the FGF-2 is recombinant human FGF-2. In some embodiments, the FGF-2 is at a concentration of 8 ng/mL or about 8 ng/mL. In some embodiments, the cell composition is co-cultured in at least one tissue culture container that is not pre-treated with biological or synthetic coatings that enhance cell attachment and/or growth, including but not limited to cell-based feeder layers, polymers, proteins, polypeptides, peptides, antibodies, nucleic acids, DNA, RNA, sugars, polysaccharides, carbohydrates, lipids, poly-lysine, poly-ornithine, collagen, gelatin, fibronectin, vitronectin, laminin, elastin, tenascin, heparan sulfate, entactin, nidogen, osteopontin, extracellular matrix, basement membrane, Matrigel, hydrogel, PEI, WGA, hyaluronic acid, or any combination thereof. In some embodiments, the cell composition is cultured in at least one tissue culture container for 3, 4, 5, or 6 passages, days, or culture intervals. In some embodiments, the cell composition comprises 5 million, 6 million, 7 million, 8 million, 9 million, 10 million, 11 million, 12 million, 13 million, 14 million, 15 million, 16 million, 17 million, 18 million, 19 million, 20 million, 30 million, 40 million, 50 million, 60 million, 70 million, 80 million, 90 million, or 100 million or about 5 million, about 6 million, about 7 million, about 8 million, about 9 million, about 10 million, about 11 million, about 12 million, about 13 million, about 14 million, about 15 million, about 16 million, about 17 million, about 18 million, about 19 million, about 20 million, about 30 million, about 40 million, about 50 million, about 60 million, about 70 million, about 80 million, about 90 million, or about 100 million of the canine or feline cells that are positive for both Vimentin and Cytokeratin-18, or any number of cells within a range defined by any two of the aforementioned number of cells. In some embodiments, the cell composition further comprises an additive, supplement, antibiotic, vitamin, growth factor, cryoprotectant, buffer, salt, protein, polypeptide, peptide, sugar, polysaccharide, or carbohydrate including but not limited to trehalose, DMSO, or albumin, or any combination thereof. In some embodiments, the cell composition comprises 30-36 million or about 30-36 million cells in total. In some embodiments, the cell composition is further defined by a population of cells positive for both CD44 and CD326. In some embodiments, the cell composition described herein e.g., a cell composition comprising a canine or feline cell, which is positive for both Vimentin and Cytokeratin-18, wherein the canine or feline cell is preferably a uterine-derived cell and/or a cell composition comprising any one or more of the heterogeneous cell populations described herein e.g., canine or feline cells, which are positive for Vimentin or Cytokeratin-18 and/or both markers, wherein the canine or feline cells are preferably uterine-derived cells, is prepared according to Protocol B, C, or D, or a similar protocol. In some embodiments, the cell compositions further comprises a cryopreservation medium. In some embodiments, the cryopreservation medium comprises (a) CryoStor CS5 and/or BioLife Solutions CS10, (b) 98% Hespan and 2% DMSO, (c) about 98% Hespan and about 2% DMSO, (d) 2-10% DMSO and 2-20% FCS in a growth medium, or (e) about 2-10% DMSO and about 2-20% FCS in a growth medium.

Some embodiments described herein relate to pharmaceutical compositions that comprise, consist essentially of, or consist of an effective amount of a cell composition described herein and a pharmaceutically acceptable carrier, excipient, or combination thereof. A pharmaceutical composition described herein is suitable for human and/or veterinary applications. The pharmaceutical compound can also be administered in a local rather than systemic manner, for example, via injection of the compound directly into an organ, tissue, cancer, tumor, infected area, or otherwise diseased region.

Methods of Making

Disclosed herein are methods of preparing a cell composition. In some embodiments, the methods comprise contacting a single cell suspension comprising mesenchymal progenitor cells and epithelial progenitor cells with FGF-2 and culturing the single cell suspension with FGF-2 for 3, 4, 5, or 6 passages, days, or culture intervals. In some embodiments, the cell composition is any one of the cell compositions or heterogeneous cell compositions disclosed herein. In some embodiments, the single cell suspension is obtained or derived from canine or feline tissue. In some embodiments, at the end of 3, 4, 5, or 6 passages, days, or culture intervals, the mesenchymal progenitor cells and epithelial progenitor cells are in a ratio of 20% to 80%, 40% to 60%, 50% to 50%, 60% to 40%, 80% to 20%, 90% to 10%, 99% to 1%, about 20% to about 80%, about 40% to about 60%, about 50% to about 50%, about 60% to about 40%, about 80% to about 20%, about 90% to about 10%, or about 99% to about 1%, or a ratio within a range defined by any two of the aforementioned percentages. In some embodiments, the mesenchymal progenitor cells are present at a percentage of 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%, or any percentage within a range defined by any two of the aforementioned percentages, of the total number of cells of the heterogeneous cell composition. In some embodiments, the epithelial progenitor cells are present at a percentage of 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, or 60%, or any percentage within a range defined by any two of the aforementioned percentages, of the total number of cells of the heterogeneous cell composition. In some embodiments, the single cell suspension is passaged when the cell culture reaches 70-80% confluence. In some embodiments, the single cell suspension is obtained or derived from the same canine or feline uterine tissue. In some embodiments, the cell composition described herein e.g., a cell composition comprising a canine or feline cell, which is positive for both Vimentin and Cytokeratin-18, wherein the canine or feline cell is preferably a uterine-derived cell and/or a cell composition comprising any one or more of the heterogeneous cell populations described herein e.g., canine or feline cells, which are positive for Vimentin or Cytokeratin-18 and/or both markers, wherein the canine or feline cells are preferably uterine-derived cells, is prepared according to Protocol B, C, or D, or a similar protocol. In some embodiments, the canine or feline uterine tissue is enzymatically dissociated to form the single cell suspension. In some embodiments, the FGF-2 is recombinant human FGF-2. In some embodiments, the FGF-2 is at a concentration of 8 ng/mL or about 8 ng/mL. In some embodiments, the single cell suspension is cultured for at least 4 passages, days, or culture intervals. In some embodiments, the heterogeneous cell composition is further defined by a population of cells positive for both CD44 and CD326. In some embodiments, the population of cells positive for both CD44 and CD326 is found at a percentage of 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, or 30%, or any percentage within a range defined by any two of the aforementioned percentages, of the total number of the cells of the heterogeneous cell composition.

Also disclosed herein are methods of preparing a cell composition. In some embodiments, the methods comprise contacting a single cell suspension comprising V+/C− cells and V+/C+ cells with FGF-2, and culturing the single cell suspension with FGF-2 for 3, 4, 5, or 6 passages, days, or culture intervals. In some embodiments, the cell composition is any one of the cell compositions or heterogeneous cell compositions disclosed herein. In some embodiments, the single cell suspension is obtained or derived from canine or feline tissue. In some embodiments, at the end of 3, 4, 5 or 6 passages, days, or culture intervals, the V+/C− cells and V+/C+ cells are in a ratio of 20% to 80%, 40% to 60%, 50% to 50%, 60% to 40%, 80% to 20%, 90% to 10%, 99% to 1%, about 20% to about 80%, about 40% to about 60%, about 50% to about 50%, about 60% to about 40%, about 80% to about 20%, about 90% to about 10%, or about 99% to about 1%, or a ratio within a range defined by any two of the aforementioned percentages. In some embodiments, the V+/C− cells are present at a percentage of 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%, or any percentage within a range defined by any two of the aforementioned percentages, of the total number of cells of the heterogeneous cell composition. In some embodiments, the V−/C+ cells are present at a percentage of 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, or 60%, or any percentage within a range defined by any two of the aforementioned percentages, of the total number of cells of the heterogeneous cell composition. In some embodiments, the single cell suspension is passaged when the cell culture reaches 70-80% confluence. In some embodiments, the single cell suspension is obtained or derived from the same canine or feline uterine tissue. In some embodiments, the cell composition described herein e.g., a cell composition comprising a canine or feline cell, which is positive for both Vimentin and Cytokeratin-18, wherein the canine or feline cell is preferably a uterine-derived cell and/or a cell composition comprising any one or more of the heterogeneous cell populations described herein e.g., canine or feline cells, which are positive for Vimentin or Cytokeratin-18 and/or both markers, wherein the canine or feline cells are preferably uterine-derived cells, is prepared according Protocol B, C, or D, or a similar protocol. In some embodiments, the canine or feline uterine tissue is enzymatically dissociated to form the single cell suspension. In some embodiments, the FGF-2 is recombinant human FGF-2. In some embodiments, the FGF-2 is at a concentration of 8 ng/mL or about 8 ng/mL. In some embodiments, the single cell suspension is cultured for at least 4 passages, days, or culture intervals. In some embodiments, the heterogeneous cell composition is further defined by a population of cells positive for both CD44 and CD326. In some embodiments, the population of cells positive for both CD44 and CD326 is found at a percentage of 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, or 30%, or any percentage within a range defined by any two of the aforementioned percentages, of the total number of the cells of the heterogeneous cell composition.

Also disclosed herein are methods of preparing a cell composition such as a heterogeneous cell composition. In some embodiments, the cell composition described herein e.g., a cell composition comprising a canine or feline cell, which is positive for both Vimentin and Cytokeratin-18, wherein the canine or feline cell is preferably a uterine-derived cell and/or a cell composition comprising any one or more of the heterogeneous cell populations described herein e.g., canine or feline cells, which are positive for Vimentin or Cytokeratin-18 and/or both markers, wherein the canine or feline cells are preferably uterine-derived cells, is prepared according to Protocol B, C, or D, or a similar protocol. In some embodiments, the methods comprise dissociating canine or feline uterine tissue into a single cell suspension and culturing the single cell suspension for 3, 4, 5 or 6 passages, days, or culture intervals, thereby preparing the heterogeneous cell composition from the cultured single cell suspension. In some embodiments, at the end of the 3, 4, 5 or 6 passages, days, or culture intervals, the heterogeneous cell composition comprises a population of cells positive for both Vimentin and Cytokeratin-18. In some embodiments, the population of cells positive for both Vimentin and Cytokeratin-18 is found at a percentage of 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, or 30%, or any percentage within a range defined by any two of the aforementioned percentages, of the total number of the cells of the heterogeneous cell composition. In some embodiments, the single cell suspension is passaged when the cell culture reaches 70-80% confluence. In some embodiments, the heterogeneous cell composition is any one of the heterogeneous cell compositions disclosed herein. In some embodiments, the dissociating step comprises enzymatic dissociation. In some embodiments, the enzymatic dissociation comprises contacting the canine or feline uterine tissue with trypsin, chymotrypsin, collagenase, papain, hyaluronidase, elastase, thermolysin, neutral protease, or any combination thereof. In some embodiments, the single cell suspension is cultured with FGF-2. In some embodiments, the FGF-2 is recombinant human FGF-2. In some embodiments, the FGF-2 is at a concentration of 8 ng/mL or about 8 ng/mL. In some embodiments, the single cell suspension is cultured for at least 4 passages, days, or culture intervals. In some embodiments, the heterogeneous cell composition is further defined by a population of cells positive for both CD44 and CD326. In some embodiments, the population of cells positive for both CD44 and CD326 is found at a percentage of 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, or 30%, or any percentage within a range defined by any two of the aforementioned percentages, of the total number of the cells of the heterogeneous cell composition.

METHODS OF USE

The terms "treating," "treatment," "therapeutic," or "therapy" as used herein has its ordinary meaning as understood in light of the specification, and do not necessarily mean total cure or abolition of the disease or condition. The term "treating" or "treatment" as used herein (and as well understood in the art) also means an approach for obtaining beneficial or desired results in a subject's condition, including clinical results. Beneficial or desired clinical results can include, but are not limited to, alleviation or amelioration of one or more symptoms or conditions, diminishment of the extent of a disease, stabilizing (i.e., not worsening) the state of disease, prevention of a disease's transmission or spread, delaying or slowing of disease progression, amelioration or palliation of the disease state, diminishment of the reoccurrence of disease, and remission, whether partial or total and whether detectable or undetectable. "Treating" and "treatment" as used herein also include prophylactic treatment. Treatment methods comprise administering to a subject a therapeutically effective amount of an active agent. The administering step may consist of a single administration or may comprise a series of administrations. The compositions are administered to the subject in an amount and for a duration sufficient to treat the patient. The length of the treatment period depends on a variety of factors, such as the severity of the condition, the age and genetic profile of the patient, the concentration of active agent, the activity of the compositions used in the treatment, or a combination thereof. It will also be appreciated that the effective dosage of an agent used for the treatment or prophylaxis may increase or decrease over the course of a particular therapy or prophylaxis regime. Changes in dosage may result and become apparent by standard diagnostic assays known in the art. In some instances, chronic administration may be required.

As used herein, the term "combination therapy" is intended to define therapies which comprise the use of a combination of two or more pharmaceutical compositions/agents or therapies. Thus, references to "combination therapy", "combinations" and the use of compositions/agents "in combination" in this application may refer to compositions/agents that are administered as part of the same overall treatment regimen. As such, the dosage or timing of each of the two or more compositions/agents may differ: each may be administered at the same time or at different times. Accordingly, the compositions/agents of the combination may be administered sequentially (e.g. before or after) or simultaneously, either in the same pharmaceutical formulation (i.e. together), or in different pharmaceutical formulations (i.e. separately). Each of the two or more compositions/agents in a combination therapy may also differ with respect to the route of administration.

A subject, such as a canine or feline subject, may have a certain disease or condition. Alternatively, the subject may be on the onset of getting the disease or condition, at risk of getting the disease or condition, previously had the disease or condition, or does not have the disease or condition. The disease or condition may be idiopathic or related to an autoimmune disease or aging. The disease or condition may include but is not limited to chronic kidney disease, atopic dermatitis, immune mediated arthritis, hepatitis, liver disease, inflammatory bowel disease, osteoarthritis, intravertebral disc disease, keratoconjunctivitis sicca (dry eye), pancreatitis, fibrosis, sclerosis, amyloidosis, immune mediated polyarthritis or a wound. At least one heterogeneous cell composition described herein is administered to the subject.

In some embodiments, the at least one heterogeneous cell composition may be administered enterally or parenterally. In some embodiments, the at least one heterogeneous cell composition may be administered intravenously, intraarterially, subcutaneously, intramuscularly, intradermally, intrathecally, intraperitoneally, intraportally, intra-articularly, intraocularly or intrarenally, or any combination thereof. In some embodiments, the at least one heterogeneous cell composition may comprise 5 million, 6 million, 7 million, 8 million, 9 million, 10 million, 11 million, 12 million, 13 million, 14 million, 15 million, 16 million, 17 million, 18 million, 19 million, 20 million, 21 million, 22 million, 23 million, 24 million, 25 million, 26 million, 27 million, 28 million, 29 million, 30 million, 31 million, 32 million, 33 million, 34 million, 35 million, 36 million, 37 million, 38 million, 39 million, 40 million, 45 million, 50 million, 60 million, 70 million, 80 million, 90 million, or 100 million, or about 5 million, about 6 million, about 7 million, about 8 million, about 9 million, about 10 million, about 11 million, about 12 million, about 13 million, about 14 million, about 15 million, about 16 million, about 17 million, about 18 million, about 19 million, about 20 million, about 21 million, about 23 million, about 24 million, about 25 million, about 26 million, about 27 million, about 28 million, about 29 million, about 30 million, about 31 million, about 32 million, about 33 million, about 34 million, about 35 million, about 36 million, about 37 million, about 38 million, about 39 million, about 40 million, about 45 million, about 50 million cells, about 60 million, about 70 million, about 80 million, about 90 million, about or 100 million cells, or any number within a range defined by any two of the aforementioned numbers. In some embodiments, the at least one heterogeneous cell composition comprises 30 million, 31 million, 32 million, 33 million, 34 million, 35 million, 36 million cells, about 30 million cells, about 31 million cells, about 32 million cells, about 33 million cells, about 34 million cells, about 35 million cells, or about 36 million cells, or any number of cells within a range defined by any two of the aforementioned number of cells. In some embodiments, the at least one heterogeneous cell composition may be administered in 1, 2, 3, 4, 5, 6, 7, 8, 9, or 10 doses. In some embodiments, each dose may be administered 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 days, or 1, 2, 3, 4, 5, 6, 7, 8, 9, 10, 11, 12 months, or 1, 2, 3, 4, 5 years following the previous dose. In some embodiments, the subject experiences a relief in symptoms or full or partial reduction in the disease following administration of the at least one heterogeneous cell composition.

Also disclosed herein are methods of treating, inhibiting, or ameliorating chronic kidney disease, atopic dermatitis, immune mediated arthritis, hepatitis, liver disease, inflammatory bowel disease, osteoarthritis, intravertebral disc disease, keratoconjunctivitis sicca (dry eye), pancreatitis, fibrosis, sclerosis, amyloidosis, immune mediated polyarthritis or wounds in a canine or feline subject in need thereof. In some embodiments, the methods comprise providing at least one heterogeneous cell composition comprising a population of mesenchymal progenitor cells and a population of epithelial progenitor cells, wherein the mesenchymal progenitor cells and epithelial progenitor cells are obtained or derived from canine or feline uterine tissue and wherein the canine or feline uterine tissue is autologous or allogeneic to the canine or feline subject and administering the at least one heterogeneous cell composition to the canine or feline subject. In some embodiments, the mesenchymal progenitor cells and epithelial progenitor cells are in a ratio of 20% to 80%, 40% to 60%, 50% to 50%, 60% to 40%, 80% to 20%, 90% to 10%, 99% to 1%, about 20% to about 80%, about 40% to about 60%, about 50% to about 50%, about 60% to about 40%, about 80% to about 20%, about 90% to about 10%, or about 99% to about 1%, or a ratio within a range defined by any two of the aforementioned percentages. In some embodiments, the mesenchymal progenitor cells are present at a percentage of 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%, or any percentage within a range defined by any two of the aforementioned percentages, of the total number of cells of the at least one heterogeneous cell composition. In some embodiments, the epithelial progenitor cells are present at a percentage of 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, or 60%, or any percentage within a range defined by any two of the aforementioned percentages, of the total number of cells of the at least one heterogeneous cell composition. In some embodiments, the at least one heterogeneous cell composition is administered intravenously, intraarterially, subcutaneously, intramuscularly, intradermally, intrathecally, intraperitoneally, intraportally, intra-articularly, intraocularly or intrarenally, or any combination thereof. In some embodiments, the at least one heterogeneous cell composition is thawed from a cryopreserved state and transferred to a delivery device or container, such as a syringe, comprising a suitable buffer, diluent or fluid, such as saline, Ringer's acetate solution, dextrose solution, phosphate buffered saline or lactated Ringer's solution, before administration. In some embodiments, thawing the at least one heterogeneous cell composition from the cryopreserved state comprises diluting the at least one heterogeneous cell composition by 1.5×, 2×, 3×, 4×, 5×, 6×, 7×, 8×, 9×, 10×, or at least 1.5×, 2×, 3×, 4×, 5×, 6×, 7×, 8×, 9×, or 10×. In some embodiments, the at least one heterogeneous cell composition is any one of the heterogeneous cell compositions disclosed herein. In some embodiments, the cell composition described herein e.g., a cell composition comprising a canine or feline cell, which is positive for both Vimentin and Cytokeratin-18, wherein the cells are preferably uterine cells, and/or a cell composition comprising any one or more of the heterogeneous cell populations described herein e.g., canine or feline cells, which are positive for Vimentin or Cytokeratin-18 and/or both markers, preferably uterine cells, wherein the cell composition is prepared according to Protocol B, C, or D, or a similar protocol.

Also disclosed herein are methods of treating, inhibiting, or ameliorating chronic kidney disease, atopic dermatitis, immune mediated arthritis, hepatitis, liver disease, inflammatory bowel disease, osteoarthritis, intravertebral disc disease, keratoconjunctivitis sicca (dry eye), pancreatitis, fibrosis, sclerosis, amyloidosis, immune mediated polyarthritis, or wounds in a canine or feline subject in need thereof. In some embodiments, the methods comprise providing at least one heterogeneous cell composition comprising a population of V+/C− cells and a population of V+/C+ cells, wherein the V+/C− cells and V+/C+ cells are obtained or derived from canine or feline uterine tissue and wherein the canine or feline uterine tissue is autologous or allogeneic to the canine or feline subject and administering the at least one heterogeneous cell composition to the canine or feline subject. In some embodiments, the V+/C− cells and V+/C+ cells are in a ratio of 20% to 80%, 40% to 60%, 50% to 50%, 60% to 40%, 80% to 20%, 90% to 10%, 99% to 1%, about 20% to about 80%, about 40% to about 60%, about 50% to about 50%, about 60% to about 40%, about 80% to about 20%, about 90% to about 10%, or about 99% to about 1%, or a ratio within a range defined by any two of the aforementioned percentages. In some embodiments, the population of V+/C− cells is present at a percentage of 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%, or any percentage within a range defined by any two of the aforementioned percentages, of the total number of cells of the at least one heterogeneous cell composition. In some embodiments, the population of V−/C+ cells is present at a percentage of 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, or 60%, or any percentage within a range defined by any two of the aforementioned percentages, of the total number of cells of the at least one heterogeneous cell composition. In some embodiments, the at least one heterogeneous cell composition is thawed from a cryopreserved state and transferred to a delivery device or container, such as a syringe, comprising a suitable buffer, diluent or fluid, such as saline, Ringer's acetate solution, dextrose solution, phosphate buffered saline or lactated Ringer's solution, before administration. In some embodiments, thawing the at least one heterogeneous cell composition from the cryopreserved state comprises diluting the at least one heterogeneous cell composition by 1.5×, 2×, 3×, 4×, 5×, 6×, 7×, 8×, 9×, 10×, or at least 1.5×, 2×, 3×, 4×, 5×, 6×, 7×, 8×, 9×, or 10×. In some embodiments, the at least one heterogeneous cell composition is any one of the heterogeneous cell compositions disclosed herein. In some embodiments, the cell composition described herein e.g., a cell composition comprising a canine or feline cell, which is positive for both Vimentin and Cytokeratin-18, wherein the canine or feline cells are preferably uterine-derived cells, and/or a cell composition comprising any one or more of the heterogeneous cell populations described herein e.g., canine or feline cells, which are positive for Vimentin or Cytokeratin-18 and/or both markers, wherein the canine or feline cells are preferably uterine-derived cells, is prepared according to Protocol B, C, or D, or a similar protocol.

Also disclosed herein are methods of treating, inhibiting, or ameliorating chronic kidney disease, atopic dermatitis, immune mediated arthritis, hepatitis, liver disease, inflammatory bowel disease, osteoarthritis, intravertebral disc disease, keratoconjunctivitis sicca (dry eye), pancreatitis, fibrosis, sclerosis, amyloidosis, immune mediated polyarthritis, or wounds in a canine or feline subject in need thereof. In some embodiments, the methods comprise administering at least one cell composition, preferably a heterogeneous cell composition, to the canine or feline subject. In some embodiments, the at least one cell composition, preferably a heterogeneous cell composition, comprises a population of cells, which are positive for both Vimentin and Cytokeratin-18. In some embodiments, the at least one heterogeneous cell composition is any one of the heterogeneous cell compositions disclosed herein. In some embodiments, the population of cells positive for both Vimentin and Cytokeratin-18 is present at a percentage of 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, or 30%, or any percentage within a range defined by any two of the aforementioned percentages, of the total number of the cells of the heterogeneous cell composition. In some embodiments, the heterogeneous cell composition is further defined by a population of cells positive for both CD44 and CD326. In some embodiments, the population of cells positive for both CD44 and CD326 is found at a percentage of 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, or 30%, or any percentage within a range defined by any two of the aforementioned percentages, of the total number of the cells of the heterogeneous cell composition. In some embodiments, the heterogeneous cell composition is autologous or allogeneic to the canine or feline subject. In some embodiments, the at least one heterogeneous cell composition is administered intravenously, intraarterially, subcutaneously, intramuscularly, intradermally, intrathecally, intraperitoneally, intraportally, intra-articularly, intraocularly or intrarenally, or any combination thereof. In some embodiments, the at least one heterogeneous cell composition is thawed from a cryopreserved state and transferred to a delivery device or container, such as a syringe, comprising a suitable buffer, diluent or fluid, such as saline, Ringer's acetate solution, dextrose solution, phosphate buffered saline or lactated Ringer's solution, before administration. In some embodiments, thawing the at least one heterogeneous cell composition from the cryopreserved state comprises diluting the at least one heterogeneous cell composition by 1.5×, 2×, 3×, 4×, 5×, 6×, 7×, 8×, 9×, 10×, or at least 1.5×, 2×, 3×, 4×, 5×, 6×, 7×, 8×, 9×, or 10×. In some embodiments, the cell composition described herein e.g., a cell composition comprising a canine or feline cell, which is positive for both Vimentin and Cytokeratin-18, wherein the canine or feline cell is preferably a uterine-derived cell and/or a cell composition comprising any one or more of the heterogeneous cell populations described herein e.g., canine or feline cells, which are positive for Vimentin or Cytokeratin-18 and/or both markers, wherein the canine or feline cells are preferably uterine-derived cells, is prepared according to Protocol B, C, or D, or a similar protocol.

Also disclosed herein are any of the heterogeneous cell compositions disclosed herein for use in the treatment of canine or feline chronic kidney disease, atopic dermatitis, immune mediated arthritis, hepatitis, liver disease, inflammatory bowel disease, osteoarthritis, intravertebral disc disease, keratoconjunctivitis sicca (dry eye), pancreatitis, fibrosis, sclerosis, amyloidosis, immune mediated polyarthritis or wounds.

Also disclosed herein are any of the heterogeneous cell compositions disclosed herein for use in the manufacture of a medicament.

Chronic Kidney Disease

In some embodiments, the disease affecting the animal patient is chronic kidney disease (CKD). While more common in cats than dogs, CKD can potentially affect any animal, and therefore any disclosure regarding CKD provided herein may apply to cats, dogs, mice, rats, horses, cows, sheep, pigs, and other animals.

Feline CKD is a common inflammatory, degenerative condition that usually occurs in older cats. It has an overall prevalence of approximately 4%, which increases rapidly with age, reaching 30-40% among cats 10 years and older, and possibly as high as 80% after 15 years. It is the most common cause of death in cats 5 years and older, with a mortality rate of at least 13% at a median age of 15 years. As the kidneys are responsible for a wide range of physiologic processes, ranging from endocrine production to waste excretion, possible clinical manifestations are equally broad, but most often involve weight loss and inappetence. The underlying cause of CKD varies between individuals and is typically unknown. Multiple processes have been proposed, including hypoxia, toxic insults, vaccinations, chronic glomerulonephritis, chronic pyelonephritis, upper urinary tract obstructions, or viral infections such as retroviruses or morbillivirus. On occasion, a cause may be identified, such as polycystic kidney disease, amyloidosis, renal lymphoma, congenital disorders, hypercalcemic nephropathy, blunt abdominal trauma, acute kidney injury (e.g. specific toxin ingestion), or previous urethral obstruction. Beyond age, several other risk factors have been associated with CKD, including dehydration, dental disease, degenerative joint disease, or poor body condition.

CKD is characterized by chronic renal inflammation and degeneration. Histologically, renal specimens typically exhibit inflammatory infiltrate, increased extracellular matrix, tubular loss, mineralization, and fibrosis, all of which may be described more succinctly as tubulointerstitial nephritis and renal fibrosis. Grossly, kidneys shrink in size over time.

Mechanisms of disease progression are multifactorial and poorly understood. Some experts speculate that glomerular filtration rate (GFR), which is the best measure of renal function, decreases as a "normal" part of the kidney aging process due to structural changes, fewer functioning nephrons, and tubular dysfunction. At a cellular level, these phenomena have been associated with telomere shortening, mitochondrial injury, oxidative stress, pro-inflammatory and pro-fibrotic mediators, and a general imbalance between cell proliferation and renewal versus cell death and apoptosis. Although some argue that these molecular processes are simply one aspect of natural aging, others note that they may also result from chronic injury. Regardless of exact etiology, kidneys in patients with CKD become more sensitive to damage over time, with decreased recovery after injury, which results in an imbalance toward chronic inflammation and degeneration.

At a cellular level, direct causes of injury may include hypoxia, proteinuria, angiotensin II, hyperglycemia, or oxidative stress. Injury stimulates alteration of gene expression and recruitment of inflammatory cells such as T cells and macrophages, causing increased levels of pro-fibrotic and pro-inflammatory mediators. In turn, myofibroblasts are produced by fibrocytes, endothelial cells, and tubular epithelial cells, or via pericyte differentiation. This latter route contributes to loss of the interstitial capillary network, which increases oxidative stress, hypoxia, fibrosis, and further injury. This results in a vicious cycle of disease progression.

A long list of molecular aberrations have been associated with feline CKD, including abnormal levels of growth factors, cytokines, and chemokines, including, but not limited to interleukin-6 (IL-6), monocyte chemoattractant (MCP-1), tumor necrosis factor-α (TNF-α), epithelial growth factor (EGF), fibroblast growth factor (FGF), insulin-like growth factor (IGF), transforming growth factor-β (TGF-β), vascular endothelial growth factor (VEGF), or reactive oxygen species.

According to the International Society of Feline Medicine, which is led by a panel of leading experts, the efficacy of therapies for CKD should be considered primarily based on their ability to improve clinical signs, which determine quality of life (QOL). Although therapies may also slow underlying disease processes, thereby prolonging life, this is generally considered a secondary measure of efficacy. Because of this paradigm, a basic understanding of CKD clinical signs will help with study interpretation.

As renal function declines, a number of physiologic derangements occur, including accumulation of toxins in blood, decreased production of red blood cells, electrolyte imbalances, dehydration, metabolic acidosis, gastrointestinal malabsorption, systemic inflammation, increased energy requirements, impaired immune function, hypertension, and protein loss. The impacts of these abnormalities can vary between animals and over time.

Clinical signs related to these changes include chronic weight loss, inappetence, nausea, vomiting, diarrhea, constipation, increased drinking and urination, lethargy, halitosis (bad breath), oral ulcers, and poor haircoat. When disease is severe enough to induce anemia, gums may be pale pink or even white.

Hypertension can have a range of sequelae, including retinal hemorrhage, which may cause permanent vision loss; cardiac abnormalities, such as left ventricular hypertrophy (thickening of the heart), arrhythmia, murmur, and epistaxis (nose bleeds); and neurological deficits, such as altered mentation, seizures, behavioral changes, and vestibular signs (loss of balance).

CKD increases the risk of urinary tract infections (UTI), most likely because of decreased urine concentration. UTIs affecting only the lower urinary tract may be asymptomatic or cause a variety of clinical signs, including hematuria (blood in urine), pollakiuria (frequent urination), dysuria (painful urination), periuria (urinating in inappropriate locations), and/or stranguria (straining to urinate). More seriously, UTIs can involve the kidneys themselves (pyelonephritis), additionally causing flank pain, fever, and extreme lethargy.

CKD is defined by at least 3 months of reduced kidney function. The gold standard for measuring kidney function is glomerular filtration rate (GFR), which is defined by the volume of plasma filtered by glomeruli each minute, making it a direct measure of renal mass. The most accurate way of measuring GFR involves sequential measurement of a renally excreted substance. Ideally, such a substance is non-toxic, minimally metabolized, minimally bound to plasma proteins, and excreted only by the kidneys. One example is iohexol, an iodine-based contrast agent. To determine GFR, iohexol is given as a single injection, followed by collection of at least two post-injection serum samples at least 1 hour apart, with more samples over a longer period of time providing more accurate results. By measuring the amount of iohexol in these sequential samples, one can determine the rate of iohexol clearance, which is directly related to GFR. The rate of iohexol clearance, and therefore GFR, can then be compared with a normal range, providing a sense of normal versus abnormal renal function. GFR may also be measured with injection of contrast and nuclear scintigraphy, but this technique is generally exclusive to research.

Although infusion with sequential measurement is the clinical gold standard for determining GFR, it is uncommon in clinical practice. Instead, most clinicians rely upon a combination of serum creatinine and urine concentration, as recommended by the International Society of Feline Medicine (ISFM) and the International Renal Interest Society (IRIS). Creatinine is used for similar reasons as iohexol, with the notable exception that it is naturally produced by the body (a byproduct of muscle metabolism) and excreted via glomerular filtration with minimal tubular secretion or reabsorption. Theoretically, reduced GFR will lead to increased serum creatinine beyond the normal range. Urine specific gravity (a measure of urine concentration) is used because it gives a rough indication of the kidney's waste concentrating ability, which will be diminished with lost function, leading to more dilute urine.

To complicate matters, both serum creatinine and urine specific gravity can fall outside of normal limits for a variety of other, non-kidney-related reasons. For example, creatinine may be increased by above-average muscle mass, while urine specific gravity can be low (i.e. urine is diluted) simply because an animal recently drank a large quantity of water (among other reasons). Therefore, both serum creatinine and urine specific gravity must be interpreted in light of other available data, which may include clinical signs, radiographic findings, renal biopsy, and other laboratory results, such as blood urea nitrogen (BUN) concentration and urine protein level, both of which may be elevated with CKD. CKD may also be sub-staged by level of proteinuria and systolic blood pressure.

IRIS guidelines divide CKD into 4 stages, based on serum creatinine and clinical signs, as shown in Table 1. (Azotemia refers to abnormally high levels of waste products in blood, such as creatinine and BUN)

TABLE 1

IRIS staging of CKD

| Stage | Serum creatinine (mg/dL) | Comments |
|---|---|---|
| 1 | Less than 1.6 | Non-azotemic. Other renal abnormality present, such as inadequately concentrated urine without identifiable nonrenal cause. Clinical signs absent. |
| 2 | 1.6-2.8 | Mild azotemia. Clinical signs mild or absent |
| 3 | 2.9-5.0 | Moderate azotemia. Apparent systemic signs. |
| 4 | Greater than 5.0 | Severe azotemia. Many systemic signs with risk of uremic crisis. |

It is worth re-emphasizing that serum creatinine is a practical but imperfect measure of GFR, not only because it can be affected by nonrenal processes, but also because elevations in serum creatinine do not occur until at least 75% of nephrons are lost, making creatinine an insensitive biomarker of renal pathology. In other words, although IRIS stage 2 CKD is defined by "mild azotemia," the pathological reality of stage 2 disease is anything but mild, since three-quarters of kidney function have already been lost.

Because of the insensitivity of creatinine, and the impracticality of sequential GFR measurement with substances like iohexol, alternative surrogate measures of GFR are under investigation. The leading alternative (or supplement) to creatinine is symmetric dimethylarginine (SDMA), which may offer greater sensitivity than creatinine, although it is may also be affected by nonrenal processes. It is now commercially available and being used by some practitioners, particularly as a means of improving early disease detection.

Apart from diet, which has been shown to simultaneously improve quality of life (QOL) and longevity, most therapies aim to control clinical signs that impede QOL, such as anti-nausea medication for gastrointestinal issues, or fluid administration for dehydration.

A broad range of therapies are used to treat CKD, depending on stage of disease and individual clinical manifestation.

The mainstay of treatment is dietary modification, typically with prescription diets that have reduced phosphorous, protein, and sodium with increased caloric density, potassium, B vitamins, omega-3 fatty acids, and antioxidants. Of note, diet is the only existing therapy that has been proven to improve both quality of life and longevity.

Due to inappetence, nausea, and vomiting, many cats are also treated with anti-nausea and anti-emetic medications, as well as appetite stimulants. Two commonly used drugs are maropitant (anti-emetic) and mirtazapine (anti-nausea, anti-emetic, and appetite stimulant).

Dehydration is commonly managed with subcutaneous, saline-based fluids, often given at home by owners, with frequency and volume dependent on animal size and severity of disease. Intravenous fluids are more frequently used in acute crises.

Remaining therapies depend on particular disease manifestations. For example, anemic cats may be treated with darbepoetin, a synthetic form of the hormone erythropoietin, which stimulates red blood cell production in the bone marrow. Cats with hypertension are given anti-hypertensives, such as amlodipine, and those that develop UTIs receive antibiotics, ideally based on urine culture. Although renal transplantation and hemodialysis are available for cats at specialty centers, they are uncommonly performed due to financial and ethical concerns.

As a chronic inflammatory condition, feline CKD represents a potential therapeutic target for mesenchymal stem cells (MSCs), which have shown promise in veterinary medicine for other degenerative diseases, such as osteoarthritis and keratoconjunctivitis sicca in dogs. However, efficacy results of MSCs in cats with naturally-occurring CKD have been limited, and some preparations have resulted in acute infusion reactions.

In some embodiments, CKD may be treated using any one or more of the uterine-derived regenerative compositions or cell compositions disclosed herein. In some embodiments, the uterine-derived regenerative compositions or cell compositions e.g., a cell composition comprising a canine or feline cell, which is positive for both Vimentin and Cytokeratin-18, wherein the canine or feline cell is preferably a uterine-derived cell and/or a cell composition comprising any one or more of the heterogeneous cell populations described herein e.g., canine or feline cells, which are positive for Vimentin or Cytokeratin-18 and/or both markers, wherein the canine or feline cells are preferably uterine-derived cells, may be prepared according to Protocol B, C, or D, or a similar protocol.

EXAMPLES

Some aspects of the embodiments discussed above are disclosed in further detail in the following examples, which are not in any way intended to limit the scope of the present disclosure. Those in the art will appreciate that many other embodiments also fall within the scope of the invention, as it is described herein above and in the claims.

Example 1. Uterine Tissue Processing Protocol A
("Protocol A")

A uterine sample was obtained from a mammal, such as a cat or dog, from a donor program. Adipose tissue was removed from the uterine tissue sample.
1. Open the uterine body and horn tissue along the long axis, cut strips along the long axis, and mince the strips into tissue bits approximately 2 mm×2 mm.
2. Transfer the minced tissue to a centrifugable container, add DE 10 collagenase dissociation reagent, and place the container in a dry incubator on a rocker platform at 37° C. for 40 minutes to digest the tissue.
3. At the end of the incubation step, stop the digestion by adding tissue culture medium containing 10% FBS.
4. Fill the container with phosphate buffered saline (PBS) and centrifuge the container.
5. Remove the supernatant, leaving the pellet of cells.
6. Add a small volume of PBS and resuspend the pellet.
7. Transfer the suspension through a series of cell strainers: 100 µm, 70 µm, and 40 µm strainers.
8. Collect the cell suspension following the final cell strainer step and add PBS to bring the volume to 35-40 mL, and centrifuge.
9. Remove the supernatant, leaving the pellet of cells.
10. Add a small volume of PBS and resuspend the pellet.
11. Centrifuge again, remove the supernatant, and resuspend the pellet in 3-4 mL of PBS.
12. Perform a cell count on the suspension of cells.
13. Add a sufficient volume of tissue culture medium and transfer the cell suspension to an appropriate number of tissue culture flasks, depending on the total cell number and seeding density.
14. Place the flasks in an incubator under standard conditions to expand the culture through passages or days 1, 2, 3, and 4.

A sample of the cell preparation before the culturing step of 14 was taken and cryopreserved (A-PCF) to assess the composition at the end of processing protocol A. Adherent cells were cultured per standard protocol and samples of each culture interval were taken and cryopreserved on days 1, 2, 3, and 4 (A-D1, A-D2, A-D3, and A-D4, respectively). The cultures can be continued, and sample collection can be additionally repeated further to obtain cell compositions and samples from days 5, 6, 7, 8, 9, 10, 11, 12, 13, 14, 15, and onward.

Example 2. Uterine Tissue Processing Protocol B
("Protocol B")

A uterine tissue sample was obtained from a mammal, such as a cat or dog, from a donor program. Adipose tissue was removed from the uterine tissue sample.
1. Open the uterine body and horn tissue along the long axis, cut strips along the long axis, and mince the strips into tissue pieces approximately 3 mm×3 mm.
2. Transfer the minced tissue to a container, add defined enriched (DE10) collagenase (Vitacyte, #011-1110, a combination of collagenase and a neutral protease) dissociation reagent and incubate at 37° C. for 60 minutes to digest the tissue. Every 10 minutes, remove the container from the incubator and shake the container 40 times to distribute the solution, and return the container to the incubation.
3. At the end of the incubation step, stop the digestion by adding GIBCO DMEM tissue culture medium containing 10% fetal bovine serum (FBS).
4. Add additional tissue culture medium to dilute the cell suspension.
5. Transfer the contents of the container used for digestion to an appropriate number of T-225 culture flasks, which is based on the grams of tissue processed (e.g. 0.1 g tissue per T-225 culture flask).
6. Add a sufficient volume of tissue culture medium to each flask, add human FGF-2 to a final concentration of 8 ng/mL (e.g. 360 ng FGF-2 total in 45 mL of culture fluid in a T-225 flask), and place flasks in a 37° C., 5% $CO_2$ incubator.
7. Incubate under standard conditions to expand cells through passages or days 1, 2, 3 and 4.

A sample of the cell preparation before the culturing step of 7 was taken and cryopreserved (B-PCF) to assess the composition at the end of processing protocol B.

Samples prepared from tissues processed using this protocol contain undissociated tissue bits, so the cells were cultured in the following manner:
1. One day of incubation following the processing in Step 1 above (Day 1, D1), non-adherent cells and tissue pieces were recovered by removing the culture fluid and leaving the adherent cells.
2. The adherent cells were dislodged from the plastic by standard protocols known in the art and cryopreserved (sample called B-D1).
3. The recovered supernatant and tissue pieces were placed in a fresh flask and incubated overnight.
4. Steps 1-3 were repeated to generate samples on days 2, 3, and 4 (B-D2, B-D3, and B-D4, respectively).

A separate flask was established on Day 0 (step 7) and harvested on Day 4, without performing the recovery steps on earlier days (B-D4-1). Steps 1-3 can additionally be repeated further to obtain cell compositions and samples from days 5, 6, 7, 8, 9, 10, 11, 12, 13, 14, 15, and onward.

Example 3. Assessment of Protocol a and Protocol B Using Canine Uterine Tissues

Canine uterine tissue from a donor was obtained and weighed. Half of the donor tissue was processed according to Protocol A, and the other half was processed according to Protocol B. Only the Day 0 PCF (A-PCF and B-PCF) samples and the Day 4 (A-D4 and B-D4-1) samples were analyzed in this Example.

Flow Cytometry Protocol (Example 3)

All cell preparations were recovered from cryopreserved vials and stained with CD44, and CD90 reagents using standard protocols. A live/dead stain was added to all preparations.

Starting with the input population of cells, a cell population excluding swollen cells and debris was established based on side scatter. From this, a "Live/Dead vs Forward Scatter" plot was generated, and a live cell population was established. The live cell population was examined for CD44 and CD90 staining.

Results (Example 3)

Gating of the samples is shown in FIG. 1. The gates were set to exclude debris and damaged cells based on side scatter. There was evidence of two cell populations in the B-D4-1 panel compared to three cell populations in the A-D4 panel, with the third cell population present close to the origin.

Figure 2:
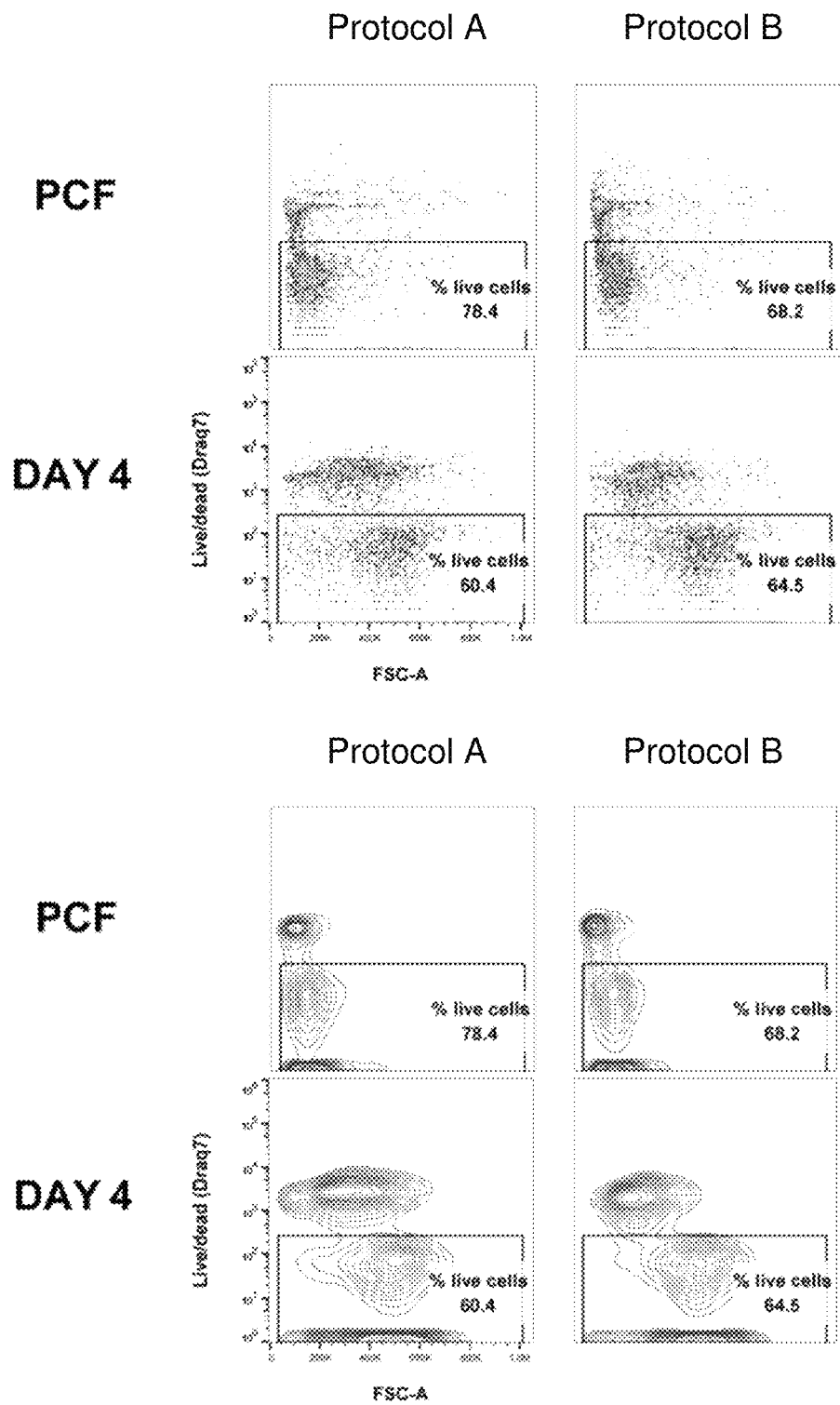
FIG. 2 depicts dot and contour flow cytometric plots of FSC-A and Live/Dead assay for intact cells of PCF and Day 4 samples of canine uterine-derived cells processed according to Protocols A and B for Example 3.

The distribution of live/dead cells is shown in FIG. 2. Viability of cultured cells decreased from the PCF viabilities, which might reflect the die-off of cells that do not adhere to the tissue culture flask plastic or might not be supported by the culture medium used. As is more easily visualized in the contour map of FIG. 2, there were two distinct populations of live cells present (i.e. there are two distinct contour regions present within the Live gate box) for both methods. There was also a shift in the cell size and/or shape of cells obtained from D4 cultures compared to the size/shape distribution evident for the PCF samples. This is seen by the rightward shift along the x-axis of the plots for D4 versus the distribution of cells in the plots for PCT, which were more tightly clustered closer to the origin.

Figure 3:
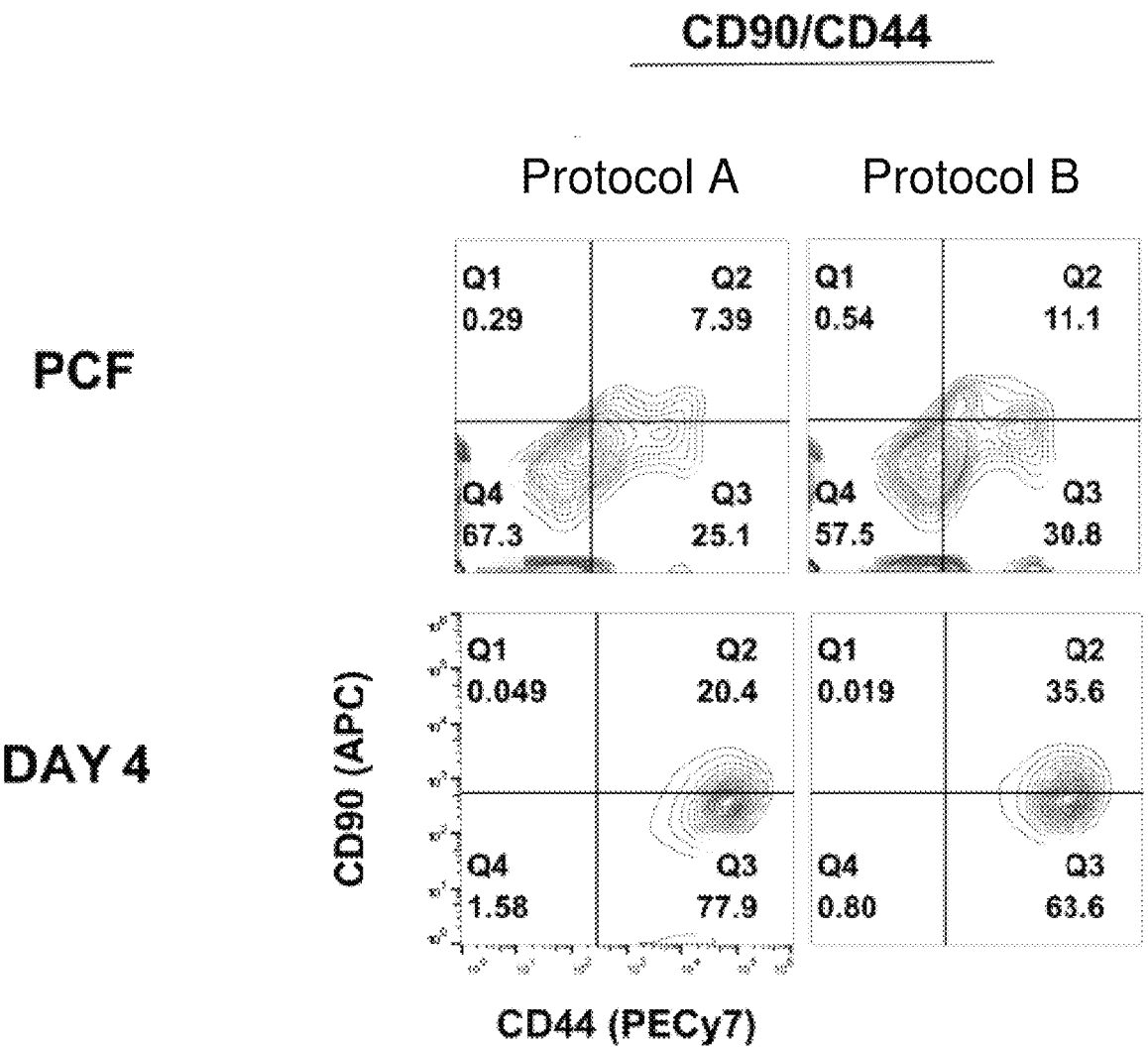
FIG. 3 depicts contour flow cytometric plots of CD44 and CD90 staining for live cells of PCF and Day 4 samples of canine uterine-derived cells processed according to Protocols A and B for Example 3.

The contour plots of CD90/CD44 staining for the PCF and D4 samples are shown in FIG. 3. The percentage of cells in the upper right and lower right quadrants change noticeably from the levels in PCF to the levels in D4 for both protocols.

As shown in Table 2, the number of viable cells in the PCF samples obtained with the protocols outlined above were $5.1 \times 10^6$ for Protocol A and $4.3 \times 10^6$ for Protocol B. Following four days in culture (D4 samples), the number of cells were $0.45 \times 10^6$ for Protocol A and $5.3 \times 10^6$ for Protocol B. The percentages shown in Table 2 reflect the values after subtracting out the unstained signal (due to autofluorescence) for CD44+/CD90+ and CD44+/CD90− staining populations for A-PCF, B-PCF, A-D4, and B-D4-1). However, the autofluorescence signals for the A-D4 sample were estimated due to the lack of cells for this control.

TABLE 2

Summary of cell numbers and CD marker percentages for live cells (Example 3)

| | Cell number ($\times 10^6$) | CD44+/CD90+ % | CD44+/CD90− % |
|---|---|---|---|
| PCF | | | |
| A-PCF | 5.1 | 4.4 | 24.6 |
| B-PCF | 4.3 | 4.9 | 30.3 |
| Day 4 | | | |
| A-D4 | 0.45 | 17.4 | 73.4 |
| B-D4-1 | 5.3 | 28.5 | 60.3 |

Table 3 shows the fold changes in the percentage of cells positive for the indicated CD markers within each protocol at D4 and at PCF. For example, there was a 3.9-fold higher percentage of cells that were CD44+/CD90+ in the A-D4 sample versus the A-PCF sample. Fold-changes greater than 1 indicate an enrichment of the cells positive for the CD markers as a result of culturing.

Table 4 shows a frequency of the percentages of cells reactive with the indicated CD marker sets within each process for PCF and D4 samples. For example, the percentage of cells in the A-PCF sample that were CD44+ is 5.5-fold higher compared to the percentage of cells in the A-PCF sample that were CD44+/CD90+.

TABLE 3

Fold-changes in D4% over PCF % (Example 3)

| | CD44+/CD90+ | CD44+/CD90− |
|---|---|---|
| Protocol A | 3.9 | 3.0 |
| Protocol B | 5.8 | 2.0 |

TABLE 4

Fold-changes of positive CD marker % (Example 3)

| | Fold Change in PCF CD44+ to CD44+/CD90+ | Fold Change in D4 CD44+ to CD44+/CD90+ |
|---|---|---|
| Protocol A | 5.5 | 4.2 |
| Protocol B | 6.2 | 2.1 |

Conclusions (Example 3)

The distribution of cells shown in FIG. 1 appears to be similar for the PCF samples obtained by both protocols (Protocol A and Protocol B). However, the contour plot for B-D4-1 is dominated by two cell populations, while the contour plot for A-D4 shows those two cell populations, along with an additional area of a distinct cell population close to the origin.

Cells found in the PCF samples produced by both Protocol A and Protocol B show a tight clustering in their scatter plots as seen in FIG. 2. However, cells cultured to D4 from both protocols have adopted changes in shape and size, as demonstrated by the shifting of cells along the x-axis (Forward Scatter-A). These changes are most likely due to influences on the cells as they are being cultured, which indicates that there is a shift away from the morphology of the cells present in the PCF samples obtained by digestion of the uterine tissue.

Cells obtained by both protocols were reactive with CD90 and CD44 markers in patterns that were nominally similar for both PCF and D4 as shown in FIG. 3.

As shown in Table 2, Protocol B resulted in a PCF sample that had higher percentages for the indicated CD markers.

As shown in Table 2, culturing of the PCF samples to D4 showed that Protocol B did not consistently yield higher percentages of the indicated CD markers. In fact, Protocol A resulted in a higher percentage of cells positive for CD44+/CD90− markers.

Generally, there were a higher percentage of cells positive for the indicated CD markers in D4 samples compared to the PCF samples. This outcome is shown in Table 3 as a fold-increase in the percentage positive cells at D4 over PCF for both Protocol A and B for the indicated CD markers.

There was a single CD marker set used in this Example: CD44/CD90, with percentages of cells expressing both markers together (doubly positive—upper right quadrant in FIG. 3) or just one of the markers (singly positive—lower right quadrant in FIG. 3) as shown in Table 2. Changes in the percentages of cells doubly positive versus singly positive for each sample type is shown in Table 4. For example, there is a 5.5-fold higher percentage of singly positive cells in the A-PCF (CD44+/CD90−) compared to the doubly positive (CD44+/CD90+) cell percentage.

The percentage of cells singly positive for CD44 (CD44+/CD90−) was higher compared to the percentage of doubly positive cells (CD44+/CD90+) in A-PCF and B-PCF compared to the sample percentages in A-D4 and B-D4-1 (A-PCF 5.5-fold vs. A-D4 4.2-fold; B-PCF 6.2-fold vs. B-D4-1 2.1-fold). Furthermore, there was a difference of 1.3-fold between the level of cells singly positive for CD44 for A-PCF (5.5-fold) compared to A-D4 (4.2-fold), while there was a difference of 4.1-fold between cells singly positive for CD44 for B-PCF (6.2-fold) and B-D4-1 (2.1-fold).

Example 4. Additional Assessment of Protocol A and Protocol B Using Canine Uterine Tissues Canine uterine tissue from a donor (different from the donor of Example 3) was obtained and weighed. Half of the donor tissue was processed according to Protocol A, and the other half was processed according to Protocol B. The cells from days 0, 1, 2, 3 and 4 of both protocols (A-PCF, A-D1, A-D2, A-D3, A-D4 and B-PCF, B-D1, B-D2, B-D3, B-D4) were analyzed in this Example.

Flow Cytometry Protocol (Example 4)

All cell preparations were recovered from cryopreserved vials and stained with CD44 and CD90 reagents using standard protocols. A live/dead stain was added to all preparations.

Starting with the input population of cells, a cell population excluding swollen cells and debris was established based on side scatter. From this, a "Live/Dead vs Forward Scatter" plot was generated, and a live cell population was established. The live cell population was examined for CD44 and CD90 staining.

In addition, staining of cell preparations was performed to detect cytokeratin and vimentin, which required a separate aliquot of cells. The protocol involved fixing the cells with the True-Nuclear Transcription Factor Buffer kit (BioLegend, #424401), followed by treating the cells with a permeabilizer buffer, after which the permeabilized cells were incubated with the appropriate antibodies specific to cytokeratin or vimentin. CD90/CD44 also was assessed with the fixed cells.

Results (Example 4)

Due to poor yields of cells, some preparations were unavailable for evaluation, which are indicated as "NA" in the tables or directly noted in the figures. The focus of this summary will be on results from PCF and D1-4 samples from Protocol B and A-PCF or A-D4 (fixed/permeabilized preparation only) from Protocol A, as available.

Figure 4:
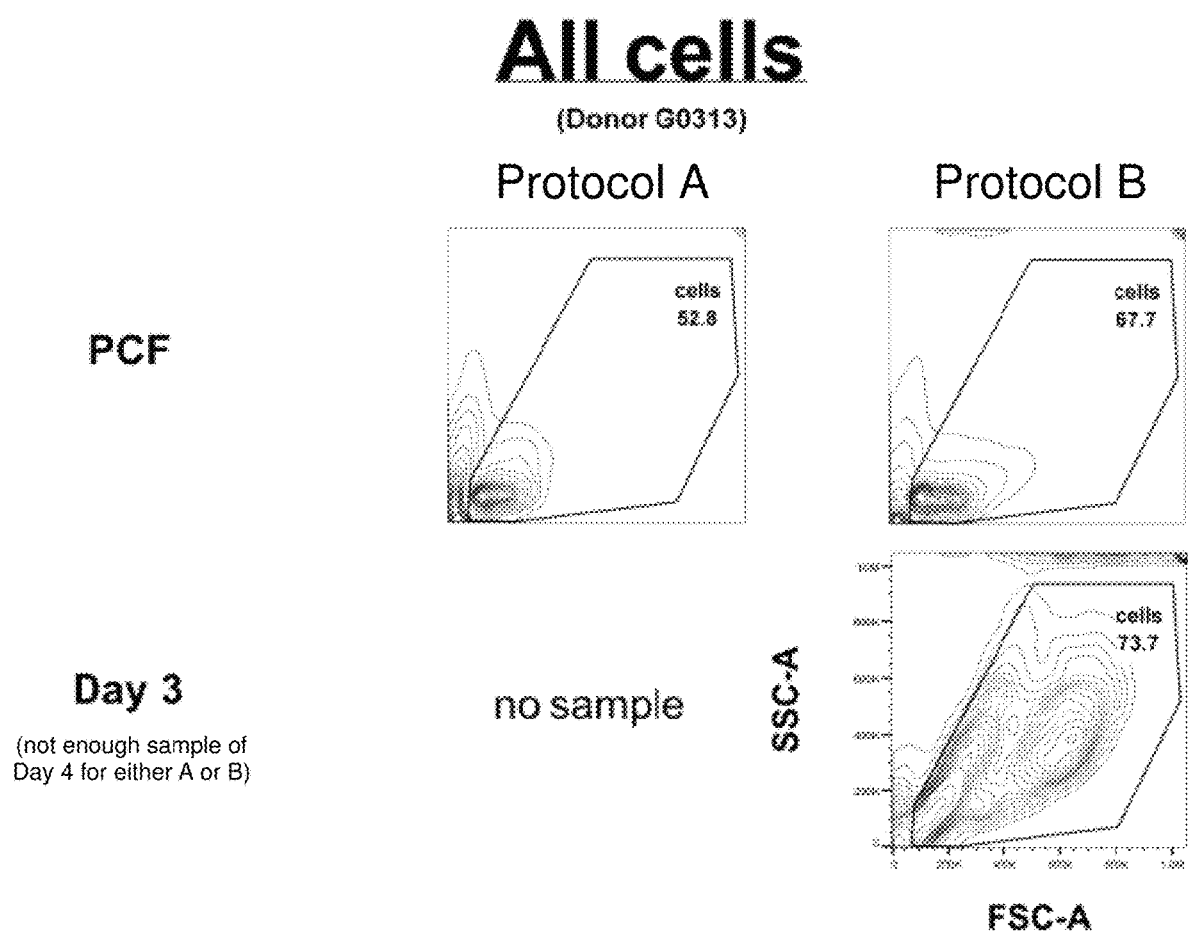
FIG. 4 depicts contour flow cytometric plots of FSC-A and SSC-A for total cell populations of PCF and Day 3 samples of canine uterine-derived cells processed according to Protocols A and B for Example 4.

Gating of the samples is shown in FIG. 4. The gates were set to exclude debris and damaged cells based on side scatter, as shown for A-PCF and B-PCF plots. There was inadequate sample to assess A-D3, A-D4 or B-D4. There is evidence of two primary cell populations in the B-D3 plot, while there is a very small population at higher side scatter levels. Donor to donor variability may account for the presence of two populations, with a "third" very small population, in the B-PCF sample from the processing of the donor sample in this Example, while the donor sample from Example 3 showed only two prominent populations for B-D4-1.

Figure 5:
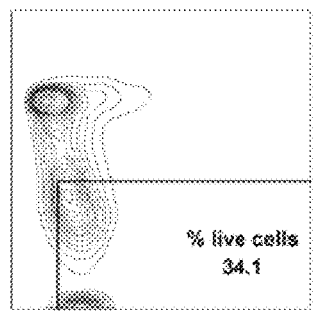
FIG. 5 depicts contour flow cytometric plots of FSC-A and Live/Dead assay for intact cells of PCF and Day 3 samples of canine uterine-derived cells processed according to Protocols A and B for Example 4.
Figure 5:
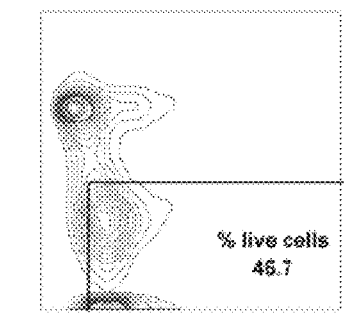
Figure 5:
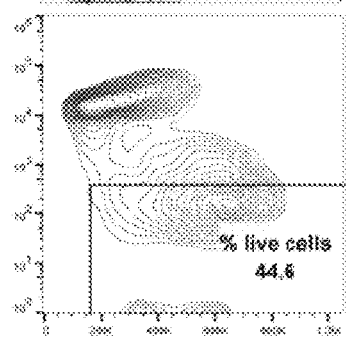

The distribution of live/dead cells is shown in FIG. 5. There are two distinct populations of live cells present (i.e. there are two distinct contour regions present within the Live gate box) for both protocols. There is also a shift in the cell size and/or shape of cells obtained from the B-D3 sample compared to the size/shape distribution evident for the B-PCF sample. This is seen by the rightward shift along the Forward Scatter axis (x-axis) of the plots for B-D3 versus the distribution of cells in B-PCF, which are more tightly clustered closer to the left axis. The patterns observed for the A-PCF and B-PCF/B-D3 are similar to the previous Live/Dead results shown in Example 3.

Figure 6:
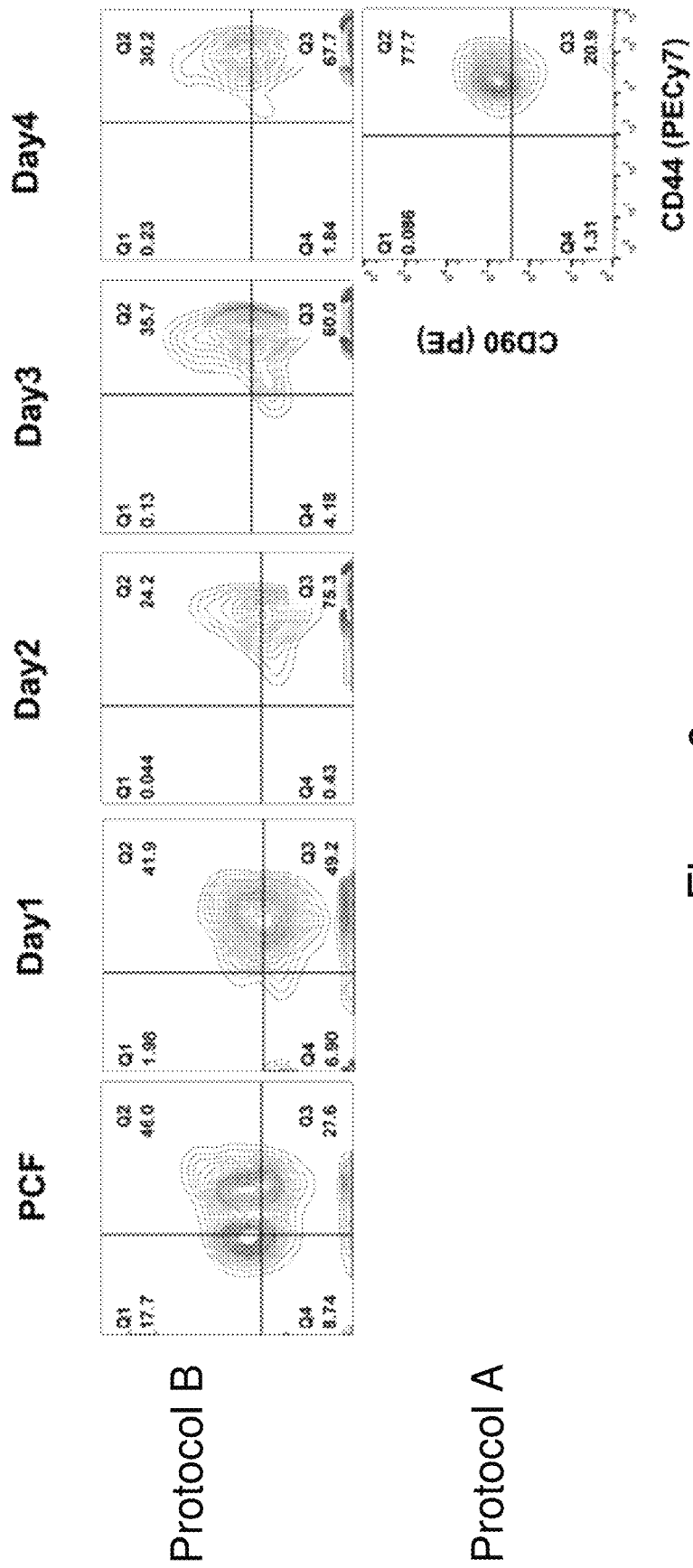
FIG. 6 depicts contour flow cytometric plots of CD44 and CD90 staining for live cells of PCF, Day 1, Day 2, Day 3, and Day 4 samples of canine uterine-derived cells processed according to Protocols A and B for Example 4.

The contour plots of CD90/CD44 staining for the A-D4, B-PCF, B-D1, B-D2, B-D3, and B-D4 samples are shown in FIG. 6. The percentage of cells in the upper right and lower right quadrants change noticeably from the levels in B-PCF to the levels at B-D3 and B-D4. This pattern was observed previously in the Protocol B samples of Example 3.

Figure 7:
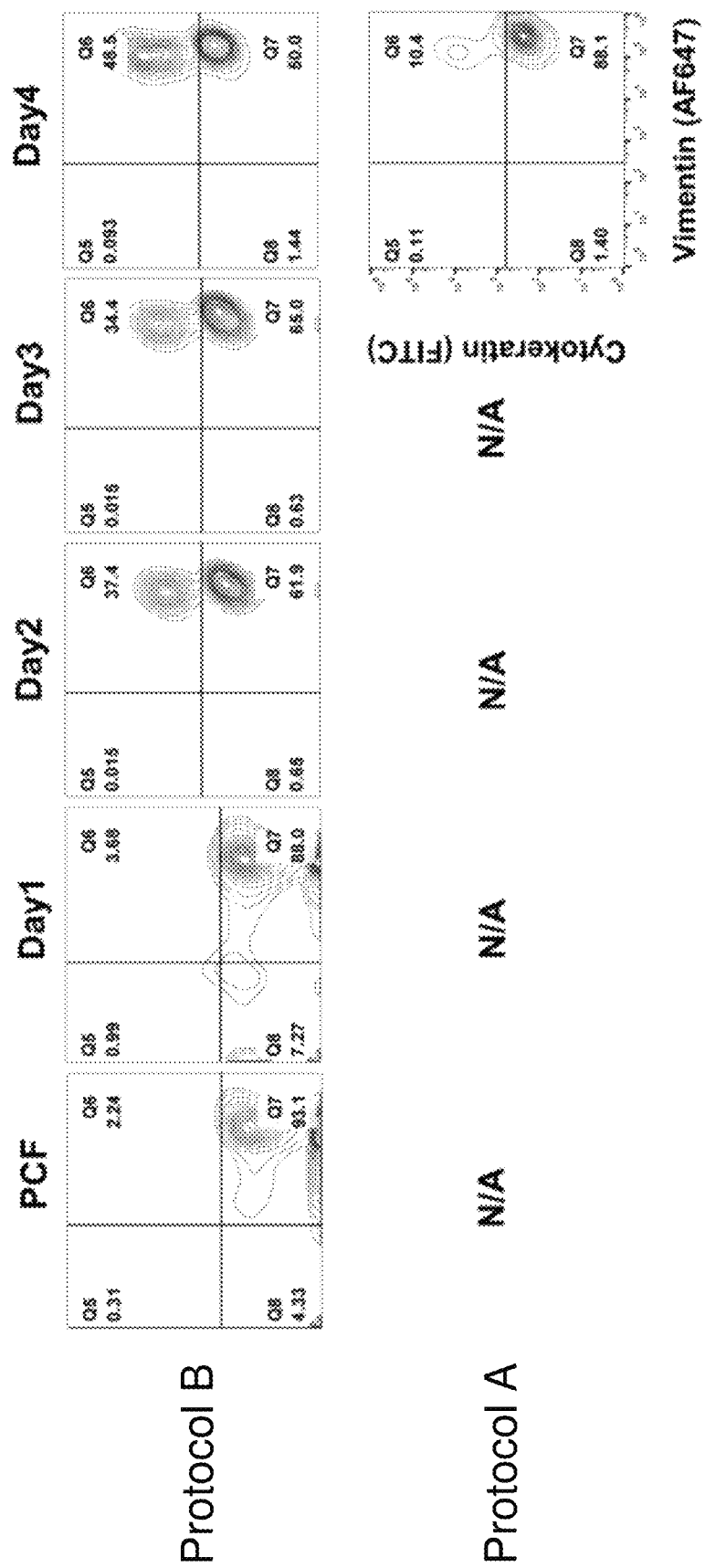
FIG. 7 depicts contour flow cytometric plots of vimentin and cytokeratin staining for live cells of PCF, Day 1, Day 2, Day 3, and Day 4 samples of canine uterine-derived cells processed according to Protocols A and B for Example 4.

As shown in FIG. 7, Cytokeratin/Vimentin (C/V) staining was obtained for A-D4, B-PCF, B-D1, B-D2, B-D3, and B-D4 samples. There were not enough cells available for A-PCF to be assessed for C/V staining.

As shown in Table 5, the number of viable cells obtained with the protocols outline above were quite low for both A-PCF and B-PCF. The low cell number was also present for B-D3. Percentages of the CD44/CD90 set is similar to the results observed in Example 3, but not identical.

TABLE 5

Summary of cell numbers and CD marker percentages for live cells (Example 4)

| | Cell number (×10$^6$) | CD44+/CD90+ % | CD44+/CD90− % |
|---|---|---|---|
| PCF | | | |
| A-PCF | 1.0 | 22.2 | 26.0 |
| B-PCF | 0.94 | 12.6 | 20.7 |
| Day 3 | | | |
| A-D3 | 0.17 | NA | NA |
| B-D3 | 0.4 | 27.9 | 70.0 |

Table 6 shows the fold changes in the percentage of cells positive for the indicated CD markers for B-PCF and B-D3, but only A-PCF (due to poor yields). Table 7 shows the fold changes in the singly positive CD markers versus the doubly positive marker levels.

TABLE 6

Fold-changes in D3% over PCF % (Example 4)

| | CD44+/CD90+ | CD44+/CD90− |
|---|---|---|
| Protocol A | NA | NA |
| Protocol B | 2.2 | 3.4 |

TABLE 7

Fold-changes of positive CD marker % (Example 4)

| | Fold Change in PCF CD44+ to CD44+/CD90+ | Fold Change in D4 CD44+ to CD44+/CD90+ |
|---|---|---|
| Protocol A | 1.2 | NA |
| Protocol B | 1.6 | 2.5 |

The flow cytometric results of the B-PCF, -D1, -D2, -D3, and -D4 and A-D4 for reactivity with cytokeratin and vimentin (C/V) is shown in Table 8 in terms of the percentage of the singly positive V+ cells (FIG. 7, lower right quadrant) and doubly positive C+/V+ cells (FIG. 7, upper right quadrant) present in the preparations. Ratios of the singly positive (V+) cell level to the doubly positive (C+/V+) cell level changed from nearly 42-fold for B-PCF to 1.03-fold at B-D4. While there are some C+/V+ cells present in the A-D4 preparation, the ratio of the percentage of V+ cells to the percentage of C+/V+ cells is 8.5-fold.

TABLE 8

Ratios of vimentin+ cells over cytokeratin+/vimentin+ cells (Example 4)

| | | Protocol A | A: Ratio V+ to C+/V+ | Protocol B | B: Ratio V+ to C+/V+ |
|---|---|---|---|---|---|
| PCF (%) | V+ | 93.1 | 41.6 | NA | NA |
| | C+/V+ | 2.24 | | NA | |
| D1 (%) | V+ | 88.0 | 23.9 | NA | NA |
| | C+/V+ | 3.68 | | NA | |

TABLE 8-continued

Ratios of vimentin+ cells over cytokeratin+/vimentin+ cells (Example 4)

|  |  | Protocol A | A: Ratio V+ to C+/V+ | Protocol B | B: Ratio V+ to C+/V+ |
|---|---|---|---|---|---|
| D2 (%) | V+ | 61.9 | 1.7 | NA | NA |
|  | C+/V+ | 37.4 |  | NA |  |
| D3 (%) | V+ | 65.0 | 1.9 | NA | NA |
|  | C+/V+ | 34.4 |  | NA |  |
| D4 (%) | V+ | 50.0 | 1.03 | 88.1 | 8.5 |
|  | C+/V+ | 48.5 |  | 10.4 |  |

Conclusions (Example 4)

The distribution of cells shown in FIG. 4 appears to be similar for the PCF samples obtained by both protocols. However, the contour plot for B-D3 is dominated by two cell populations, with a very small population at higher side scatter values for B-D3. No comparison of A-PCF to A-D3 is available.

Cells found in the PCF samples produced by both protocols show a tight clustering in their scatter plots as seen in FIG. 5. However, cells cultured through D3 from Protocol B have adopted changes in shape and size, as demonstrated by the shifting of cells along the x-axis (Forward Scatter-A). These changes are most likely due to influences on the cells as they are being cultured, which indicates that there is a shift away from the morphology of the cells present in the PCF obtained by digestion of the tissue.

Cells obtained by both protocols were reactive with CD90 and CD44 markers in patterns that were nominally similar for both PCF samples as shown in FIG. 6 (CD90/CD44).

In contrast to the results of Example 3, Protocol A resulted in a PCF sample that had higher percentages of the indicated CD markers compared to the values for the PCF sample from Protocol B, as shown in Table 5. This is most likely due to donor-to-donor variability.

Both fold-change results showed a higher percentage of cells positive for the indicated CD markers in B-D3 samples compared to the B-PCF samples, as shown in Table 6. This is similar to the results of Example 3.

There was one CD marker set used in this Example: CD44/CD90, with percentages of cells expressing both markers together (doubly positive—upper quadrant in FIG. 6) or just one of the markers (singly positive—lower right quadrant in FIG. 6) as shown in Table 5. Changes in the percentages of cells doubly positive versus singly positive for each sample type is shown in Table 7. The fold shift for PCF was higher than for D4 for Example 3 but was the opposite for this Example. Donor variability most likely accounts for the different patterns.

Reactivity for cytokeratin/vimentin (C/V) is shown in FIG. 7 for Protocol B processed material from B-PCF to B-D1, -D2, -D3, and -D4. Of the cells present in the B-PCF, there is a low level of C+/V+ doubly positive cells (2.24%; upper right quadrant), while a significant portion are only positive for vimentin (93.1%; lower right quadrant). Within the vimentin singly positive cell population (lower right quadrant), there are two populations present; one population could be considered as C-null/V+, but the other population displays a low signal for cytokeratin, although it also would be considered as negative. The C-null/V+ population diminishes over time, which might indicate that those cells are non-viable, or that they transform during culture. There are also virtually no cytokeratin-only positive cells (upper left quadrant) in B-PCF, which is maintained through to B-D4.

The pattern for cells from Protocol B shifts during culture, as shown in FIG. 7, with an increasing level of C+/V+ cells appearing, such that by D4, there are virtually the same percentage of cells that are C+/V+ as are cells that are V+ only. This progression is illustrated in the ratios shown in Table 8.

In contrast, the A-D4 sample shown in FIG. 7 has a ratio of approximately 8.5 in favor of V+ only over C+/V+ cell levels, so there is an obvious difference in the levels of cells that are singly positive for vimentin and doubly positive for cytokeratin/vimentin between Protocol B and Protocol A processed cells after four days in culture.

The B-D1, -D2, -D3, and -D4 cultures whose plots are shown in FIG. 7 were seeded at Day 0 (D0) with tissue and cells, so in essence they reflect independent snapshots of the cells present in culture on those days. The increasing levels of C+/V+ cells with time in culture might reflect the emergence of additional cytokeratin-positive epithelial progenitor cells from the tissue pieces that are present in the method of Protocol B. While there are C+/V+ cells present in the A-D4 culture, there is a substantial difference in the ratios relative to levels of V+ only cells, as shown in Table 8.

Example 5. Characterization of Feline Uterine-Derived Cell Compositions

Figure 8:
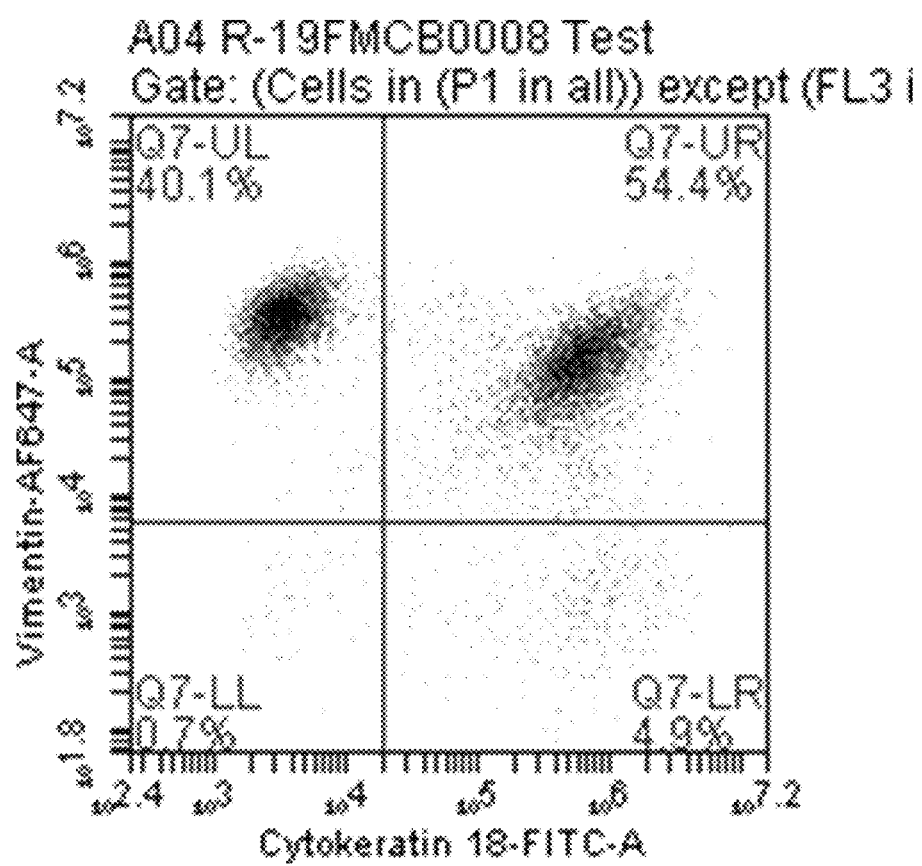
FIG. 8 depicts a dot flow cytometric plot of vimentin and cytokeratin staining for cells of Day 4 samples of feline uterine-derived cells processed according to Protocols A and B for Example 5.

Feline uterine tissue from a donor was processed according to Protocol B. The resultant cell population was grown for at least 4 passages. These cells were collected, fixed, and permeabilized for 15 minutes with a Triton-X 100 buffer according to standard procedures known in the art. Anti-cytokeratin-18 antibody conjugated to FITC and anti-vimentin antibody conjugated to Alexa Fluor 647 were used to stain the permeabilized cells. FIG. 8 depicts the flow cytometric plot of these stained cells and shows the presence of C+/V+ doubly-positive cells (upper right quadrant), as well as V+ only singly positive cells (upper left quadrant) and C+ only singly positive cells (lower right quadrant). The ratio of V+ to C+/V+ cells as shown in FIG. 8 is 0.74.

Figure 9A:
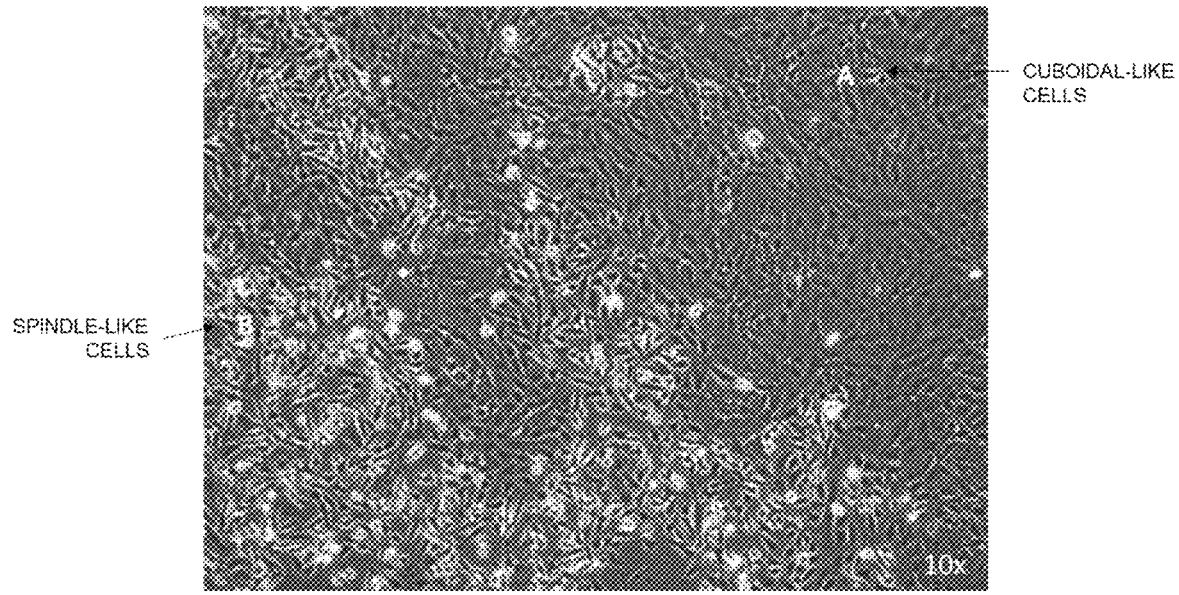
FIG. 9A-D depicts microscopy images of feline uterine-derived cells in phase contrast (A), anti-vimentin/DAPI (B), anti-cytokeratin-18/DAPI (C), and anti-cytokeratin-18/anti-vimentin (D).
Figure 9B:
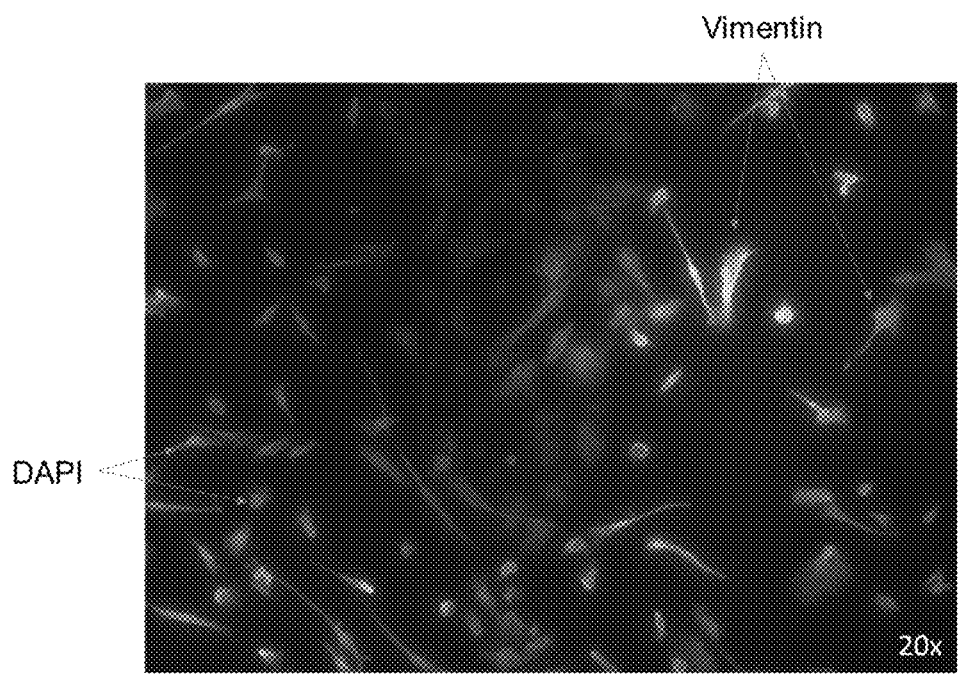
Figure 9C:
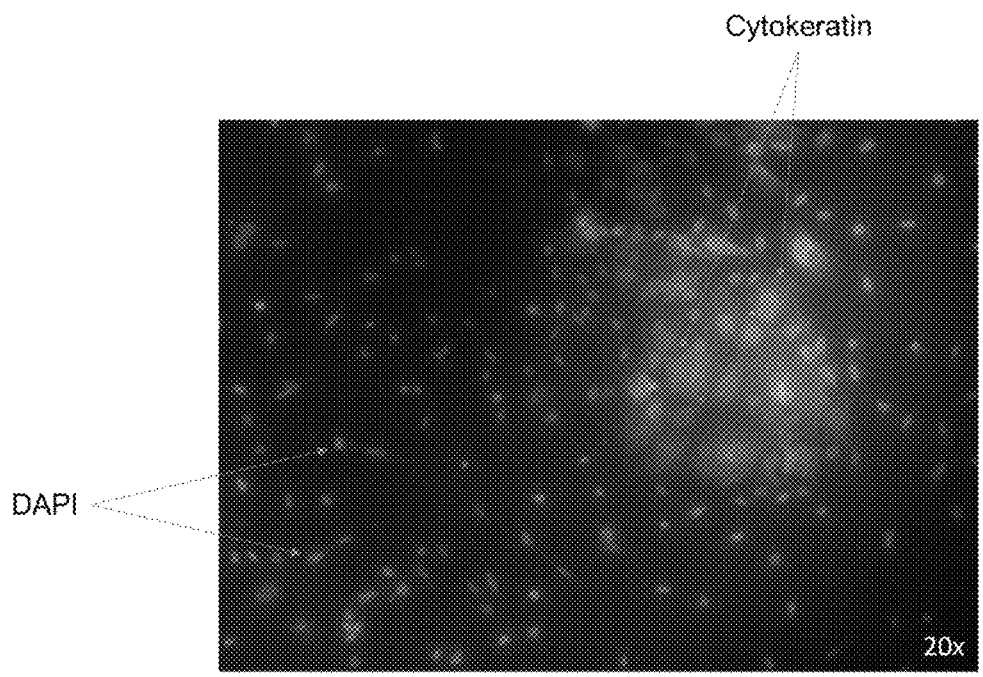
Figure 9D:
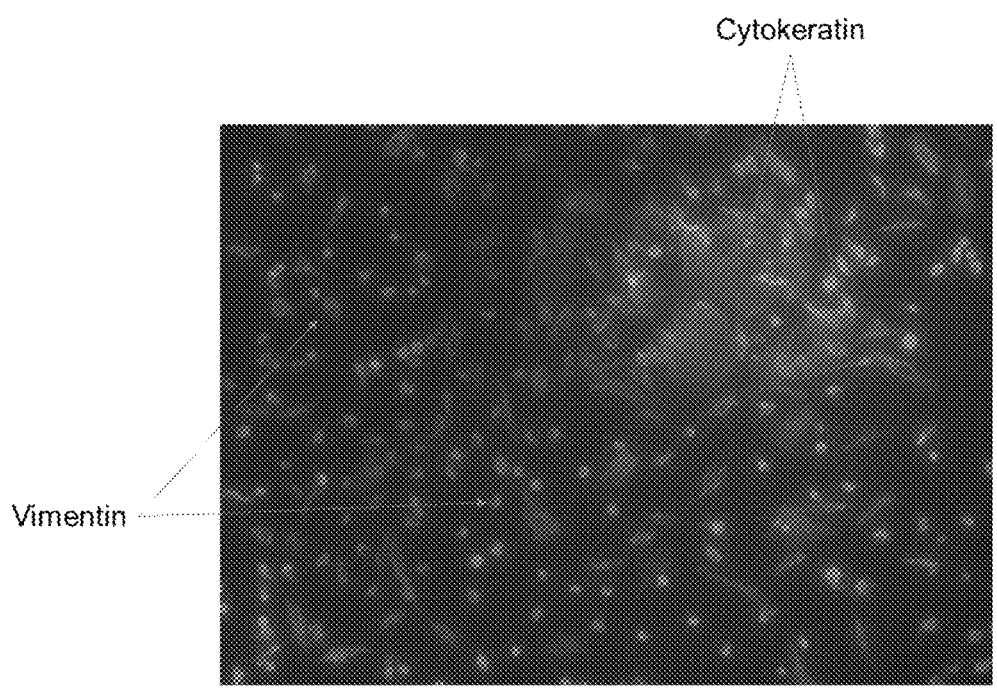

The population of feline uterine-derived cells at passage 4 include cells that are cuboidal-like (i.e. epithelial progenitor cells) and spindle-like (i.e mesenchymal progenitor cells) (FIG. 9A). Feline uterine-derived cells at passage 4 were grown on cell culture slides, fixed, permeabilized, and incubated with (1) anti-vimentin-FITC and DAPI (FIG. 9B), (2) anti-cytokeratin-18-FITC and DAPI (FIG. 9C), and (3) anti-cytokeratin-18-FITC and anti-vimentin-Alexa Fluor 594 (FIG. 9D). These images highlight the presence of a heterogeneous cell population when processed with Protocol B.

Example 6. Treatment of Feline CKD with Feline Uterine-Derived Regenerative Cells The use of allogeneic feline uterine-derived regenerative cells (URCs) as a treatment for chronic kidney disease (CKD) in cats was investigated. The efficacy of URC in improving kidney function in unilaterally nephrectomized cats with azotemia and compromised glomerular filtration rate associated with CKD was evaluated. The URCs used herein comprise a heterogeneous cell composition produced by following Protocol B, Protocol C, Protocol D, or a similar protocol, where the cell composition includes both vimentin-only singly positive and vimentin/cytokeratin doubly positive cell populations (e.g. a population of mesenchymal progenitor cells and a population of epithelial progenitor cells). In some embodiments, the ratio of vimentin-only singly positive cells to vimentin/cytokeratin doubly positive cells is approximately 50%:50% or about 50%:50%, but this ratio can diverge as much as ±20% (e.g. about 40%:60% or about 60%:40% or any ratio in between)

Study Design

Eighteen (15 female and 3 male) renal compromised nephrectomized cats that met the inclusion criteria were used in this study. All cats were dosed with a single intravenous (IV) infusion (30 million (M) cells) of allogeneic feline uterine-derived regenerative cells ("investigational veterinary product", "IVP") at a rate of 1 million cells per minute (1 mL/min) with the initial 5 min of infusion at a rate of 0.5 mL/min. The IVP was administered on two occasions to all cats (Day 0/1 and Day 14/15). As stated above, the IVP comprises a heterogeneous cell composition prepared according to Protocol B, Protocol C, Protocol D, or a similar protocol, and is essentially made up of a vimentin-only singly positive cell population and a vimentin/cytokeratin doubly positive cell population.

The primary variables measured were plasma creatinine and glomerular filtration rate (GFR; by means of iohexol clearance test). The IVP was to be considered effective in an individual cat if a 20% reduction in plasma creatinine level or a 20% increase in GFR in at least 50% of the cats was achieved during the course of the study. Furthermore, for a successful outcome of the IVP, at least 50% of all cats had to demonstrate efficacy in either creatinine reduction or GFR increase. Blood samples were collected for measurement of clinical pathology parameters on Days −7, 7, 13 29, 56, 97, 120, 149 and 181. Blood samples, collected for measurement of GFR, were obtained prior to administration, and at 2, 3, and 4 hours post iohexol administration on Days −5, 13 and 28; and at 2, 3, and 4 hours post iohexol administration on Days 57, 99, 121, 150 and 182.

Secondary variables included analysis of urine specific gravity and urine total protein (analysed on samples collected on Days −7, 7, 14, 28, 56, 97, 120, 149 and 181); and water and feed intake (measured at weekly intervals).

For each cat, the IVP was to be considered safe if no serious adverse events that might be attributed to the IVP were observed. In addition, the product must be well-tolerated in the cats, with low incidence rates for adverse events in terms of number of animals affected and categories of events occurring.

Results (Example 6)

Primary Variables

There was a significant mean decrease in plasma creatinine on Day 28 only (P=0.0283) compared to baseline. A 20% decrease of this parameter was observed in four animals on this day. There was a significant mean increase in GFR on Days 13, 28, 57, 99, 121 and 182 compared to baseline (P<0.0001 for Days 13 to 99 inclusive; P=0.0029 and P=0.0225 for Days 121 and 182 respectively). Greater than 50% of the cats demonstrated a 20% increase in GFR on Days 13, 28, 57 and 99.

Secondary Variables

Statistical analysis results show that there was a significant increase in diet consumption on Days 14, 42, 70, 84, 112, 126, 140 and 154 compared to baseline (P<0.05). There was also a significant increase in water consumption from Day 42 to Day 168 inclusive compared to baseline (P<0.05). Urinary analysis results show that compared to baseline urine specific gravity was significantly decreased on Day 13 only (P<0.0001); urine protein was significantly increased on Day 181 only (P=0.0221); urine creatinine was significantly decreased on Days 7, 13, 28, 56, 97, 120 and 181 (P<0.05); and urine protein/creatinine ratio was significantly increased on Days 120, 149 and 181 (P<0.05).

Test Article Preparation

Test article (quantity sufficient for dosing on any given day) was removed from the dry shipper on the day of dosing. CellSeal® vials of test article were held in a water bath maintained at 37° C. (±1° C.) until thawed, three to five minutes. A 3 or 5 mL syringe and 18 gauge needle were used to remove the cell suspension ($10 \times 10^6$ cells/mL) from the vial. A sufficient volume of cells was placed in a syringe containing a sufficient volume of 3.3% trehalose in 0.9% saline to yield 1×10 6 URC per mL. Immediately prior to dosing for each cat, the intended volume of prepared test article suspension in the 60 mL syringe was inverted a number of times to mix and then loaded into the syringe pump.

Test Article Administration

Cats were dosed with a single IV infusion of IVP. IVP dosing occurred on Days 0/1 and 14/15.

Test article was administered via IV infusion using a syringe pump. All cats received the test article (approximately 30 M cells) at a rate of approximately 1 million cells per minute (approximately 1 mL/min). For the initial 5 min of infusion, cells were administered at ½ the rate (i.e. approximately 0.5 mL/min). Since there were no adverse events, cells were then infused at the normal rate (1 mL/min).

Clinical Chemistry

Blood was collected from each cat on the following schedule: once during acclimation Day −7; and Days 7, 13 29, 56, 97, 120, 149 and 181.

On any given day, blood collection was performed in the fasted state. Blood was obtained from the jugular vein via direct venipuncture using a suitably sized needle and syringe. Approximately 2 mL of blood was drawn and immediately transferred to appropriately labeled blood collection tubes.

The blood collection tubes used included:
1× ethylenediaminetetraacetic acid (EDTA—0.7 mL);
1× lithium heparin (1.3 mL);
EDTA and lithium heparin tubes were gently inverted to ensure proper mixing of blood with anticoagulant.
Lithium heparin tubes were centrifuged at 3000 rpm for 10 minutes and plasma was removed for analysis.

Glomerular Filtration Rate Measurement Using Iohexol

Glomerular filtration rate was measured using an iohexol clearance test on the following schedule: once during acclimation (Day −5); and days 13, 28, 57, 99, 121, 150 and 182.

Cats were fasted for at least 6 hours prior to the procedure. A dose of 300 mg iodine/kg (OMNIPAQUE®, iohexol injection, Nycomed Inc, Princeton, NJ), was administered via IV injection over approximately 10 seconds. Blood samples were obtained prior to injection, and at 2, 3, and 4 hours post iohexol administration (±2 min) on Days −5, 13 and 28; and at 2, 3, and 4 hours post iohexol administration (±2 min) on Days 57, 99, 121, 150 and 182. Approximately 2.5 mL of blood was collected via jugular venipuncture into one Standard Serum Tube. The SSTs were allowed to clot for at least 30 minutes after which they were centrifuged at 3000 rpm for 10 minutes. Serum was divided into two approximately equal aliquots and transferred into two labeled microtubes. Serum was transferred into frozen storage (≤−70° C.) within 90 minutes of collection. Samples were measured for iohexol clearance using a validated ICP/MS assay.

Urine Specific Gravity and Protein/Creatinine Ratio

Urine was collected from each cat on the following schedule: once during acclimation Day −7; and days 7, 14, 28, 56, 97, 120, 149 and 181.

Approximately 1 mL of urine was collected via either free catch/catheterization/cystocentesis and transferred to a tube containing no additive. For the purposes of urine collection that was performed using either catheterization or cystocentesis, cats were sedated using propofol to allow for urine collection. Urine specific gravity was measured within three hours of collection using a refractometer. Following specific gravity measurement, samples were analyzed for protein/creatinine ratio.

Body Weight

Each cat's body weight was measured using a calibrated scale once during acclimation (Day −7) and every four weeks+/− one day commencing on Day 5.

Feeding Program and Schedule

Standard commercially available cat food was fed to the cats at the recommended rates i.e. approximately 300 g/cat/day from Study Day −7 until Study Day 9; and were fed approximately 400 g/cat/day from Study Day 10 until the end of the study. On days of blood sampling (clinical pathology), diet was withdrawn the evening prior to sampling.

During the following periods, −3 to 3, 10 to 17, 24 to 31, 38 to 45, 52 to 59, 66 to 73, 80 to 87, 94 to 101, 108 to 115, 122 to 129, 136 to 143, 150 to 157 and 164 to 171, the quantity of diet offered was weighed and recorded. The quantity of diet not consumed from the previous day was removed from each cat's pen and weighed and recorded. The food met or exceeded the latest National Research Council requirements for energy, protein, vitamins, and minerals for the species and age class.

Water Provision and Watering Program

During the study, cats had water available ad libitum via stainless steel bowls. During the following periods, −3 to 3, 10 to 17, 24 to 31, 38 to 45, 52 to 59, 66 to 73, 80 to 87, 94 to 101, 108 to 115, 122 to 129, 136 to 143, 150 to 157 and 164 to 171, the quantity of water offered (approximately 300 ml daily) was measured and recorded. The quantity of water remaining from the previous day was removed from each cat's pen and measured and recorded.

Collection of Serum for Biomarker Analysis

Blood was obtained from each cat for potential serum biomarker analysis as follows: once during acclimation Day −7; and days 7, 13 29, 56, 97, 120, 149 and 181. Urine was obtained from each cat for potential urine biomarker analysis as follows: once during acclimation Day −7; and days 7, 14, 28, 56, 97, 120, 149 and 181.

Approximately 2 mL of blood was collected using a suitably sized needle and syringe and transferred into a suitably labelled serum separator tube (SST). Serum separator tubes were allowed to clot for at least 30 minutes after which they were centrifuged at 3000 rpm for 10 minutes at room temperature. Serum was split into approximately 150 μL aliquots between two suitably labelled polypropylene microtubes and frozen at ≤−70° C. within 90 min of collection.

Serum Samples were Analyzed for Biomarkers.

Approximately 1 mL of urine was collected via cystocentesis/catheterization or free catch and transferred to chilled tubes containing no additive. Tubes were labelled with the study number, animal ID, date, and time point of collection. Tubes were placed on wet ice until transferred to frozen storage. Samples were frozen at ≤−70° C. within 90 min of collection. Due to the unpredictable availability of urine samples, i.e. bladders were palpable in order to obtain urine samples, efforts were made to obtain samples as close to the desired time point as possible.

Methods to Analyze Effectiveness

The following primary outcomes were analyzed to determine efficacy:

1) A reduction in serum creatinine levels during the course of the study.

2) An increase in GFR during the course of the study.

A repeated measures analysis was used to estimate mean relative changes in both serum creatinine levels and GFR compared to baseline for each sample during the study via a linear mixed model. In addition, the mean change in serum creatinine and GFR relative to both baseline and the final sample was calculated.

Descriptive statistics for changes in body weight were calculated.

For each cat, the IVP was to be considered effective if the cat achieved a 20% reduction in plasma creatinine level during the course of the study. The success criterion was that 50% of the cats must demonstrate IVP effectiveness; OR For each cat, the IVP was to be considered effective if the cat achieved a 20% increase in GFR during the course of the study. The success criterion was that 50% of the cats must demonstrate IVP effectiveness.

For each cat, the IVP was to be considered safe if no serious adverse events that might be attributed to the IVP were observed. In addition, the product must be acceptable to the cats, with low incidence rates for adverse events in terms of number of animals affected and categories of events occurring.

Results and Discussion (Example 6)

Eighteen animals met the inclusion criteria. All procedures, i.e. dosing, general health observations, clinical observations, veterinary examinations, bodyweight measurements, diet consumption measurements, water consumption measurements, blood sampling and urine collection were performed at the specified time points.

Plasma Creatinine Levels

Statistical analysis results show that there was a significant decrease in plasma creatinine on Day 28 only ($P=0.0283$) compared to baseline. A 20% decrease of this parameter was observed in four animals on this day.

GFR Levels

Figure 10:
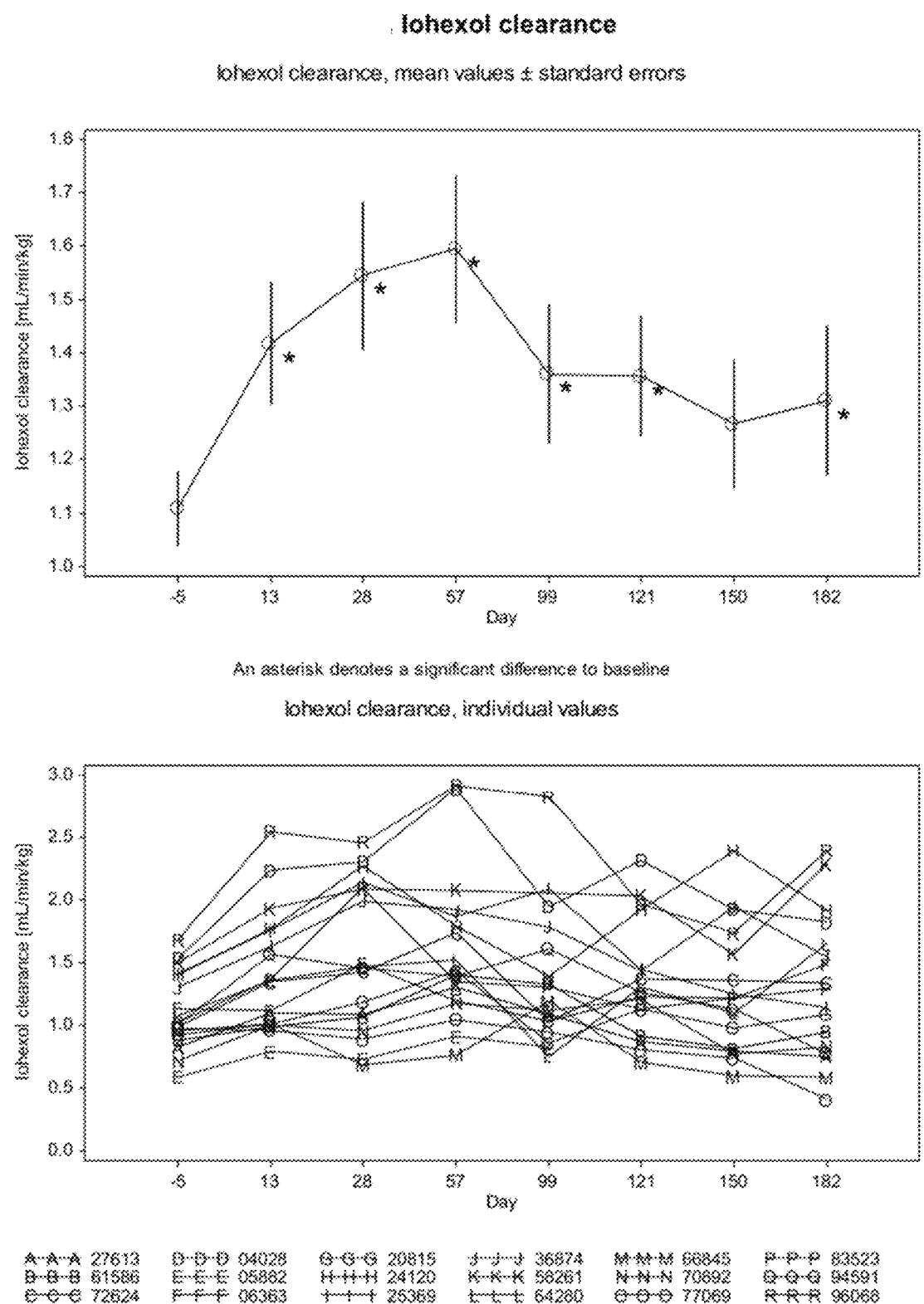
FIG. 10 depicts iohexol clearance results for individual animals, mean values, and statistics for Example 6.

Statistical analysis results show that there was a significant increase in GFR on Days 13, 28, 57, 99, 121 and 182 compared to baseline ($P<0.0001$ for Days 13 to 99 inclusive; $P=0.0029$ and $P=0.0225$ for Days 121 and 182 respectively). Greater than 50% of the cats demonstrated a 20% increase in GFR on Days 13, 28, 57 and 99. Iohexol clearance results for individual animals, mean values, and statistics are provided in FIG. 10.

Bodyweight

Figure 11:
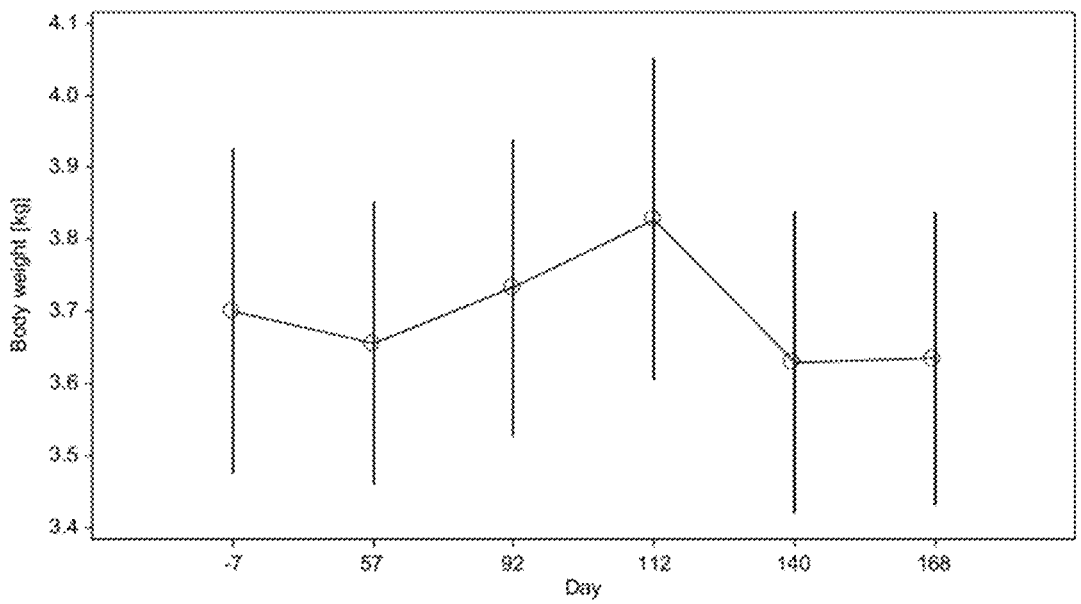
FIG. 11 depicts bodyweight results for individual animals, mean values, and statistics for Example 6.
Figure 11:
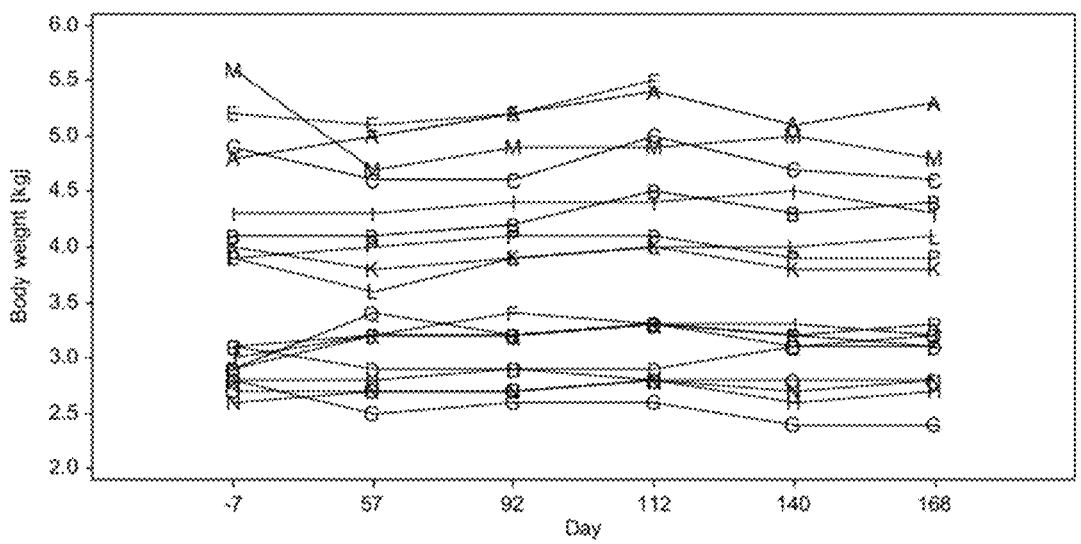

During the course of the study (i.e. from Day −7 to Day 168), nine cats gained weight, three cats maintained weight and five cats lost weight (range of weight loss was 0.1 kg-0.8 kg). The animal that died on Day 120 had gained weight from Day −7 to Day 112. Statistical analysis showed that there was no significant difference ($P>0.05$) in bodyweight at any timepoint compared to baseline during the study. Bodyweight values for individual animals, mean values, and statistics are provided in FIG. 11.

Diet Consumption

Statistical analysis results show that there was a significant increase in diet consumption on Days 14, 42, 70, 84, 112, 126, 140 and 154 compared to baseline ($P<0.05$).

Water Consumption

Statistical analysis results show that there was a significant increase in water consumption on from Day 42 to Day 168 inclusive compared to baseline (P<0.05).

Urinalysis

Figure 12:
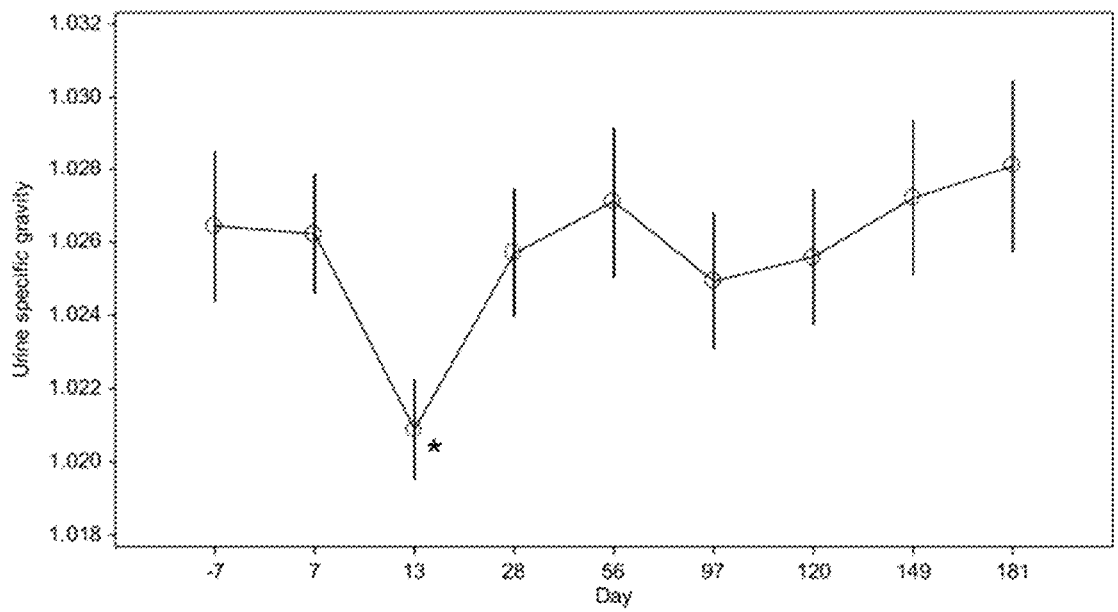
FIG. 12 depicts urinalysis results for individual animals, mean values, and statistics for Example 6.
Figure 12:
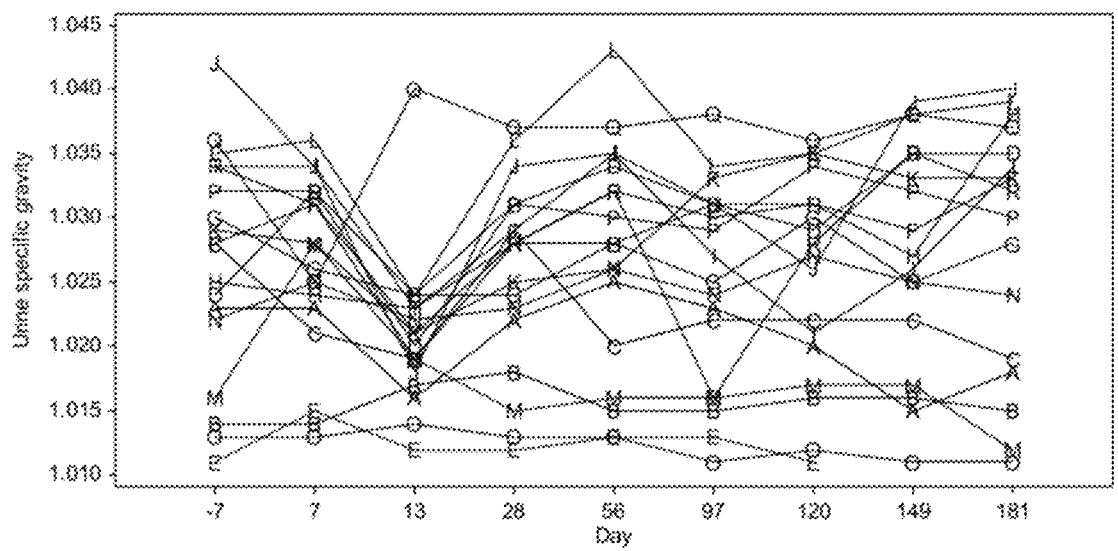
Figure 12:
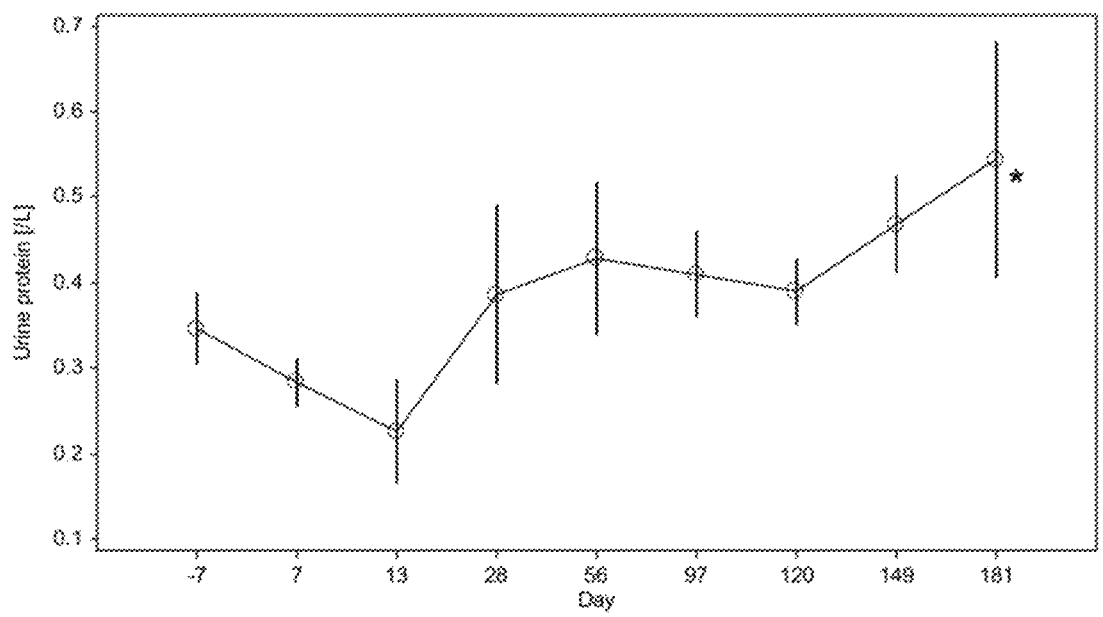
Figure 12:
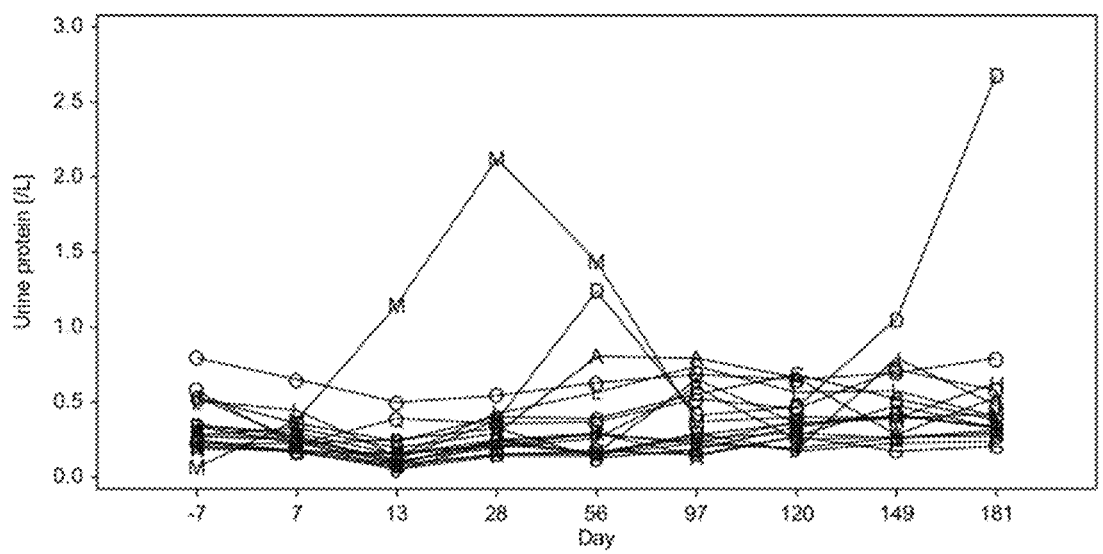
Figure 12:
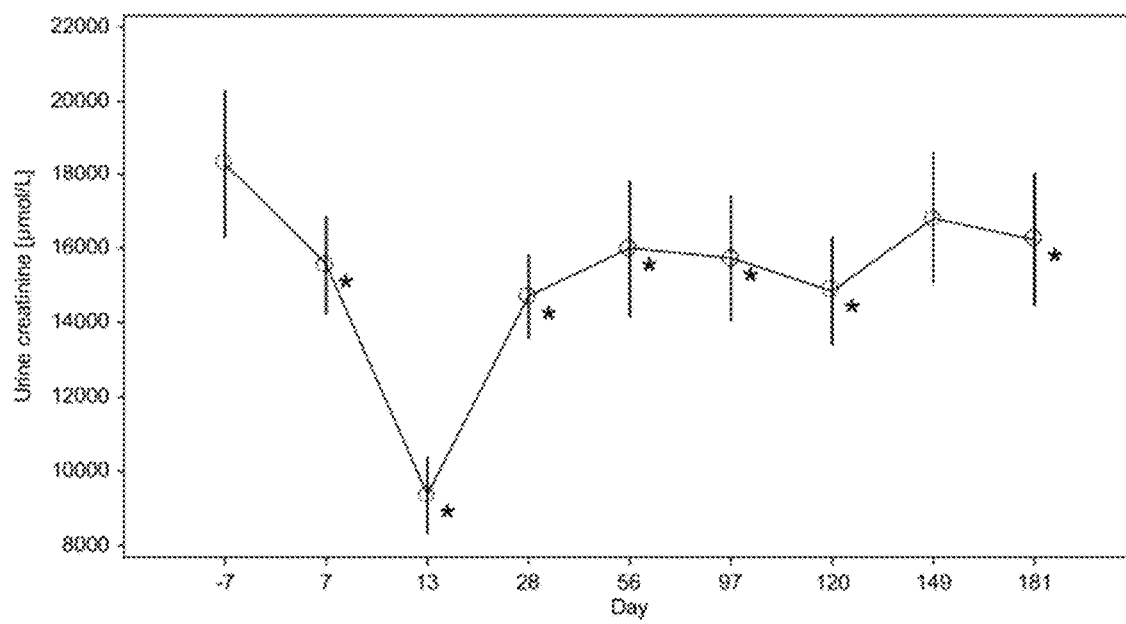
Figure 12:
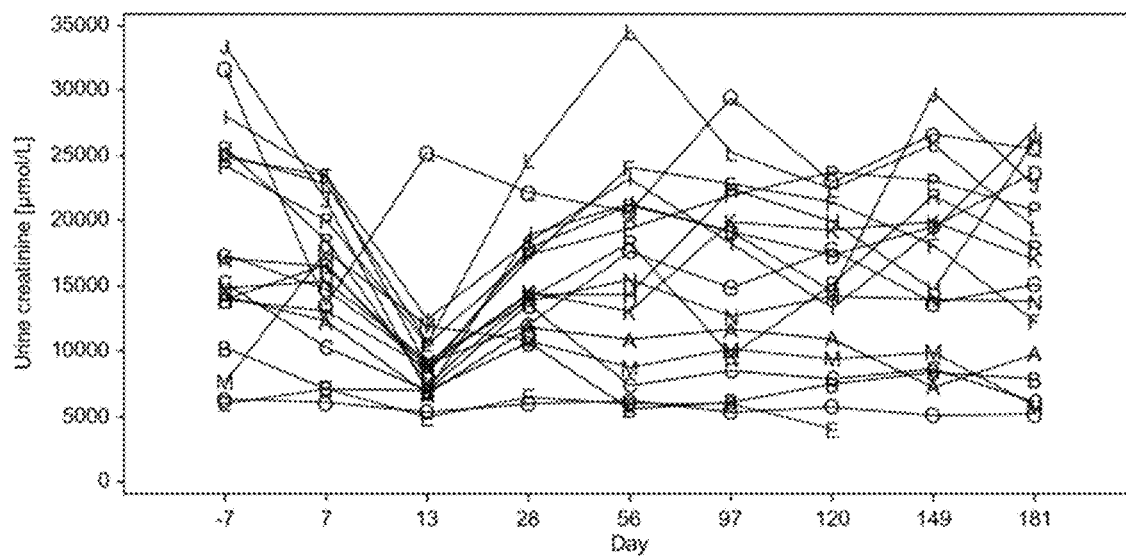
Figure 12:
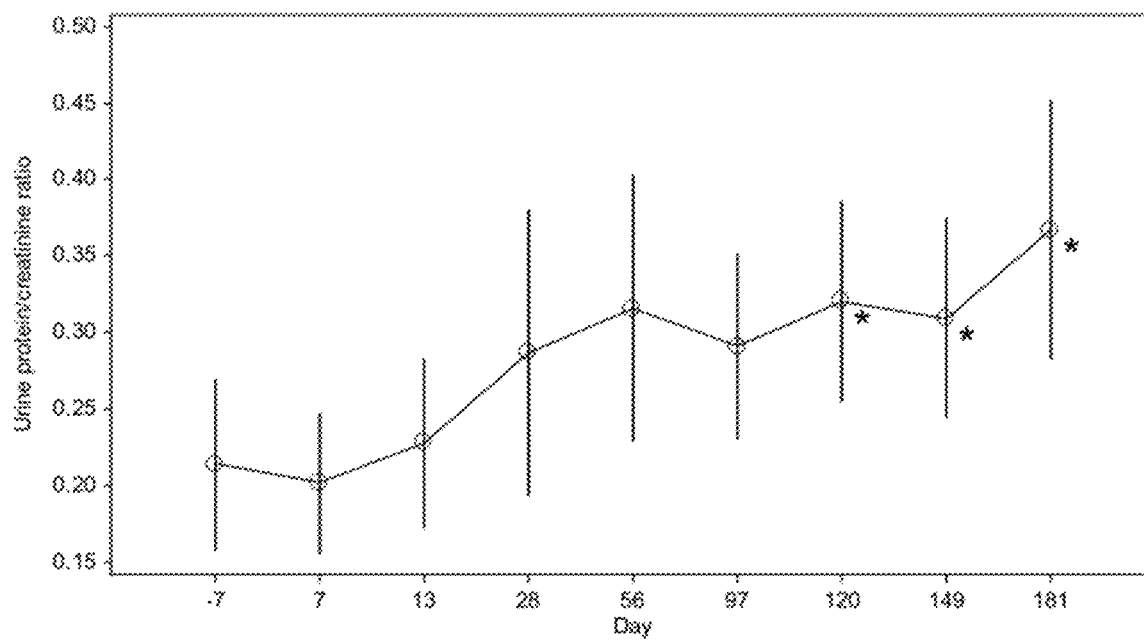
Figure 12:
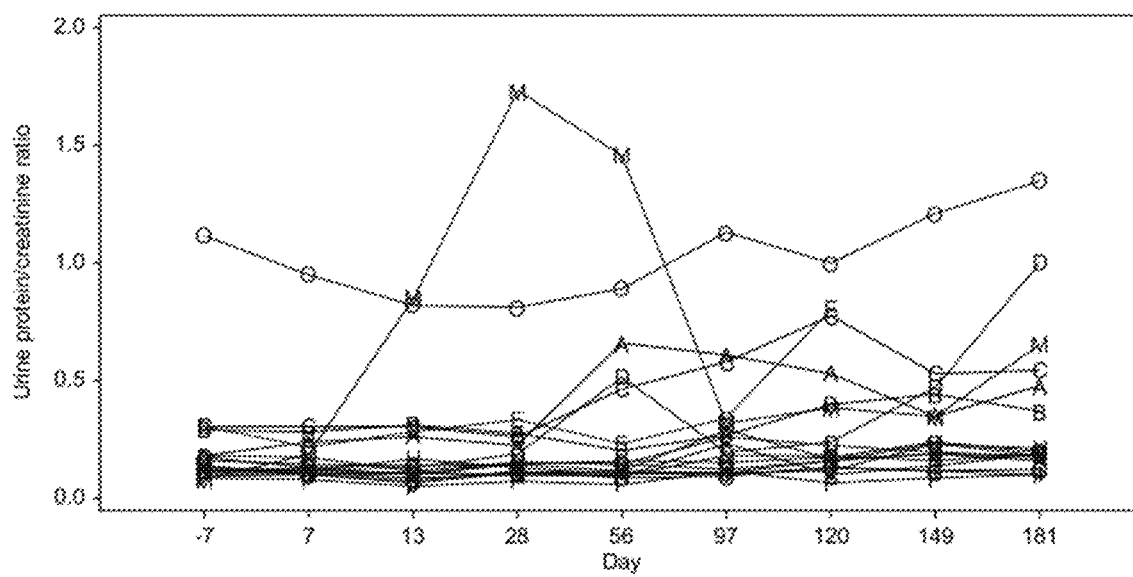

Urinalysis results for individual animals, mean values, and statistics are provided in FIG. 12. Statistical analysis results show that compared to baseline:
1) Urine specific gravity was significantly decreased on Day 13 only (P<0.0001).
2) Urine protein was significantly increased on Day 181 only (P=0.0221).
3) Urine creatinine was significantly decreased on Days 7, 13, 28, 56, 97, 120 and 181 (P<0.05).
4) Urine protein/creatinine ratio was significantly increased on Days 120, 149 and 181 (P<0.05).

Conclusion (Example 6)

Based on glomerular filtration rate, the IVP (allogeneic feline uterine derived regenerative cells) is effective as a treatment for chronic kidney disease in cats as a 20% increase in iohexol clearance was observed in at least 50% of nephrectomised cats on Days 13, 28, 57, and 99. Statistical improvements in GFR were observed throughout the 6 month evaluation period, excluding Day 150.

Based on plasma creatinine results, a decrease in plasma creatinine was only observed on Day 28. On this day, 22% of cats achieved a 20% reduction in this parameter.

The IVP was well tolerated at a dose of 30M cells administered twice at a 2-week interval during the study.

Example 7. Treatment of Canine CKD with Canine Uterine-Derived Regenerative Cells It is envisioned that dogs (canines) can be treated for CKD using canine uterine-derived regenerative cells in a similar manner as disclosed in Example 6.

Canine uterine tissue from a donor is prepared according to Protocol B, Protocol C, or similar protocol to result in a heterogeneous cell population including both vimentin-only singly positive and vimentin/cytokeratin doubly positive cell populations (e.g. a population of mesenchymal progenitor cells and a population of epithelial progenitor cells). In some embodiments, the ratio of vimentin-only singly positive cells to vimentin/cytokeratin doubly positive cells is approximately 50%:50% or about 50%:50%, but this ratio can diverge as much as 80%:20% or 20%:80% (V+/C−:V+/C+).

Like Example 6, a dog subject with CKD may be treated with 30 million total cells of this heterogeneous cell population in at least one IV administration. However, depending on the size and weight of the dog, this amount may be optimized, such as 1 million, 5 million, 10 million, 20 million, 25 million, 30 million, 31 million, 32 million, 33 million, 34 million, 35 million, 36 million, 37 million, 38 million, 39 million, 40 million, 50 million, 60 million, 70 million, 80 million, 90 million, or 100 million total cells, or any number of cells within a range defined by any two of the aforementioned amounts. After administration of the heterogeneous cell composition, positive effects in kidney function are observed in the dog subject.

Example 8. Treatment of Canine or Feline Diseases with Autologous or Allogeneic Uterine-Derived Regenerative Cells A dog or cat patient presents with a disease. This disease may be idiopathic or related to an autoimmune disease or aging. This disease may be chronic kidney disease, atopic dermatitis, immune mediated arthritis, hepatitis, liver disease, inflammatory bowel disease, osteoarthritis, intravertebral disc disease, keratoconjunctivitis sicca (dry eye), pancreatitis, fibrosis, sclerosis, amyloidosis, immune mediated polyarthritis, or wounds. An autologous or allogeneic heterologous cell composition prepared from uterine tissue and including both vimentin-only singly positive and vimentin/cytokeratin doubly positive cell populations is administered to the dog or cat patient. This heterologous cell composition may be prepared according to Protocol B, Protocol C, Protocol D or a similar protocol. In some embodiments, the ratio of vimentin-only singly positive cells to vimentin/cytokeratin doubly positive cells in this heterologous cell composition is approximately 50%:50% or about 50%:50%, but this ratio can diverge to 80%:20% or 20%:80% (V+/C−:V+/C+). The heterologous cell composition may be administered intravenously or another enteral or parenteral route.

For atopic dermatitis, the dog or cat patient experiences a reduction in discomfort and pruritic symptoms after administration of the heterologous cell composition. In some embodiments, the heterologous cell composition is administered with another therapeutic for atopic dermatitis, such as steroids, glucocorticoids, hydrocortisone, ciclosporin, oclacitinib, lokivetmab, antihistamines, hydroxyzine, chlorpheniramine, or topical ointments and shampoos. In other embodiments, the heterologous cell composition is administered in lieu of another therapeutic because, e.g., the other therapeutic does not have a significant effect in treating the atopic dermatitis, the other therapeutic is short lasting and requires multiple applications, or the other therapeutic causes side effects that are detrimental to the dog or cat patient.

For osteoarthritis or other immune mediated arthritides, the dog or cat patient experiences a reduction in joint pain and inflammation after administration of the heterologous cell composition. The composition may be administered systemically or intra-articularly. In some embodiments, the heterologous cell composition is administered with another therapeutic for osteoarthritis or other immune mediated arthritides, such as steroids, corticosteroids, non-steroidal anti-inflammatory drugs, Platelet-rich Plasma (PRP), glucosamine, PSGAG, hyaluronic acid, or opiates. In other embodiments, the heterologous cell composition is administered in lieu of another therapeutic because, e.g., the other therapeutic does not have a significant effect in treating the osteoarthritis or other immune mediated arthritides, the other therapeutic is short lasting and requires multiple applications, or the other therapeutic causes side effects that are detrimental to the dog or cat patient.

For keratoconjunctivitis sicca, the dog or cat patient experiences a full or partial restoration of tear production and/or reduction in inflammation of the lacrimal glands, conjunctiva, and cornea after administration of the heterologous cell composition. In some embodiments, the heterologous cell composition is administered with another therapeutic for keratoconjunctivitis sicca, such as artificial tears, corticosteroids, cyclosporine, pimecrolimus, or tacrolimus. In other embodiments, the heterologous cell composition is administered in lieu of another therapeutic because, e.g., the other therapeutic does not have a significant effect in treating the keratoconjunctivitis sicca, the other therapeutic is short lasting and requires multiple applications, or the other therapeutic causes side effects that are detrimental to the dog or cat patient.

For wounds, the dog or cat patient experiences more rapid healing of the wound, reduced risk of infection, and/or reduction in pain or discomfort due to the wound after administration of the heterologous cell composition. In some embodiments, the heterologous cell composition is administered with another therapeutic for wound healing, such as topical antibiotics. In other embodiments, the heterologous cell composition is administered in lieu of another therapeutic because, e.g., the other therapeutic does not have a significant effect in treating the wound, the other therapeutic is short lasting and requires multiple applications, or the other therapeutic causes side effects that are detrimental to the dog or cat patient.

For hepatitis and other liver disease, the dog or cat patient experiences reduction of liver inflammation and scarring, and improvement of liver function after administration of the heterologous cell composition.

For inflammatory bowel disease, the dog or cat patient experiences reduction of intestinal inflammation, increased appetite, and less vomiting after administration of the heterologous cell composition.

For intervertebral disc disease, the dog or cat patient experiences reduction of inflammation and pain in the spine after administration of the heterologous cell composition.

For pancreatitis, the dog or cat patient experiences reduction of pancreatic inflammation, increased appetite, and less vomiting after administration of the heterologous cell composition.

For fibrosis, the dog or cat patient experiences reduction in fibrotic scarring of organs such as the liver, lungs, heart, kidney, or other organs after administration of the heterologous cell composition.

For sclerosis, the dog or cat patient experiences improved sight and reduction of cataract-like symptoms after administration of the heterologous cell composition. In some embodiments, the heterologous cell composition is administered intraocularly.

For amyloidosis, the dog or cat patient experiences reduction in amyloid deposits throughout the body such as the kidney, liver, or heart after administration of the heterologous cell composition.

Example 9. Autologous Uterine-Derived Regenerative Cells

All of the preceding Examples can be applied using autologous cells. The uterine tissue used to obtain the heterologous cell compositions derived herein can be obtained or derived from a canine or feline patient that has a disease and is in need of the heterologous cell compositions. In some embodiments, the uterine tissue is obtained from the canine or feline patient when the patient is younger. In some embodiments, the uterine tissue is obtained from the canine or feline patient during a spay (ovariohysterectomy or hysterectomy) procedure, which usually takes place at a young age, such as 1, 2, 3, 4, 5, 6, 7, 8, 9, 10, 11, or 12 months old. In some embodiments, the uterine tissue is cryogenically banked. For example, the uterine tissue is stored at low temperatures (i.e. liquid nitrogen temperatures) in a cryopreservation medium. When the canine or feline patient is in need of the heterologous cell compositions described herein, the uterine tissue is thawed and processed according to the protocols described herein or a similar protocol to produce the heterologous cell compositions. The heterologous cell compositions can then be administered to the canine or feline patient as an autologous composition that causes little or no negative immune-related effects. In some embodiments, the uterine tissue is processed according to the protocols described herein or a similar protocol, and the resultant heterogeneous cell compositions are cryogenically banked. When a canine or feline patient is in need of the heterologous cell compositions, they are thawed and administered to the canine or feline patient as an autologous composition that causes little or no negative immune-related effects. Optionally, the heterogeneous cell compositions are expanded in cell culture to obtain a large number of cells for cryogenic banking, such that the canine or feline patient can be administered autologous compositions more than once from a single uterine tissue donation.

Example 10. Clinical Doses Prepared Using Enzymatic Digestion of Canine and Feline Uterine Tissue and Culture Process (Protocol C)

Uterine tissue obtained from canine and feline donor spay procedures was received for processing within 24 hours of surgical procedure. The uterus was isolated by dissection from other tissues present in the spay procedure. The uterine tissue was minced into 2 mm by 2 mm tissue pieces, and digested with collagenase and thermolysin (both from Vita-Cyte, Inc.; at 13 mg collagenase and 0.2 mg thermolysin per gram of uterine tissue). The digestion was performed in 4.5 mL DPBS at 37° C. for 1 hour with periodic manual shaking. Corning DMEM (HG, high glucose; Dulbecco's Modified Eagle Medium) culture medium containing 10% fetal bovine serum (FBS) was added to quench the reaction. The digest, composed of released cells and tissue explants, was plated in T225 flasks (0.1 g tissue/flask) and incubated at 37° C., 5% $CO_2$ and 100% humidity. The culture medium was supplemented with 8 ng/mL recombinant human fibroblast growth factor-basic active protein (rhFGF-2; CellGenix, Inc.), 6 mM L-glutamine and 10% FBS. The T225 flasks were processed on Day 3 to remove the tissue bits or explants and spent medium, and fresh culture medium was added. Once the flasks reached 70-80% confluence, the cells were released by treating with TrypLE™ (Gibco), washed, counted in the NucleoCounter NC-200, and cryopreserved in 1 mL of cryopreservation medium (CS10; BioLife Solutions). The cryovials (CellSeal, Sexton Biotechnologies) were transferred to a specialized cooling chamber for CellSeal vials, which was placed in a −80° C. freezer overnight, after which the vials were transferred to the vapor phase of monitored liquid nitrogen ($LN_2$) storage. Each vial contained $5 \times 10^6$ cells. These vials were designated as Passage 1 (P1). Culturing of cells was continued in T225 flasks in DMEM (HG) with 10% FBS, 6 mM L-glutamine, 8 ng/mL FGF-2, and passaged when the cells reached approximated 70-80% confluence. At each passage, cells were released with TrypLE treatment, washed, counted, and reseeded in appropriate culture flasks at 4000-10000 cells/cm². At the end of the culture cycles (e.g., Passage 4 or 5), Uterine Tissue-derived Regenerative Cells (URCs) were cryopreserved in CS10 (BioLife Solutions), transferred to a −80° C. freezer overnight, and placed in vapor phase liquid nitrogen storage.

Example 11. Feline Uterine Tissue-Derived Adherent Cells in Culture

Figure 13A:
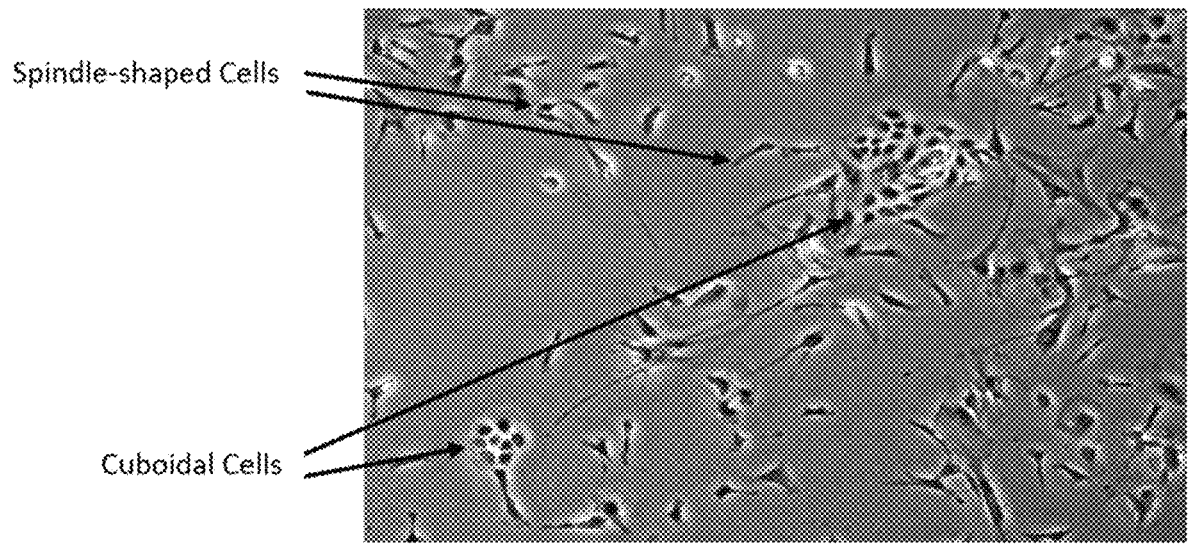
FIG. 13A depicts an exemplary feline uterine-derived regenerative cell composition at passage 4 of cell culture. Both spindle-shaped and cuboidal cells are observed in the cell population.

Feline uterine tissue-derived cells, when cultured in DMEM with 10% FBS and FGF-2 (8 ng/mL) according to Protocol C (Example 10) show adherent cells as depicted in FIG. 13A (ID: S-001, Passage 4).

There are two obvious cell types present in FIG. 13A (S-001) that show persistent growth of both the spindle-shaped cells and the cuboidal-shaped cells through Passage 4. Passaging involves treating adherent cells with an enzymatic agent (e.g. TrypLE, Gibco) that releases the attached cells from their anchorage to the plastic container. The detached cells are seeded into fresh culture containers. Thus, in the example as depicted in FIG. 13A, the cells have been detached and re-seeded four times. The feline URC preparation is composed of detached cells cryopreserved in an appropriate cryopreservation medium (e.g. CS10, BioLife Solutions).

Example 12. Canine Uterine Tissue-derived Adherent Cells in Culture

Figure 13B:
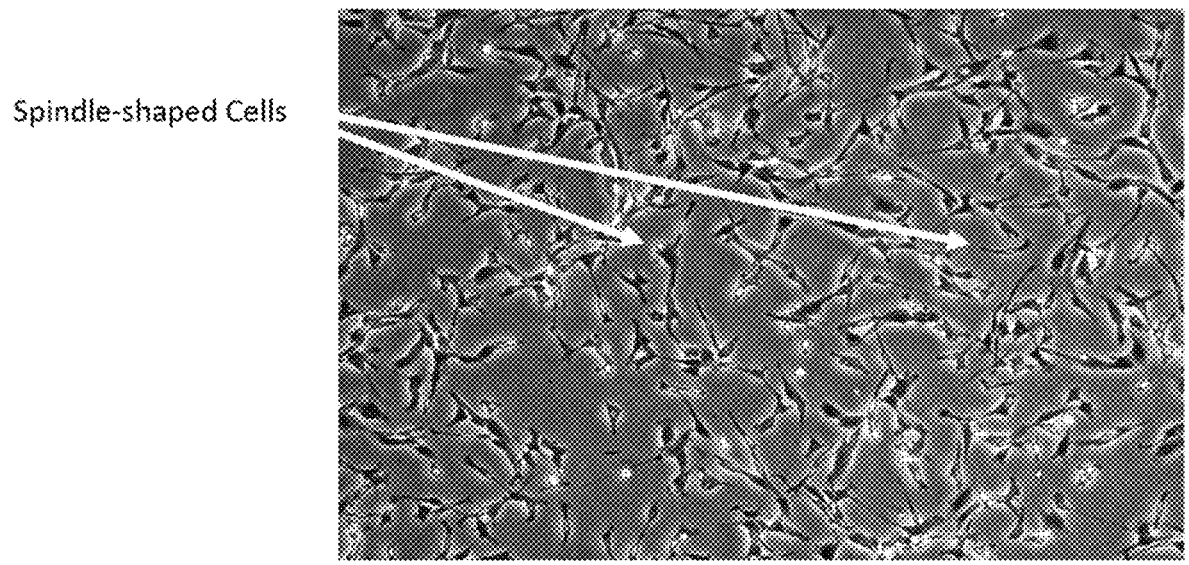
FIG. 13B depicts an exemplary canine uterine-derived regenerative cell composition at passage 4 of cell culture. Spindle-shaped cells are observed in the cell population.

Canine uterine tissue-derived cells, when cultured in DMEM with 10% FBS and FGF-2 (8 ng/mL) according to Protocol B show adherent cells as indicated in FIG. 13B (S-002, Passage 4). Spindle-shaped cells are present during the culturing process through Passage 4. Passaging involves treating adherent cells with an enzymatic agent (TrypLE, Gibco) that releases the attached cells from their anchorage to the plastic container. The detached cells are seeded into fresh culture containers. Thus, in the example as depicted in FIG. 13B, the cells have been detached and re-seeded 4 times. The canine URC preparation is composed of detached cells cryopreserved in an appropriate cryopreservation medium (e.g. CS10, BioLife Solutions).

Example 13. Trilineage Differentiation of Canine and Feline URC Preparations

Both canine and feline URC preparations according to Protocol B or Protocol C have been differentiated into adipo-, chondro-, and osteogenic cell lineages when cultured in the appropriate induction medium. The trilineage differentiation conditions are shown in Table 9.

Each donor URC preparation was evaluated for trilineage differentiation in response to induction medium and was paired with cells maintained in culture medium as a control. After staining was completed, the wells were imaged with a phase contrast microscope fitted with an Amscope MD camera. Specific assay conditions for both canine and feline trilineage differentiation are as follows:

Adipogenesis: Progenitor cells that undergo adipogenic differentiation will develop vacuoles in the cells' cytoplasm that contain lipid, which is similar to how adult adipocytes store lipid. Wells on a 6-well plate for the adipogenic differentiation assay were examined after 14 days of culture for evidence of lipid vacuole formation within the cells. The wells were fixed after an inoculation period of 21 days. The fixation process used Oil Red 0 as the stain, which is preferentially retained in lipid-containing vacuoles (droplets) that form in a cell's cytoplasm. It is critical not to allow the cells to dry for more than 30 seconds during the staining procedure. Cells were considered to have undergone adipogenic differentiation when they are red-stained lipid "droplets" or vacuoles within the cytoplasm of the cells.

Chondrogenic Differentiation: Cells were seeded into a 6-well plate in concentrated droplets and incubated for 3 weeks in the induction medium. Progenitor cells that underwent chondrogenic differentiation typically grew in "nodules", which contain a variety of extracellular proteins, including collagen. Alcian blue was used to stain collagen present in the extracellular matrix.

Osteogenic Differentiation: Cells were seeded into a 6-well plate and incubated overnight before having the medium in the test wells switched to induction medium. Incubation was continued for 3 weeks. Cells that responded to osteogenic induction medium showed extensive deposition of mineralized extracellular matrix that was synthesized by the cells that are differentiating along the osteogenic lineage. Alizarin Red was used to stain the calcium that is present in the osteoblast-secreted mineralized extracellular matrix.

TABLE 9

Conditions for Performing Differentiation Assay

| Assay | Cells/well | Culture Conditions | Induction Medium |
| --- | --- | --- | --- |
| Adipogenesis | 100,000 cells/well in 3 mL | Allow cells to reach approximately 70% confluence in each well of a 6-well plate<br>Replace three wells with Induction Medium<br>Replace control wells with culture medium/1% FBS<br>Examine for lipid droplet formation after 21-days | Gibco StemPro Adipogeneic Differentiation Medium |
| Chrondrogenesis | 50 μL drops of 4 × $10^6$ cells/mL placed in each well | After placing multiple 50 μL drops in each well of a 6-well plate, the plate is incubated overnight<br>Induction medium is added to three wells and culture medium is added to three wells<br>Media is replaced every three days<br>Culture is continued for 3-weeks | Cell Applications CM-1 |
| Osteogenesis | 30,000 cells/$cm^2$ in 3 mL | Seeded 6-well plates are incubated overnight<br>Induction medium is used to replace the culture medium in three wells and fresh culture medium replaces the medium in three wells for the control<br>Media is replaced every three days<br>Culture is continued for 3-weeks | Cell Applications OM-1 |

Figure 14A:
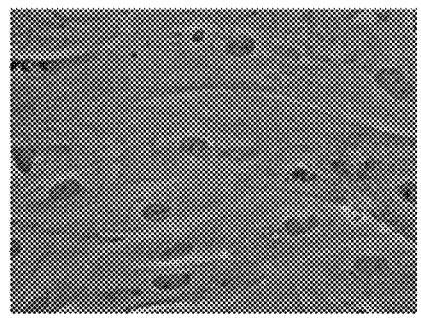
FIG. 14A depicts adipogenic staining of feline and canine URC populations after incubation in either control medium or adipogenic induction medium.
Figure 14A:
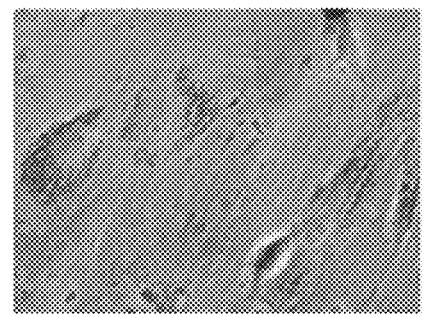
Figure 14A:
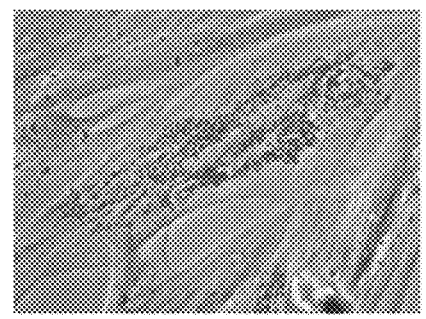
Figure 14B:
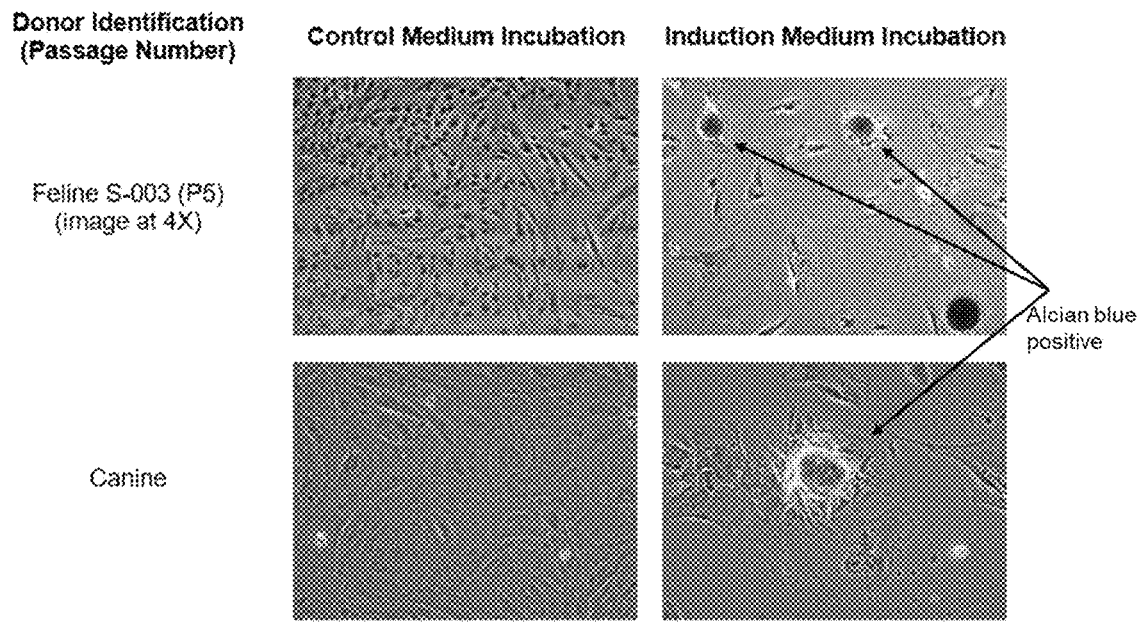
FIG. 14B depicts chondrogenic staining of feline and canine URC populations after incubation in either control medium or chondrogenic induction medium.
Figure 14C:
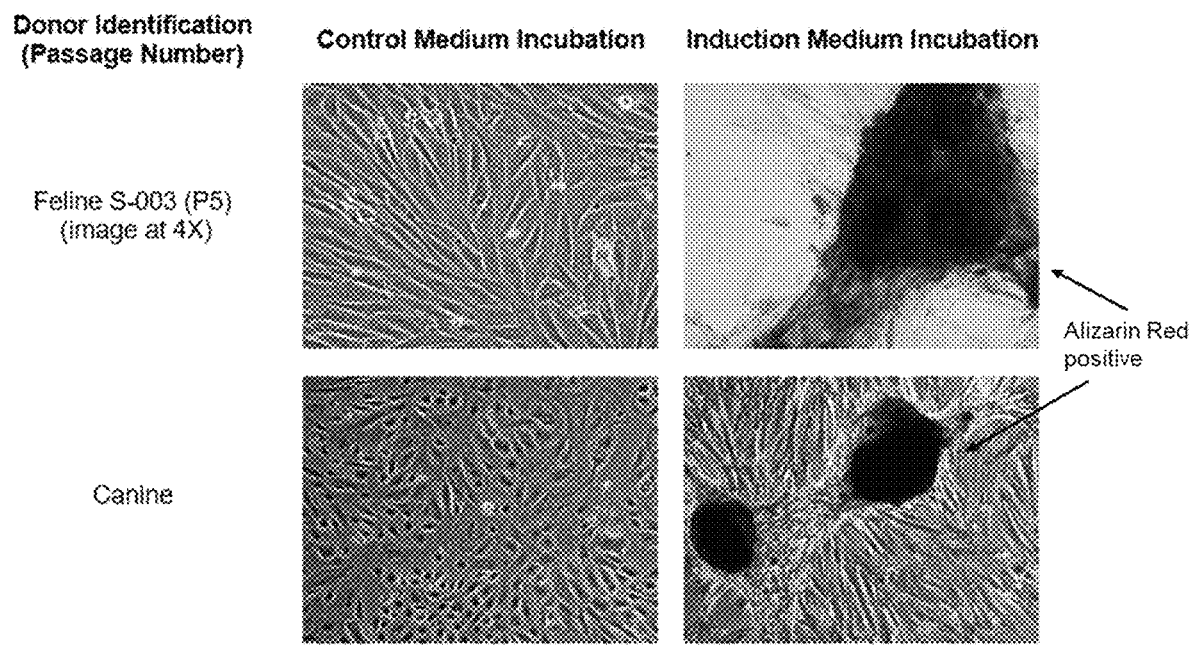
FIG. 14C depicts osteogenic staining of feline and canine URC populations after incubation in either control medium or osteogenic induction medium.

Each set of images depicted in FIGS. 14A-C show a positive reaction for both the feline and canine URC preparations when treated with induction medium to establish trilineage differentiation.

Example 14. Single Color Positive Frequencies for Canine and Feline URC Preparations Cells were analyzed with commercially available, directly-labelled antibodies reactive with CD34, CD45, CD90 (canine and feline; ThermoFisher), CD44 (canine and feline; BioLegend), CD105 (feline; ThermoFisher), MHCII (canine; ThermoFisher) and Live/Dead (canine and feline; 7-AAD, Invitrogen). The cells were incubated in the previously optimized reagents for 30 minutes in the dark on ice, prior to being assessed for reactivity. All events were evaluated first with Live/Dead stain, and only viable, single cell events were analyzed for reactivity with the panel of surface-reactive CD markers. Samples were evaluated on the Attune Flow Cytometer. Data was analyzed with FloJo (BD Life Sciences).

Multiple unrelated feline and canine URC preparations, prepared using Protocol B and Protocol C, respectively, have been assessed for their reactivity with various CD marker reagents that have been qualified for reactivity with canine or feline cells. Table 10 shows the single color positive frequencies for feline URC preparations, while Table 11 shows the single color positive frequencies for canine URC preparations.

TABLE 10

Single Color Positive Frequencies for Feline URC Preparations

| Sample ID | Passage # | Single Color Positive Frequencies (%) | | | | |
|---|---|---|---|---|---|---|
| | | CD34 | CD45 | CD44 | CD90 | CD105 |
| S-004 | 3 | 0.04 | 0.06 | 99.8 | 43.6 | 95.6 |
| S-005 | 3 | 0.03 | 1.25 | 98.4 | 56.8 | 87.4 |
| S-006 | 3 | 0.18 | 0.74 | 99.2 | 60.0 | 77.4 |
| S-007 | 4 | 0.09 | 0.82 | 98.6 | 61.3 | 91.9 |
| S-008 | 4 | 0.34 | 0.87 | 99.6 | 81.8 | 95.5 |

TABLE 11

Single Color Positive Frequencies for Canine URC Preparations

| Sample ID | Passage # | Single Color Positive Frequencies (%) | | | | |
|---|---|---|---|---|---|---|
| | | CD34 | CD45 | CD44 | CD90 | MHCII |
| S-009 | 4 | 0.14 | 0.51 | 99.6 | 70.7 | NA |
| S-010 | 3 | 0.94 | 0.45 | 100 | 82.6 | 0.45 |
| S-011 | 4 | 0.12 | 0.05 | 99.3 | 56.2 | 1.7 |
| S-012 | 4 | 0.58 | 0.04 | 99.6 | 99.2 | NA |
| S-013 | 4 | 0.11 | 0.02 | 99.5 | 99.2 | NA |
| S-014 | 4 | 0.21 | 0.04 | 99.9 | 99.9 | NA |

The CD marker profiles shown in Table 10 and Table 11 are generally based on a conventional consensus for how to characterize progenitor cells. The first requirement for a cell to be considered as a stromal cell is that the cells are plastic adherent and that they can be induced to differentiate in vitro into chondro-, osteo- and adipogenic cell lineages. Furthermore, the CD marker single positive frequencies for a human "mesenchymal stem cell" (MSC) that has been cultured as follows: 1) Positive reactivity (e.g. >95%) for CD73, CD90 and CD105; and 2) Negative reactivity (e.g. <2%) for CD34 and CD45, among others. There is also a requirement for human MSCs that they are "negative" for HLA-DR, which for non-human MSCs would mean that MHCII is negative.

As shown in FIGS. 13A-B, feline and canine URCs grow readily as adherent cells. Representative donors for both feline and canine URCs have been shown to differentiate into chondro-, osteo-, and adipogenic cell lineages, as shown in FIGS. 14A-C. As seen in Tables 10 and 11, cultured feline and canine URCs are clearly negative for CD34 and CD45, and there is some evidence that canine URCs are MHCII negative. CD44 is associated with progenitor cells. However, while CD44 is very positive, CD90 and CD105 are positive in canine and/or feline URCs but do not achieve the generally accepted >95% level for cells to be considered as MSCs. Thus, the uterine tissue-derived URCs as disclosed herein do not resemble the classical human-derived MSC. Nonetheless, the feline and canine URCs as disclosed herein display plastic adherent growth, differentiate into three adult cell lineages (adipo-, chondro-, and osteo-), and display a CD marker profile that traditionally is associated with stem/progenitor cells, supporting their status as a progenitor cell derived from uterine tissue in dogs and cats.

Additional characteristics of the canine and feline URC preparations further point to the URC preparations herein as unique progenitor cells as established in the following Examples.

Example 15. Dual Expression of Vimentin and Cytokeratin-18 in Adherent Feline Uterine Tissue-Derived Cells by Immunofluorescence While there were two distinctly shaped types of cells in a feline URC preparation durably present in successive passaging and reseeding cycles, as depicted in FIG. 13A, it was surprising to find that some of the cells present in feline uterine tissue-derived cell cultures display cellular characteristics that are associated with progenitor cells as well as epithelial cells in the same cell. Vimentin is associated with cells that are considered to be progenitor-type cells, while Cytokeratin-18 is associated with cells that are epithelial-like and that typically would not be expected to express Vimentin.

The technique of immunofluorescence (IF) was used to visualize the presence or absence of Vimentin and Cytokeratin-18 in adherent URC cultures through a staining and visualization process. Cells were obtained either from a growing culture container or from a vial of cryopreservation cells and seeded in special culture chambers (Lab Tech II CC2 Chamber Slides) that are incubated overnight at 37° C./5% $CO_2$. During the overnight incubation in DMEM with 10% FBS and FGF-2 at 8 ng/mL, cells attached to the container surface. After the overnight culture, the culture medium was removed, and a wash of the chamber was performed with PBS to remove the culture medium. The cells were fixed (Invitrogen, Image-iT Fixative/Permeabilization Kit: Fixative, Wash Buffer, Permeabilization Solution, Blocking Solution) for 15 minutes at room temperature, after which the fixative was removed, and the chamber was washed three times with Wash Buffer. A permeabilizing reagent (Image-iT Permeabilization Solution) was added to permeabilize the cells and incubated for 15 minutes at room temperature. Permeabilization is needed since both Vimentin and Cytokeratin are intracellular cytoskeletal proteins. After removing the permeabilizing solution and washing with Wash Buffer, the treated cell layer was blocked overnight with Blocking Solution. After washing the blocked cells with PBS, an anti-Vimentin reagent labeled with AlexaFluor 647 stain (abeam) and an anti-Cytokeratin-18 reagent labeled with FITC (abeam) were added to the chamber, which produces a red stained structure if Vimentin is present and a green stained structure if Cytokeratin-18 is present. After staining, the chamber(s) were imaged on an eVOS instrument (ThermoFisher). The staining patterns of two unrelated feline uterine tissue-derived preparations using Protocol C are depicted in FIGS. 15A-C and 16A-C.

In each set of images of the feline URC preparations shown in FIGS. 15A-C and 16A-C, the upper images (FIGS. 15A and 16A) shows numerous cells that are Vimentin-positive. The middle images (FIGS. 15B and 16B) shows fewer cells that are Cytokeratin-positive. Cells are identified in the merged, lower images (FIGS. 15C and 16C) that are positive for both Vimentin and Cytokeratin. Not every Vimentin-positive cell is also positive for Cytokeratin, nor is every Cytokeratin-positive cell also positive for Vimentin. However, it is evident that there is an unexpected presence of a population of dually stained cells present in multiple unrelated feline donor URC preparations. Thus, the dually-stained cells identify a persistent, smaller population of cells with both epithelial cell-like (Cytokeratin positive) and progenitor cell-like (Vimentin positive) characteristics present in a stable culture of progenitor-like cells and epithelial-like cells.

Example 16. Assessment of CD Marker Positive Frequency Demonstrates the Presence of Cells with Multiple Expression of Vimentin, Cytokeratin, CD44, and CD326

Cells have been assessed for their single color positive frequencies (Tables 10 and 11) in an assay that detects surface markers. However, as indicated in Example 15, it is possible to detect vimentin and cytokeratin in fixed and permeabilized cells. A modified staining assays was performed for flow cytometric analysis in which CD44 and CD326 reagents were incubated with the cells, but after washing the excess reagents away, the cells were fixed, permeabilized and blocked as described in Example 15 (Invitrogen, Image-iT Fixative-Permeabilization Kit), and reacted with labeled anti-vimentin (canine and feline; abeam) and anti-cytokeratin-18 (canine and feline; abeam) reagents. Samples were evaluated on the Attune Flow Cytometer. Data was analyzed with FloJo (BD Life Sciences).

Cells from multiple unrelated feline and canine donor uterine tissue-derived cultured cell preparations using Protocol C and Protocol B, respectively, were examined by flow cytometric assay for co-expression of CD44, CD326, Vimentin and Cytokeratin-18. CD44 is a marker of progenitor cells, while CD326 is a marker of epithelial cells. The double staining positive frequencies for Vimentin/Cytokeratin and CD44/CD326 are shown in Table 12 for the three donor feline URC preparations assessed. Multiple donor canine URC preparations were assessed for dual positive frequencies of CD44/CD326, CD44/Cytokeratin, CD44/Vimentin and Vimentin/Cytokeratin as shown in Table 13.

TABLE 12

Dual-expression Frequencies for Vimentin/Cytokeratin-18 and CD44/CD326 in Feline Donor Uterine Tissue-derived Preparations

| Sample ID | Passage Number | Dual-positive Frequency (%) | |
|---|---|---|---|
| | | CD44/CD326 | Vimentin/Cytokeratin |
| S-007 | 4 | 33.6 | 14.5 |
| S-008 | 4 | 12.1 | 5.92 |
| S-012 | 1 | 32.6 | 10.4 |
| S-012 | 4 | 14.6 | 1.52 |

TABLE 13

Dual-expression Frequencies for Vimentin/Cytokeratin-18 in Canine Donor Uterine Tissue-derived Preparations

| Sample ID | Passage Number | Dual-positive Frequency (%) | | | |
|---|---|---|---|---|---|
| | | CD44/CD326 | CD44/Cytokeratin | CD44/Vimentin | Vimentin/Cytokeratin |
| S-016 | 1 | NA | NA | NA | 20.9 |
| S-016 | 4 | NA | NA | NA | 11.6 |
| S-002 | 1 | NA | NA | NA | 7.78 |
| S-017 | 1 | 11.1 | 19.0 | 96.6 | 21.1 |
| S-017 | 4 | 5.4 | 17.7 | 99.2 | 6.6 |
| S-018 | 1 | 11.2 | 38.5 | 99.0 | 29.4 |
| S-018 | 4 | 2.4 | 11.9 | 97.4 | 9.4 |
| S-012 | 1 | 2.7 | 24.0 | 98.0 | 13.8 |
| S-012 | 4 | 0.4 | 9.2 | 99.0 | 9.2 |

As shown in Table 12, each of the feline donor cell preparations demonstrate the unexpected presence of cells with the co-expression of a progenitor cell-like or epithelial cell-like characteristic for combinations of both Vimentin/Cytokeratin or CD44/CD326.

In an evaluation of canine donor uterine tissue-derived cell cultures, the presence of cells dually-expressing several combinations of markers was investigated as shown in Table 13.

The expression profiles of the paired CD markers both support the identification of cells that simultaneously express both progenitor cell-like and epithelial cell-like characteristics.

Although there is donor-to-donor variation, each of the donor URC preparations in Tables 12 and 13 show the unexpected presence of both a progenitor cell-like marker (Vimentin and CD44) with an epithelial cell-like marker (CD326 and Cytokeratin-18) in the same cells for canine and feline URC preparations. As shown in Table 13, the high dual-expression percentages for canine URC preparations for CD44 and Vimentin indicates that the Vimentin marker in canine URCs is associated with progenitor-like cells. Thus, the combination of Vimentin and Cytokeratin dual positive cells identifies a population of cells in the URCs that display both progenitor cell-like and epithelial cell-like characteristics. This further supports the interpretation of the presence of feline URCs co-expressing Vimentin and Cytokeratin in the same cells in Example 15 as indicating that individual cells co-express both progenitor cell-like and epithelial cell-like properties. Reinforcing these observations, there are measurable percentages of both canine and feline URCs that express both CD44 and CD326, as well as canine cells co-expressing CD44 and Cytokeratin. These combinations of reagents detect feline and canine URCs that are both progenitor cell-like and epithelial cell-like.

The presence of cells in cultures of feline URCs and canine URCs that express both a progenitor cell-like marker and an epithelial cell-like marker demonstrates the existence of a unique form of progenitor cell derived from uterine tissue that can be cultured to high passage number and therefore is of interest for therapeutic purposes.

Example 17. Outcomes of Canine Donor Uterine Tissue-Derived Clinical Doses in Atopic Dermatitis Clinical doses were obtained from canine donor S-011, whose uterine tissue was processed as described in Protocol B, in order to digest the tissue with enzymes and culturing the resultant digestate. The cells were expanded in culture and cryopreserved at Passage 4, in CS10 (BioLife Solutions) at 36 million cells/cryovial. Doses were administered to qualified canine patients with atopic dermatitis via an IV infusion after the cells were thawed and diluted in PBS. Two clinical doses were infused with a two-week interval between doses, after which the clinical symptoms of each canine patient were monitored. The canine patients were assessed via a number of clinical metrics, including Pruritus Visual Analog Score (PVAS; an indication of the severity of pruritus (itchiness)), Canine Atopic Dermatitis Extent and Severity Index-4 (CADESI-4), and Canine Atopic Dermatitis Lesion Index (CADLI) both before treatment and post-treatment at intervals. The available clinical data is shown in Table 14.

TABLE 14

Outcome Scores for Canine Patients Treated for Atopic Dermatitis with Two Canine Uterine Tissue-derived Clinical Doses

| | PVAS | | CADESI-4 | | CADLI | |
|---|---|---|---|---|---|---|
| Patient ID | Pre-treatment | D30 | Pre-treatment | D30 | Pre-treatment | D30 |
| AD-I-01 | 7.25 | 6.7 | 49 | 35 | 23 | 19 |
| -02 | 7.9 | 7.7 | 40 | 39 | 13 | 13 |
| -04 | 5.5 | 5.3 | 90 | 70 | 26 | 19 |
| -05 | 4.0 | 2.4 | 98 | 87 | 39 | 31 |
| Ave (n = 4) | 6.2 | 5.5 | 69.2 | 57.8 | 25.2 | 20.5 |

The clinical benefit of treating canine patients with a confirmed diagnosis of atopic dermatitis was demonstrated from the trend in the clinical metrics that showed a reduction on average for the three metrics for the four canine patients treated compared to baseline pre-treatment values. A reduction in the clinical metrics indicated an improved clinical status for the patient.

PVAS is a validated scale to assess the severity of pruritus in a patient. This scale goes from a "Normal dog—no problem with itch" to "Extremely severe itching/almost continuous (needs to be physically restrained from itching)." The same pet owner performs this assessment at each study visit, based on their observation of the level of itchiness that they are seeing at home. CADESI-4 is a validated assessment tool to assess the condition of a dog's skin. It focusses on specific sites on the dog such as the front and hind paws, flanks and inguinal areas and measures the severity of erythema (redness), lichenification (skin thickening and excoriations (skin trauma)) and/or alopecia (hair loss). This assessment is performed by the same veterinarian at each study visit. CADLI is a validated assessment tool to assess the condition of a dog's skin. It is similar to the CADESI-4 assessment tool and functions in a similar manner with only slight technical differences. It focuses on more generalized areas of skin on the dog but still assesses the same measures of severity with the addition of hyperpigmentation (level of pigment in the skin). This assessment also is performed by the same veterinarian at each study visit.

Example 18. Cytokine Profiles of Canine and Feline URCs

Cytokines are important molecules secreted by progenitor cells that constitute the well-known paracrine mechanism for modulating both adult cells in tissue and immune cells. Cytokine profiles of canine URCs and feline URCs were obtained on culture supernatants from these cell preparations. Due to specificity, the canine and feline supernatants were analyzed separately by commercial assays. Two unrelated canine URCs (S-016 and S-002) were found to constitutively secret Galectin-3 (Participates in cell-cell adhesion, macrophage activation), MCP-1 (Monocyte chemoattractant Protein-1 attracts monocytes, memory T-cells and dendritic cells to sites of inflammation), IGFBP-2 (Insulin-like growth factor binding proteins participate in maintaining stemness, cell migration [chemotaxis]), and VEGF (Vascular endothelial growth factor—neovascularization) in the absence of a background level of the cytokines in culture medium. A feline donor (S-001) was found to secrete MIP-1, VEGF, PDGF (Platelet Derived Growth Factor that supports neovascularization and the proliferation of cells in tissues) and IL-10 (Interleukin-10 that acts to reduce the pro-inflammatory response of immune cells).

Example 19. Mixed Lymphocyte Reaction and IDO Activity and PGE$_2$ Levels

Progenitor cells have been assessed in a Mixed Lymphocyte Reaction (MLR) assay for their capability of inhibiting the proliferation of donor-derived monocytes. The assay was based on the use of isolated donor peripheral blood monocytes (PBMCs) that are stimulated (usually with a mitogen like Concanavalin A (Con A)) to proliferate (control condition) and compared with the same conditions but with the progenitor cell preparation (test condition). Decreasing the level of proliferation in the PBMC/Con A condition by adding URCs provides evidence that the URC preparations are capable of immunomodulation in pro-inflammatory conditions. In addition, supernatants from the PBMC/Con A/URC reaction were analyzed for Indoleamine-2,3-dioxygenase activity (IDO; assessment of the level of kynurenine, which is a major metabolite of the action of IDO on tryptophan) and levels of Prostaglandin E2 (PGE$_2$; measured in a commercial ELISA). Both IDO activity and PGE$_2$ have been established as biomarkers/effector molecules for down-regulation of immune response by T-cells resulting in a reduction in inflammation.

Table 15 shows the proliferation inhibition of a feline URC preparations when assessed in a feline PBMC MLR assay, along with the IDO activity and PGE$_2$ levels obtained on the supernatants. Table 16 shows the proliferation inhibition of canine URC preparations when assessed in a canine PBMC MLR assay, along with IDO activity and PGE$_2$ levels obtained on the supernatants. Note: IDO activity and PGE$_2$ levels were compared to the Donor PBMC+Con A values to determine fold-increase.

TABLE 15

Feline URC Preparations Proliferation Inhibition, IDO Activity and PGE$_2$ Levels

| Sample ID (Donor PBMC #) | PBMC Proliferation Inhibition (%) | IDO Activity (Kynurenine) Fold Increase | PGE2 Fold Increase |
|---|---|---|---|
| S-001 (Donor A) | 41.9 | NA | NA |
| S-001 (Donor B) | 55.9 | NA | NA |
| S-019 (Donor C) | NA | 1.4X | 7,536X |
| S-019 (Donor D) | NA | 1.9X | 10,017X |

TABLE 16

Canine URC Preparations Proliferation Inhibition, IDO Activity and PGE$_2$ Levels

| Sample ID (Donor PBMC #) | PBMC Proliferation Inhibition (%) | IDO Activity (Kynurenine) Fold Increase | PGE2 Fold Increase |
|---|---|---|---|
| S-011 (Donor E) | 48 | 1.4X | 128X |
| S-016 (Donor E) | 55 | 1.5X | 311X |
| S-011 (Donor F) | NA | 1.4X | 120X |
| S-016 (Donor F) | NA | 1.9X | 672X |

Both the canine and feline URC preparations showed a downregulation of proliferation in the MLR, indicating that the URCs possess the important immunomodulatory characteristic commonly associated with stem/progenitor cells. Furthermore, both canine and feline URC preparations produce IDO and PGE$_2$, which are known to participate in the immunomodulatory behavior of stem/progenitor cells toward activated immune cells.

Example 20. Differential In Vitro Growth Behavior of Unrelated Feline Donor Uterine Tissue-Derived URCs Several unrelated feline donor tissues were digested with Protocol C (Example 10). An equal portion of each digestate was split and cultured in either Lonza® DMEM or Corning® DMEM formulation (both containing 10% FBS and 8 ng/mL FGF-2). Each culture preparation was treated in an identical manner, with passaging of cells occurring when a culture showed approximately 70-80% confluence in the culture flask.

The cultures were passaged by detaching the adherent cells with an enzymatic agent, counting the cells, and reseeing the cells in fresh culture flasks with fresh media. Therefore, a culture needed to increase the number of cells during a culture interval in order for a passage to yield enough cells for the next reseeding to occur. Culture status was assessed as stopped growing/differentiated (SG/D) or growing (G) for each of the feline URC preparations by Passage number as shown in Table 17. Note that "NA" in Table 17 refers to a culture that stopped growing or differentiated (i.e. converted to an adult cell) in the preceding passage, so there were no cells to seed for the current passage. "L" refers to Lonza® DMEM and "C" refers to Corning® DMEM.

TABLE 17

Growth Patterns of Donor URCs in Lonza ® DMEM versus Corning ® DMEM
Cell Growth (Growing- G or Stopped Growing- SG)

| Sample ID | Passage 1 | | Passage 2 | | Passage 3 | | Passage 4 | | Passage 5 | |
|---|---|---|---|---|---|---|---|---|---|---|
| Medium | L | C | L | C | L | C | L | C | L | C |
| S-004 | G | G | G | G | SG/D | G | NA | SG/D | NA | NA |
| S-005 | G | G | G | G | G | G | G | G | SG/D | G |
| S-023 | G | G | G | G | G | G | SG/D | SG/D | NA | NA |
| S-001 | G | G | G | G | G | G | SG/D | G | NA | G |
| S-006 | G | G | G | G | G | G | SG/D | G | NA | G |
| S-007 | G | G | G | G | SG/D | G | NA | G | NA | G |

Two of the feline URC preparations, S-004 and S-007, stopped growing or differentiated (into adult cells that grew slowly if at all) in Lonza® DMEM during Passage 3. Two of the feline URC preparations, S-004 and S-023, stopped growing or differentiated (into adult cells that grew slowly if at all) in Corning® DMEM during Passage 4. Only one URC preparation, S-005, grew in Passage 4, but failed to grow in Passage 5 in Lonza® DMEM. Thus, 5/6 URC preparations failed to grow in Lonza® DMEM before Passage 5 and just 1/6 was seeded in Passage 5 but failed to grow. In contrast, 4/6 of the URC preparations grown in Corning® DMEM were seeded and grew in Passage 5. The other 2/6 URC preparations either stopped growing or differentiated into adult cells and weren't seeded in Passage 5.

The six unrelated feline donor URC preparations cultured in parallel from a common digestate grew poorly in Lonza® DMEM as seen in Table 17 where only one of the URCs was seeded in Passage 5 but failed to grow. In contrast, four of the URCs grew robustly in Corning® DMEM through Passage 5 without differentiating, while just two URCs failed to grow well (or differentiated) in Passage 4.

Differences between the compositions of Lonza® DMEM and Corning® DMEM are shown in Table 18.

TABLE 18

Differences in Composition of Lonza DMEM Versus Corning DMEM

| Component | Lonza ® DMEM (Cat # 12-917F) Levels | Corning ® DMEM (Cat # 10-013) Levels | Notes |
|---|---|---|---|
| Inositol | 7 mg/L | 7.2 mg/L | 2.8% difference |
| Phenol Red | Not added | Added | |
| Osmolality | 338 mOsm/kg H$_2$O (recent lot CoA) | 342 mOsm/kg H$_2$O (recent lot CoA) | The upper range for Osmolality for Corning is 365, while Lonza is 343 |

TABLE 18-continued

Differences in Composition of Lonza DMEM Versus Corning DMEM

| Component | Lonza ® DMEM (Cat # 12-917F) Levels | Corning ® DMEM (Cat # 10-013) Levels | Notes |
|---|---|---|---|
| Sodium Phosphate Monobasic | 108.7 mg/L | 125 mg/L | 15% difference |
| Glutamine | 0 mg/L | 584 mg/L (4 mM) | Lonza DMEM is supplemented with Glutamine up to 5.5 mM or 6 mM |

Impact on Differences of Composition:

Inositol: Inositol is an important in vivo cofactor involved in neurotransmission, and the binding of steroid hormones. It has been found to participate in plasma membrane metabolism and is influenced by levels of glucose. Since cells can synthesize inositol, the impact of a 2.8% difference in exogenous inositol is unknown.

Phenol Red: Phenol Red is used as a pH indicator, which can act as an indicator of culture health and metabolic activity. It has been identified as having weak estrogenic activity, can be a target for redox reactions, and has been shown to influence differentiation activity of MSCs. None of these influences would seem to have a direct bearing on the culturing efficiency of the media for uterine tissue-derived cells.

Osmolality/Sodium Phosphate Monobasic: Sodium phosphate monobasic is one of the inorganic salts that contributes to the osmolality of the culture medium and is part of the buffering capacity of the medium. The impact of a 15% higher level of this species in the Corning® medium might be seen in the higher value an exemplary lot of Corning® DMEM has for its osmolality, which is at the upper limit of osmolality for Lonza® DMEM.

Glutamine: Glutamine is an important amino acid required in protein synthesis. Lonza® DMEM lacks glutamine. However, glutamine was added as a supplement to the basal medium whenever a complete medium was needed. The level of glutamine was adjusted to reach 5.5 mM. Corning® medium contains 4 mM glutamine, which is approximately 73% of the level in glutamine-supplemented Lonza® DMEM.

Overall, URC preparations cultured in Corning® DMEM showed more robust growth through Passage 5 compared to much poorer growth in Lonza® DMEM. The differences between the two media are limited, as shown in Table 18, but glutamine is substantially lower by 27% in Corning® DMEM. While not being bounded by one theory or mechanism, a lower level of glutamine might create a less favorable environment for the attached cells to differentiate into adult cells.

Example 21. Influence of Decontamination Treatment of Feline Uterine Tissues on Growth of Cells Obtained by Enzymatic Digestion While uterine tissue is obtained from dogs and cats during a sterile spay procedure, there remains a risk of microbial contamination. Accordingly, alternative protocols for creating clinical doses were evaluated (Protocol D). Protocol D is one protocol for minimizing the potential for microbial contamination of cells placed into culture after enzymatic digestion of the uterine tissue and involved an initial decontamination step prior to additional processing. Additional aspects of Protocol D are described in Table 20. The decontamination step in Protocol D uses a 1% (poly)vinylpyrrolidone (PVP) solution and a 0.1% sodium thiosulfate solution, followed by rinses in PBS. A different decontamination condition than that of Protocol D was also assessed that involved rinsing the uterine tissue in four washes of PBS. An assessment of the two decontamination methods was made by obtaining three feline spay tissues, dissecting away the non-uterine tissue and then dividing the uterine tissue for each donor into two equal portions. One portion was processed as follows:

1. Place the uterine tissue in a 50 mL conical tube containing 10 mL of PBS and mix gently to expose the tissue to PBS.
2. Clean the forceps that will be used for the tissue transfers by wiping with 70% isopropyl alcohol.
3. Transfer the uterine tissue from the first PBS tube to a second 50 mL conical tube containing 10 mL of PBS and mix gently to expose the tissue to the PBS.
4. Transfer the uterine tissue to a 50 mL conical tube containing 5 mL of 1% PVP. Mix gently and allow the incubation to continue for 2 minutes.
5. After the 2 minute incubation in the PVP solution is completed, remove the tissue from the PVP conical tube and place the uterine tissue in a 50 mL conical tube containing 5 mL of 0.1% sodium thiosulfate. Allow the uterine tissue to incubate in the 0.1% sodium thiosulfate solution for 1 minute.
6. After the 1 minute incubation in the sodium thiosulfate solution is completed, remove the tissue from the sodium thiosulfate conical tube and place the uterine tissue in a 50 mL conical tube containing 10 mL of PBS. Gently mix the tube to expose the tissue to the PBS.
7. Transfer the uterine tissue from the PBS tube to another 50 mL conical tube with 10 mL of PBS. Gently mix the tube to expose the tissue to the PBS.

The other portion of uterine tissue was decontaminated by placing the tissue in four separate 50 mL conical tubes containing 10 mL of PBS each.

Each portion of tissue was minced and digested with identical conditions (collagenase and thermolysin, 30 minute digestion with use of manual shaking of the tubes by hand at 10 minute intervals). The digestates were placed in flasks and incubated in complete medium (DMEM, high glucose, 10% FBS and 8 ng/mL FGF-2, with 0.44 µg/mL Amphotericin B and 0.05 mg/mL Gentamicin) in 37° C./5% $CO_2$/100% humidity. Cultures were examined on a daily basis for contamination, harvested on Day 4, and a total cell number for each decontamination treatment for each donor was determined. The cell yield for cultures with PBS-decontaminated tissue was divided by the corresponding cell yield for cultures with PVP/thiosulfate-decontaminated tissue for each donor and multiplied by 100 to get a value of % growth (cell number) for the PBS-treated cell culture compared to PVP/thiosulfate (control) treated cell culture for each donor as shown in Table 19.

TABLE 19

% Growth (total cell number) of PBS-treated decontamination compared to PVP/thiosulfate decontamination cultures by donor

| Sample ID | Growth with PBS Decontamination/ PVP-thiosulfate Decontamination (%) |
|---|---|
| S-020 | 269.8 |
| S-021 | 574.4 |
| S-022 | 92.0 |
| Average | 312.1 |

No contamination was observed in cultures of the three donor tissues for either condition, but there was a substantial increase in the average cell yield during culturing for 4 days in favor of using PBS. The current Protocol C uses PBS as the means for decontamination of uterine tissue when processed for enzymatic digestion to create clinical doses.

Example 22. Comparison of Protocol C and Protocol D

There are a number of additional differences that distinguish Protocol C from Protocol D. The differences are listed in Table 20.

TABLE 20

Comparison between Protocol C and Protocol D for Producing Clinical Doses

| Protocol Area | Step/Treatment | Procotol C (clinical dose) | Protocol D (clinical dose) |
|---|---|---|---|
| Uterine tissue processing | decontamination | PBS used | Poly(vinylpyrrolodone) 1% solution, 0.1% sodium thiosulfate, PBS |
| Uterine tissue processing | Tissue mincing | 2 mm × 2 mm pieces | Mince and dice into fine pieces |
| Uterine tissue processing | Enzymatic Digestion | Collagenase and Thermolysin | Collagenase and Thermolysin |
| Uterine tissue processing | Mechanical Force | Manual shaking at 10-minute intervals | Manual shaking at 10-minute intervals |
| Uterine tissue processing | Digestion time | 60 minutes | 30 minutes |
| Culture | Medium | Corning DMEM | Lonza DMEM |
| Culture | Medium | Penicillin, Streptomycin, Normocin | Amphotericin B, Gentamicin |
| Culture | Medium | Glutamine at 4 mM | Supplement Glutamine to 5.5 mM |
| Culture | Initial Containers | T225 flasks | T225 flasks |
| Culture | Day 1 processing | No activity | Remove tissue pieces and culture fluid, return tissue pieces and fresh medium |
| Culture | Day 3 processing | Replace culture medium | Replace culture medium |
| Culture | Day 4 processing (or when cells are 70-80% confluent) | Harvest cells and cryopreserve as Master Cell Bank (cryopreserved in CS10, BioLife Solutions) | Harvest cells and cryopreserve as Master Cell Bank (cryopreserved in 10% DMSO/complete culture medium containing 10% Fetal Bovine Serum) |
| Culture | Generate expanded number of cells-second culture interval | Use flatware for expansion of cells | Use flatware for expansion of cells |
| Culture | Generate cryopreserved cells-third culture interval | Use flatware for Working Cell Bank (cells cryopreserved in CS10) | Use 1-liter spinner culture (suspended microcarrier particles) for Working Cell Bank (cells cryopreserved in 10% DMSO/complete culture medium) |
| Culture | Generate cells-fourth culture interval | Use an immobile plastic-surface culture system (Pall's Xpansion) to expand cells and harvest for clinical doses | Use 1-liter spinner culture (suspended microcarrier particles) for Working Cell Bank |
| Culture | Expand cells and harvest clinical doses | NA | Use multi-liter bioreactor (suspended microcarrier particles (Eppendorf) |

TABLE 20-continued

Comparison between Protocol C and Protocol D for Producing Clinical Doses

| Protocol Area | Step/Treatment | Procotol C (clinical dose) | Protocol D (clinical dose) |
|---|---|---|---|
| Clinical Doses | Cryopreserve clinical doses | Use a commercial cryopreservation solution (CS10) | Use 2% DMSO in HESPAN (6% hydroxethylstarch in saline) |

There are a number of key differences between Protocol C and Protocol D.

1. Tissue Processing:
   A) Decontamination of the tissue in Protocol D exposes the tissue to harsh chemicals whereas Protocol C uses tissue-friendly PBS for decontamination. Protocol D decontamination solutions have been shown to reduce cell yield during the first culturing interval due to an impact on the cells of the tissue.
   B) Protocol C digests the tissue for 60 minutes compared to just 30 minutes in Protocol D. The longer digestion time has been shown to produce a composition of cells in the digestate that can reach 70-80% confluence more quickly (3 days) compared to a paired tissue digestate produced with just a 30 minute digestion duration, which took 5 days to reach 70-80% confluence.
2. Culturing of the Digestate and Cells:
   A) Protocol C allows the cells and tissue explants to remain in culture undisturbed until Day 3, whereas Protocol D removes the culture fluid and tissue pieces on Day 1, and redistributes the tissue pieces along with fresh medium back into the culture flasks. The culture fluid is replaced on Day 3 in both protocols. The impact of removing the culture fluid on Day 1 is difficult to assess, but clearly any biomolecules that had diffused out of the tissue or had been secreted by the cells and into the surrounding fluid would be lost in Protocol D. From the experimental result indicated in Item 1B of the key differences above, it was observed that the tissue pieces digested for 30 minutes took roughly two days longer to reach confluence compared to tissue pieces digested for 60 minutes. The longer exposure to the digesting enzyme might have created a more disrupted tissue matrix compared to the shorter incubation time, thereby allowing cells and biomolecules to leave the tissue matrix more readily and enter the culture fluid milieu, thereby contributing to a faster time to confluence.
   B) Another potentially critical difference is the use of Amphotericin B and gentamicin in the Protocol D culture medium. Both of these antibiotics are known to be harsh on cells. For example, Amphotericin B has been reported to decrease viability of cells during culture. Penicillin and streptomycin also transiently decreases viability of cells in culture. This type of behavior suggests that Amphotericin B, and other antibiotics, may be negatively influencing the cells in some fashion. Thus, the Protocol D culturing milieu that contains Amphotericin B and gentamicin may be influencing the cultured cells in ways that the Protocol C culturing milieu doesn't since Protocol C does not use Amphotericin B or gentamicin.
   C) Protocol C uses Corning® DMEM for culturing the cells, while Protocol D uses Lonza® DMEM. The differences in composition of these two DMEM formulations is shown in Table 18. The level of glutamine is lower in the Corning® DMEM by approximately 27% compared to the glutamine level in the Lonza® DMEM, which as indicated in the culturing response of six unrelated feline donor URC preparations (Table 17) might account for the greater number of donor preparations reaching Passage 5 (n=4 out of 6) when grown in the culture medium used in Protocol C, compared to just 1 out of 6 of the preparations reaching Passage 5 for the Protocol D culture medium.
3. Cell Expansion to Create Clinical Doses:
   A) The manufacturing process used in Protocol D to produce clinical doses as shown in Table 20 involves four intervals of culturing after generating the master cell bank (MCB) stage of cryopreserved cells. Three intervals of culturing after generating the MCB stage of cryopreserved cells is used. In view of the data shown in Table 17, which showed poorer growth patterns for URCs grown in Protocol D's Lonza® DMEM formulation, Protocol C has a greater potential to obtain useful doses given its superior growth pattern for its Corning® DMEM formulation.
   B) A significant difference in the technology used to expand cells prior to clinical dose cryopreservation is shown in Table 20. Protocol D relied on the use of microcarrier particles that are kept in suspension with an impeller, which is refereed to as a spinner flask technology. Cells attach to the microcarrier particles and remain suspended during the culturing intervals by the rotation of the impeller. A bioreactor is a much larger example of spinner flask technology, but exerts a very sophisticated control over the composition of the gas phase through active monitoring of $CO_2$ and oxygen (and can introduce nitrogen if necessary). Protocol C does not use a spinner flask or impeller-based bioreactor technology for expanding cells to create clinical doses, but instead relies on a specialized high density, multi-plate bioreactor technology that is especially designed for cell types that might be adversely affected by the shear forces present in impeller-based bioreactors. Protocol C avoids the shear-inducing, impeller-based bioreactor environment in favor of stationary culture, providing for a more consistent expansion of URC preparations.
4. Cryopreservation Formulations:
   A) Protocol D uses two formulations during the process to create clinical doses with URC preparations. The first cryoprotectant formulation was based on use of culture medium containing 10% FBS, which was mixed with DMSO to yield a final 10% DMSO/5% FBS containing cryoprotectant. This formulation was used for any cryopreservation of cultured cells prior to generating clinical doses. Protocol D's clinical doses were cryopreserved in a solution composed of 2% DMSO (final) and a commercial preparation (HESPAN, B. Braun Medical) of 6% hydroxyethylstarch (HES) in 0.9% saline.

B) Protocol C uses a commercially available (BioLife Solutions) cryoprotectant called CS10 for all cryopreservation of cells, including clinical doses.

Taken together, there are substantial differences between Protocol C developed to obtain a more optimal culturing and yield of clinical doses of canine and feline URCs compared to Protocol D. The differences include digestion times, culture medium antibiotics, culture medium component compositions (e.g. level of glutamine), and the bioreactor technology used for cell expansion to create clinical doses. It is clear that more donor tissue can be processed to a clinical dose in the Protocol C processing and culturing approach compared to the performance of the Protocol D approach as shown in Table 17.

Example 23. Administration of URCs

URC doses are provided as cryopreserved doses requiring in-clinic thawing or as a thawed dose ready to administer to the patient upon arrival to the clinic. If a cryopreserved dose is provided to a clinic, it is shipped in a suitable temperature-controlled container that maintains it in a temperature before −120° C. If a thawed dose is provided to the clinic, it is shipped in a suitable temperature-controlled container that maintains a temperature between 1° C. and 8° C. A URC cryopreserved dose is contained in a sterile, cryogenic-temperature stable vial (e.g. CellSeal vial, Sexton Biotechnologies) with URCs that have been cryopreserved in a suitable cryoprotectant (e.g. CS10, BioLife Solutions). A URC thawed dose is contained in a sterile syringe or similar closed, sterile container without a headspace or air gap. The URC thawed dose is thawed prior to shipment and is suspended in a compatible fluid like PBS, lactated Ringer's solution, normal saline, or other fluids compatible with maintaining viable nucleated cells.

The URC cryopreserved dose is thawed by one of several means including dry heat (e.g. heating pad) or an instrument designed to apply controlled dry heating (ZipThaw, FreMon Scientific) or use of a 37° C. water bath or being left at room temperature until no ice remains visible. The URC cryopreserved dose is withdrawn from the cryovial and placed in container suitable for administering to a patient, like a syringe. The syringe can be pre-filled prior to being loaded with the URCs from the cryovial with a suitable diluent, like PBS, lactated Ringer's solution, normal saline, or other fluids compatible with maintaining viable nucleated cells. The URCs can be administered to the patient in an undiluted form, or diluted by 1.5×, 2×, 3×, 4×, 5×, 6×, 7×, 8×, 9×, 10×, or at least 1.5×, 2×, 3×, 4×, 5×, 6×, 7×, 8×, 9×, or 10× prior to being administered to a patient. The URC thawed dose will usually be diluted by 1.5×, 2×, 3×, 4×, 5×, 6×, 7×, 8×, 9×, 10×, or at least 1.5×, 2×, 3×, 4×, 5×, 6×, 7×, 8×, 9×, or 10× prior to being shipped to the clinic. URCs can be administered through a variety of routes, including intravenous (IV), intraarterial (IA), intrathecal (IT), intra-parenchymal (IP), intralesional, topical (dermal wound), intradermal (ID), subcutaneous (SC), and intramuscular (IM) injection. Specialized medical components, including syringes, needles, IV sets with cannulae, extension sets, T-connector sets and other components might be utilized to administer the URCs by the routes cited. Administration of the URCs can be performed manually or dispensed with the use of syringe pump.

The target pathology and condition of the patient may influence how URCs are administered, influencing the number of injections, the interval between injections, the use of a single route or use of a mixed set of routes for injections, and the number of URCs injected. The URC dose typically will contain from a minimum of 20 million cells up to a maximum of 40 million cells, with a preferred number of cells of between 30 and 36 million cells per dose.

The invention is generally disclosed herein using affirmative language to describe the numerous embodiments. The invention also includes embodiments in which subject matter is excluded, in full or in part, such as substances or materials, method steps and conditions, protocols, or procedures.

In at least some of the previously described embodiments, one or more elements used in an embodiment can interchangeably be used in another embodiment unless such a replacement is not technically feasible. It will be appreciated by those skilled in the art that various other omissions, additions and modifications may be made to the methods and structures described above without departing from the scope of the claimed subject matter. All such modifications and changes are intended to fall within the scope of the subject matter, as defined by the appended claims.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into sub-ranges as discussed above. Finally, as will be understood by one skilled in the art, a range includes each individual member. Thus, for example, a group having 1-3 articles refers to groups having 1, 2, or 3 articles. Similarly, a group having 1-5 articles refers to groups having 1, 2, 3, 4, or 5 articles, and so forth.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

All references cited herein, including but not limited to published and unpublished applications, patents, and literature references, are incorporated herein by reference in their entirety and are hereby made a part of this specification. To the extent publications and patents or patent applications incorporated by reference contradict the disclosure contained in the specification, the specification is intended to supersede and/or take precedence over any such contradictory material.

What is claimed is:

1. A composition comprising a mixture of: i) a population of mesenchymal progenitor cells and a population of epithelial progenitor cells, each of which are obtained from dissociated feline uterine tissue and ii) a cryopreservation medium, wherein the mesenchymal progenitor cells and the epithelial progenitor cells are in a ratio from about 1:5 to about 5:1.

2. The composition of claim 1, wherein the population of the mesenchymal progenitor cells and the population of the epithelial progenitor cells comprise cells that are vimentin-positive (V+)/cytokeratin-negative (C−) cells and V+/cytokeratin-positive (C+), wherein the V+/C− cells and V+/C+ cells are present in a ratio from about 1:5 to about 5:1.

3. The composition of claim 1, further comprising fibroblast growth factor 2 (FGF-2) or recombinant human FGF-2.

4. The composition of claim 1, wherein the cryopreservation medium comprises components selected from the group consisting of:
DMSO-containing medium;
about 98% of a solution comprising 6% hydroxyethyl starch in 0.9% sodium chloride and about 2% DMSO; and
about 2-10% DMSO and about 2-20% FCS, wherein the DMSO and FCS are diluted in a growth medium.

5. The composition of claim 1, wherein the population of mesenchymal progenitor cells and the population of epithelial progenitor cells are in a ratio of about 2:3.

6. The composition of claim 1, wherein the population of mesenchymal progenitor cells and the population of epithelial progenitor cells are in a ratio of about 3:2.

7. The composition of claim 1, wherein the population of mesenchymal progenitor cells and the population of epithelial progenitor cells are in a ratio of about 5:1.

8. The composition of claim 2, wherein the population of V+/C− cells and the population of V+/C+ cells are in a ratio of at least about 2:3.

9. The composition of claim 2, wherein the population of V+/C− cells and the population of V+/C+ cells are in a ratio of about 3:2.

10. The composition of claim 2, wherein the population of V+/C− cells and the population of V+/C+ cells are in a ratio of about 5:1.

11. A container that is not pre-treated with biological or synthetic coatings that enhance cell attachment and/or growth, the container comprising a composition of cells, wherein the composition of cells comprises a mixture of:
i) a population of mesenchymal progenitor cells and a population of epithelial progenitor cells, each of which are obtained from dissociated feline uterine tissue and
ii) a cryopreservation medium, wherein the mesenchymal progenitor cells and the epithelial progenitor cells are in a ratio from about 1:5 to about 5:1.

12. The container of claim 11, wherein the container is not coated with a cell-based feeder layer, a polymer, a protein, a polypeptide, a peptide, an antibody, a nucleic acid molecule, a DNA, an RNA, a sugar, a polysaccharide, a carbohydrate, a lipid, a poly-lysine, a poly-ornithine, a collagen, a gelatin, a fibronectin, a vitronectin, a laminin, an elastin, a tenascin, a heparan sulfate, an entactin, a nidogen, an osteopontin, an extracellular matrix, a basement membrane, a hydrogel, a polyethylenimine, a wheat germ agglutinin, a hyaluronic acid, or any combination thereof.

13. The container of claim 11, wherein the population of the mesenchymal progenitor cells and the population of the epithelial progenitor cells comprise cells that are vimentin-positive (V+)/cytokeratin-negative (C−) cells and V+/cytokeratin-positive (C+), wherein the V+/C− cells and V+/C+ cells are present in a ratio from about 1:5 to about 5:1.

14. The container of claim 11, further comprising fibroblast growth factor 2 (FGF-2) or recombinant human FGF-2.

15. The container of claim 11, wherein the cryopreservation medium comprises components selected from the group consisting of:
DMSO-containing medium;
about 98% of a solution comprising 6% hydroxyethyl starch in 0.9% sodium chloride and about 2% DMSO; and
about 2-10% DMSO and about 2-20% FCS, wherein the DMSO and FCS are diluted in a growth medium.

16. The container of claim 11, wherein the composition of cells is frozen.

17. The composition of claim 1, wherein the mesenchymal progenitor cells and the epithelial progenitor cells are further defined by a population of cells positive for both CD44 and CD326.

18. The composition of claim 1, wherein the mesenchymal progenitor cells and the epithelial progenitor cells are 4 passage cultured mesenchymal progenitor cells and epithelial progenitor cells.

19. The container of claim 11, wherein the composition of mesenchymal progenitor cells and epithelial progenitor cells are $CD44^+$ and $CD326^+$.

20. The container of claim 11, wherein the composition of mesenchymal progenitor cells and epithelial progenitor cells are 4 passage cultured mesenchymal progenitor cells and epithelial progenitor cells.

* * * * *